US010519292B2

(12) United States Patent
Yao et al.

(10) Patent No.: US 10,519,292 B2
(45) Date of Patent: Dec. 31, 2019

(54) PRODUCTS FROM THE DECOMPOSITION OF PLASTIC WASTE

(71) Applicant: BIOCELLECTION INC., Menlo Park, CA (US)

(72) Inventors: Jia Yun Yao, Redwood City, CA (US); Yu Wen Wang, Santa Clara, CA (US); Tapaswy Muppaneni, Newark, CA (US); Ruja Shrestha, Fremont, CA (US); Jennifer Le Roy, Mountain View, CA (US); Garret D. Figuly, Wilmington, DE (US)

(73) Assignee: BioCellection Inc., Menlo Park, CA (US)

( * ) Notice: Subject to any disclaimer, the term of this patent is extended or adjusted under 35 U.S.C. 154(b) by 0 days.

(21) Appl. No.: 16/422,401

(22) Filed: May 24, 2019

(65) Prior Publication Data

US 2019/0322833 A1 Oct. 24, 2019

Related U.S. Application Data

(63) Continuation of application No. PCT/US2019/028258, filed on Apr. 19, 2019, which is a continuation-in-part of application No. 15/958,745, filed on Apr. 20, 2018, now abandoned.

(60) Provisional application No. 62/793,295, filed on Jan. 16, 2019, provisional application No. 62/660,156, filed on Apr. 19, 2018.

(51) Int. Cl.
*C08J 11/16* (2006.01)
*C07C 51/487* (2006.01)

(52) U.S. Cl.
CPC ............ *C08J 11/16* (2013.01); *C07C 51/487* (2013.01); *C08J 2323/06* (2013.01); *C08J 2423/06* (2013.01)

(58) Field of Classification Search
CPC ........ C08J 11/10; C08J 11/16; C08J 2423/06; C08J 2323/06; B09B 3/0083; C07C 67/03; C07C 67/48; C07C 69/40; C07C 69/42; C07C 69/44; C07C 69/46; C07C 69/48; C07C 69/50; C07C 55/00; C07C 55/02; C07C 55/16; C07C 55/20; C07C 55/40
See application file for complete search history.

(56) References Cited

U.S. PATENT DOCUMENTS 2,824,122 A 2/1958 Kuceski
2,824,123 A 2/1958 Kuceski
(Continued)

FOREIGN PATENT DOCUMENTS

JP 4974924 B2 7/2002
JP 4974924 B2 7/2012
(Continued)

OTHER PUBLICATIONS

Garaeva et al., Composition, Properties, and Application of Products Formed in Oxidation of Polyethylene by Nitric Acid, Russian Journal of Applied Chemistry, 2010, vol. 83, No. 1, pp. 97-101.
(Continued)

*Primary Examiner* — Frances Tischler
(74) *Attorney, Agent, or Firm* — Sterne, Kessler, Goldstein & Fox P.L.L.C.

(57) ABSTRACT

This invention relates to the field of plastic waste decomposition. More specifically, the invention comprises products obtained from the decomposition of plastic waste.

8 Claims, 26 Drawing Sheets

(56) References Cited

U.S. PATENT DOCUMENTS

| | | | |
|---|---|---|---|
| 2,824,134 | A | 2/1958 | Hill et al. |
| 3,810,937 | A | 5/1974 | Kuceski |
| 10,000,715 | B2 | 6/2018 | Kumar et al. |
| 2002/0103301 | A1 | 8/2002 | Yoshida |
| 2008/0045617 | A1 | 2/2008 | Goto et al. |
| 2011/0172371 | A1 | 7/2011 | Goto et al. |
| 2015/0361374 | A1 | 12/2015 | Kumar et al. |

FOREIGN PATENT DOCUMENTS

| | | | |
|---|---|---|---|
| WO | 2000066656 | A1 | 11/2000 |
| WO | 2014031305 | A1 | 2/2014 |

OTHER PUBLICATIONS

Pifer et al., Chemical Recycling of Plastics to Useful Organic Compounds by Oxidative Degradation, Angewandte Chemie International Edition, 1998, vol. 37(23), pp. 3306-3308.

Remias et al., Oxidative Chemical Recycling of Polyethene, Comptes Rendus de l'Académie des Sciences—Series IIC—Chemistry, 2000, vol. 3(7), pp. 627-629.

Melby, L. Russell, Nitric Acid Oxidation of High-Density Polyethylene. Organic Chemical Aspects, Macromolecules, 1978, vol. 11(1), pp. 50-56.

Backstrom, E. et al., "Trash to Treasure: Microwave-Assisted Conversion of Polyethylene to Functional Chemicals," Ind Eng Chem Res 56:14814-21, American Chemical Society, United States (2017).

Garaeva, S.R. et al., "Composition, Properties, and Application of Products Formed in Oxidation of Polyethylene by Nitric Acid," Russian Journal of Applied Chemistry 83(1):97-101, Pleiades Publishing Ltd., Russia (2010).

Melby, L.R., "Nitric Acid Oxidation of High-Density Polyethylene. Organic Chemical Aspects," Macromolecules 11(1):50-6, American Chemical Society (1978).

Rueda, D.R., et al., "Degradation of Bulk Polyethylene by Nitric Acid, 1 IR Study of Oxidized Groups," Makromol Chem 182:2705-13, Hüthig & Wepf Verlag, Germany (1981).

Office Action dated Nov. 14, 2018, in U.S. Appl. No. 15/958,745, Yao et al., filed Apr. 20, 2018, 17 pages.

Office Action dated Aug. 23, 2018, in U.S. Appl. No. 15/958,745, Yao et al., filed Apr. 20, 2018, 16 pages.

Co-pending Application, U.S. Appl. No. 16/422,423, Inventors Yao, J.Y. et al., filed on May 24, 2019 (Not Published).

Unverified English language machine translation of JP 4974924 B2 (cited as document FP3 on accompanying PTO/SB/08A), Jul. 11, 2012.

International Search Report and Written Opinion for International Patent Appl. No. PCT/US2019/028258, European Patent Office, The Netherlands, dated Oct. 2019.

Office Action dated Oct. 7, 2019, for U.S. Appl. No. 16/422,423, filed May 24, 2019, inventors: Yao et al., U.S. Patent and Trademark Office, Alexandria, VA.

Co-pending Application, U.S. Appl. No. 16/657,266, Inventors Yao, J.Y. et al., filed on Oct. 18, 2019 (Not Published).

| Summary of LCMS Results – *D1 Crude* | | | | | | | |
|---|---|---|---|---|---|---|---|
| *RT* | *Positive m/z* | *Negative m/z* | Mass | Best Match | Score | Diff | ID |
| 0.551 | 133.0494 | 131.0351 | 132.0421 | $C_5 H_8 O_4$ | 95.44 | -1.45 | Glutaric acid |
| 1.093 | 147.065 | 145.0506 | 146.0576 | $C_6 H_{10} O_4$ | 99.49 | -2.29 | Adipic acid |
| 1.557 | 190.1067 | 171.0659 | 172.0727 | $C_8 H_{12} O_4$ | 89.87 | -5.28 | Octenedioic acid |
| 1.756 | 249.1074 | | 231.0739 | $C_9 H_{13} N O_6$ | 92.65 | -1.88 | Nitro-azelaic acid related |
| 1.97 | 161.0804 | 159.066 | 160.0731 | $C_7 H_{12} O_4$ | 98.78 | -2.93 | Pimelic acid |
| 2.014 | 242.063 | 218.0666 | 219.0739 | $C_8 H_{13} N O_6$ | 98.59 | -1.54 | Nitro-suberic acid |
| 2.05 | 187.0962 | 185.081 | 186.0885 | $C_9 H_{14} O_4$ | 97.61 | -4.04 | Nonenedioic acid |
| 2.086 | 263.1235 | | 245.0899 | $C_{10} H_{15} N O_6$ | 95.49 | -0.15 | Nitro-sebacic acid related |
| 2.352 | 251.1237 | 232.0825 | 233.0899 | $C_9 H_{15} N O_6$ | 99.23 | -0.34 | Nitro-azelaic acid |
| 2.398 | 201.1119 | 199.0969 | 200.1049 | $C_{10} H_{16} O_4$ | 97.04 | 0.09 | Decenedioic acid |
| 2.42 | 282.0949 | | 259.106 | $C_{11} H_{17} N O_6$ | 89.34 | 1.4 | Nitro-undecenedioic acid related |
| 2.42 | 197.0778 | 173.0815 | 174.0885 | $C_8 H_{14} O_4$ | 97.66 | -4.32 | Suberic acid |

FIG. 22A

| Summary of LCMS Results – *D1 Crude* | | | | | | | |
|---|---|---|---|---|---|---|---|
| *RT* | *Positive m/z* | *Negative m/z* | Mass | Best Match | Score | Diff. | ID |
| 2.577 | 265.1394 | 246.0981 | 247.1056 | $C_{10}H_{17}NO_6$ | 99.91 | 0.13 | Nitro-sebacic acid |
| 2.749 | 274.1303 | | 273.122 | $C_{12}H_{19}NO_6$ | 85.56 | 2.86 | Nitro-dodecanedioic acid related |
| 2.773 | 215.1266 | 213.1124 | 214.1201 | $C_{11}H_{18}O_4$ | 79.62 | -1.7 | Undecenedioic acid |
| 2.849 | 189.1118 | 187.0972 | 188.1046 | $C_9H_{16}O_4$ | 98.94 | -1.39 | Azelaic acid |
| 2.906 | 279.1551 | 260.114 | 261.1213 | $C_{11}H_{19}NO_6$ | 99.84 | 0.26 | Nitro-undecanedioic acid |
| 2.966 | 338.1578 | | 315.1685 | $C_{15}H_{25}NO_6$ | 92.82 | 1.04 | Nitro-pentadecanedioic acid related |
| 2.98 | 305.1704 | | 287.137 | $C_{13}H_{21}NO_6$ | 77.82 | 0.55 | Nitro-brassylic acid related |
| 3.053 | 352.1716 | | 329.1818 | $C_{16}H_{27}NO_6$ | 76.53 | -6.28 | Nitro-hexadecanedioic acid related |
| 3.166 | 298.1264 | 274.1296 | 275.1371 | $C_{12}H_{21}NO_6$ | 99.35 | 0.76 | Nitro-dodecanedioic acid |
| 3.2 | 366.1872 | | 343.1984 | $C_{17}H_{29}NO_6$ | 85.67 | -3.11 | Nitro-heptadecanedioic acid related |
| 3.256 | 225.1096 | 201.1128 | 202.1201 | $C_{10}H_{18}O_4$ | 99.63 | -2.24 | Sebacic acid |
| 3.45 | 307.1865 | 288.1455 | 289.1526 | $C_{13}H_{23}NO_6$ | 99.49 | 0.31 | Nitro-brassylic acid |
| 3.554 | 380.203 | | 357.2135 | $C_{18}H_{31}NO_6$ | 87.19 | -4.68 | Nitro-octadecanedioic acid related |
| 3.609 | 217.1434 | 215.1287 | 216.1362 | $C_{11}H_{20}O_4$ | 98.95 | 0.3 | Undecanedioic acid |
| 3.666 | 394.2188 | | 371.2291 | $C_{19}H_{33}NO_6$ | 86.01 | -4.67 | Nitro-nonadecanedioic acid related |

FIG. 22B

| Summary of LCMS Results – *D1 Crude* | | | | | | | |
|---|---|---|---|---|---|---|---|
| *RT* | *Positive m/z* | *Negative m/z* | Mass | Best Match | Score | Diff. | ID |
| 3.689 | 321.2019 | 302.1612 | 303.1681 | $C_{14} H_{25} N O_6$ | 99.3 | -0.31 | Nitro-tetradecanedioic acid |
| 3.711 | 319.1868 | | 301.1535 | $C_{14} H_{23} N O_6$ | 71.9 | 3.36 | Nitro-tetradecanedioic acid related |
| 3.913 | 231.1586 | 229.1446 | 230.1513 | $C_{12} H_{22} O_4$ | 96.59 | -2.11 | Dodecanedioic acid |
| 3.943 | 335.2182 | 316.1767 | 317.1843 | $C_{15} H_{27} N O_6$ | 98.97 | 1.52 | Nitro-pentadecanedioic acid |
| 3.995 | 408.2342 | | 385.2441 | $C_{20} H_{35} N O_6$ | 79.04 | -5.97 | Nitro-icosanedioic acid related |
| 4.159 | 349.2338 | 330.1921 | 331.1999 | $C_{16} H_{29} N O_6$ | 98.64 | 1.13 | Nitro-hexadecanedioic acid |
| 4.17 | 245.1743 | 243.16 | 244.1673 | $C_{13} H_{24} O_4$ | 96.04 | -0.48 | Brassylic acid |
| 4.343 | 363.2491 | 344.2073 | 345.2153 | $C_{17} H_{31} N O_6$ | 96.83 | 0.48 | Nitro-heptadecanedioic acid |
| 4.405 | 281.1729 | 257.1755 | 258.1829 | $C_{14} H_{26} O_4$ | 97.92 | -0.98 | Tetradecanedioic acid |
| 4.532 | 382.22 | 358.2233 | 359.2305 | $C_{18} H_{33} N O_6$ | 97.4 | -0.69 | Nitro-octadecanedioic acid |

FIG. 22C

PRODUCTS FROM THE DECOMPOSITION OF PLASTIC WASTE

CROSS-REFERENCE TO RELATED APPLICATIONS

This application is a continuation of International Patent Application No. PCT/US2019/028258, filed Apr. 19, 2019, which is a continuation-in-part of U.S. patent application Ser. No. 15/958,745, filed Apr. 20, 2018, and which claims the benefit of U.S. Provisional Patent Application No. 62/660,156, filed Apr. 19, 2018, and U.S. Provisional Patent Application No. 62/793,295, filed Jan. 16, 2019.

FIELD OF THE INVENTION

This invention relates to the field of contaminated plastic waste decomposition. More specifically, the invention comprises products obtained by decomposition of plastic waste.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Plastic pollution is a global environmental crisis for many reasons. Plastics are made to be durable rather than degradable. The ones that are biodegradable demonstrate shortcomings such as high production costs and functionality problems, which result in their challenges to be produced or used on a large scale. Furthermore, the existence of a large variety of plastic polymer types has led to an increase in public confusion on the subject of what is recyclable. Plastic consumerism is inevitable and continues to grow. Not only is existing plastic pollution prevalent and ubiquitous, but new plastic waste is generated at an alarming rate. This global excess of plastic waste harms the environment and pollutes the food chain.

A common component of the municipal waste stream and marine debris is contaminated plastics or contaminated plastic waste. Current methods that exist for the treatment of contaminated plastics or contaminated plastic waste include pyrolysis, incineration, landfill disposal, and mechanical recycling after thorough cleaning. Plastic pyrolysis is energy intensive and produces low-grade fuels that require expensive refinery steps to be useful chemicals. This cannot be economically accomplished. Plastic incineration requires massive amounts of upfront capital to establish, needs substantial power and maintenance, and also results in adverse environmental consequences, as does the disposal of plastics in landfills. These expensive methods pollute the environment and do not utilize the contaminated plastic waste materials that could be used as a raw feedstock for new products. Almost all post-consumer and post-industrial contaminated plastic waste are centralized to material recovery facilities, where they can become further contaminated. Mechanical recycling is not economically viable because cleaning contaminated plastics or contaminated plastic waste requires intensive resources and labor.

Less than 15% of global plastics produced is recycled because the process is not economical. As much as 50% of recycling bin content in the United States is considered contamination and is normally discarded by the traditional recycling process. Even though plastics are the most abundant materials in the waste recovery stream, they are the least preferred material for recycling because most plastic, with the exception of water bottles and milk jugs, have few or no viable downstream markets. In 2014, the EPA has calculated the amount of plastic films not recycled was 3.6 million tons. Since then, packaging plastics have increased in volume at waste plants due to the wide adoption of food delivery and online shopping.

Although much research has been done on the bioremediation of plastic pollution, biological methods alone are expensive, inefficient, and difficult to scale. Such techniques, including those involving ex vivo cellular degradation or insect larval digestion, also have not coupled plastic waste treatment with the production of value-added economical products.

Thus, there is a need in the art for methods and systems that provide for the decomposition of contaminated plastic waste that overcome the limitations of known methods.

SUMMARY OF THE INVENTION

The following embodiments and aspects thereof are described and illustrated in conjunction with systems, compositions, methods, and articles of manufacture which are meant to be exemplary and illustrative, not limiting in scope.

In various embodiments, the present invention provides a method for decomposing contaminated plastic waste, comprising: adding contaminated plastic waste to a reaction vessel; adding at least one oxidizing agent to the reaction vessel; and subjecting the contaminated plastic waste to conditions effective to decompose the contaminated plastic waste to produce a decomposition mixture.

In some embodiments, the method further comprises adding at least one solid state catalyst to the reaction vessel.

In some embodiments, the conditions comprise a temperature range; an initial pressure range of a gas; and a residence time in the reaction vessel.

In some embodiments, the contaminated plastic waste comprises at least one plastic material; and at least one non-plastic material.

In some embodiments, the plastic material comprises at least one selected from the group consisting of plastic film, plastic foam, plastic packaging, plastic bags, plastic wrap, and combinations thereof.

In some embodiments, the plastic material comprises polyethylene.

In some embodiments, the plastic material comprises at least one selected from the group consisting of very low density polyethylene, low density polyethylene, linear low density polyethylene, medium density polyethylene, cross-linked polyethylene, high density polyethylene, high density cross-linked polyethylene, high molecular weight polyethylene, ultra-low molecular weight polyethylene, ultra-high molecular weight polyethylene, and combinations thereof.

In some embodiments, the non-plastic material comprises at least one selected from the group consisting of non-plastic organic material, inorganic material, fluid, and combinations thereof.

In some embodiments, the method further comprises separating the decomposition mixture into a solid phase and a liquid phase.

In some embodiments, the solid phase comprises at least one selected from the group consisting of oligomer, polymer, and combinations thereof.

In some embodiments, the solid phase further comprises at least one solid state catalyst.

In some embodiments, the liquid phase comprises at least one compound containing at least one carboxyl group.

In some embodiments, the at least one compound containing at least one carboxyl group is at least one organic acid.

In some embodiments, the method further comprises converting the at least one organic acid into at least one corresponding ester.

In some embodiments, the at least one organic acid is at least one selected from the group consisting of a monocarboxylic acid, dicarboxylic acid, polycarboxylic acid, and combinations thereof.

In some embodiments, the at least one organic acid is an α,ω-dicarboxylic acid.

In some embodiments, the at least one organic acid is selected from the group consisting of succinic acid, glutaric acid, adipic acid, pimelic acid, suberic acid, azelaic acid, sebacic acid, undecanedioic acid, dodecanedioic acid, and combinations thereof.

In some embodiments, the method further comprises separating the at least one organic acid.

In some embodiments, the method further comprises separating the at least one corresponding ester.

In some embodiments, the at least one solid state catalyst is selected from the group consisting of zeolite, alumina, silico-alumino-phosphate, sulfated zirconia, zinc oxide, titanium oxide, zirconium oxide, niobium oxide, iron carbonate, calcium carbide, and combinations thereof.

In some embodiments, the at least one oxidizing agent is selected from the group consisting of from oxygen ($O_2$), nitric oxide (NO), nitrous oxide ($N_2O$), nitrogen dioxide ($NO_2$), nitric acid ($HNO_3$), aqueous nitric acid ($HNO_3$), and combinations thereof.

In some embodiments, the temperature range is from 60° C. to 200° C.

In some embodiments, the gas is at least one selected from the group consisting of air, nitrogen ($N_2$), oxygen ($O_2$), and combinations thereof.

In some embodiments, the initial pressure of the gas is 0 psi to 1000 psi.

In some embodiments, the residence time in the reaction vessel is one selected from the group consisting of 30 minutes to 30 hours, less than 30 minutes, and more than 30 hours.

In some embodiments, the method further comprises feeding the oligomer, the polymer, and combinations thereof back into the reactor.

In some embodiments, the liquid phase further comprises the at least one oxidizing agent.

In some embodiments, the method further comprises collecting and regenerating the at least one oxidizing agent.

In some embodiments, the at least one corresponding ester is selected from the group consisting of dimethyl succinate, dimethyl glutarate, dimethyl adipate, dimethyl pimelate, dimethyl suberate, dimethyl azelate, dimethyl sebacate, dimethyl undecanedioate, dimethyl dodecanedioate, and combinations thereof.

Some embodiments described herein relate to a composition that includes succinic acid, glutaric acid, adipic acid, pimelic acid, and azelaic acid, or the salts or esters thereof, and at least one of oxalic acid, suberic acid, sebacic acid, undecanedioic acid, dodecanedioic acid, tridecanedioic acid, tetradecanedioic acid, pentadecanedioic acid, 2-octenedioic acid, 2-nonenedioic acid, 2-decenedioic acid, and 2-undecenedioic acid, or the salts or esters thereof.

In some embodiments, succinic acid is present in an amount of from about 5 to about 18 wt %, glutaric acid is present in an amount of from about 8 to about 28 wt %, adipic acid is present in an amount of about 10 to about 29 wt %, pimelic acid is present in an amount of about 10 to about 20 wt %, and azelaic acid is present in an amount of about 8 to about 13 wt %, or an equivalent amount of the salts or esters thereof, and if present, oxalic acid is present in an amount up to 10 wt %, if present suberic acid is present in an amount of about 9 to about 20 wt %, if present sebacic acid is present in an amount of about 1 to about 10 wt %, if present undecanedioic acid is present in an amount of about 1 to about 8 wt %, if present dodecanedioic acid is present up to about 5 wt %, if present tridecanedioic acid is present up to about 4 wt %, if present tetradecanedioic acid is present up to about 2 wt %, and if present pentadecanedioic acid is present up to about 0.4 wt %, or an equivalent amount of the salts or esters thereof.

In some embodiments, succinic acid is present in an amount of from about 10 to about 11 wt %, glutaric acid is present in an amount of from about 15 to about 18 wt %, adipic acid is present in an amount of about 16 to about 18 wt %, pimelic acid is present in an amount of about 15 to about 17 wt %, and azelaic acid is present in an amount of about 10 to about 12 wt %, or an equivalent amount of the salts or esters thereof, and if present, oxalic acid is present in an amount up to 10 wt %, if present suberic acid is present in an amount of about 13 to about 15 wt %, if present sebacic acid is present in an amount of about 5 to about 9 wt %, if present undecanedioic acid is present in an amount of about 3 to about 6 wt %, if present dodecanedioic acid is present in an amount of about 1 to about 3 wt %, if present tridecanedioic acid is present in an amount of about 0.5 to about 1.5 wt %, if present tetradecanedioic acid is present up to about 0.2 wt %, and if present pentadecanedioic acid is present up to about 0.2 wt %, or an equivalent amount of the salts or esters thereof.

In some embodiments, succinic acid is present in an amount of from about 5 to about 40 wt %, glutaric acid is present in an amount of from about 8 to about 27 wt %, adipic acid is present in an amount of about 10 to about 29 wt %, pimelic acid is present in an amount of about 10 to about 20 wt %, and azelaic acid is present in an amount of about 1 to about 13 wt %, or an equivalent amount of the salts or esters thereof, and if present, oxalic acid is present in an amount up to 10 wt %, if present suberic acid is present in an amount of to about 4 to about 20 wt %, if present sebacic acid is present up to about 10 wt %, if present undecanedioic acid is present up to about 8 wt %, if present dodecanedioic acid is present up to about 5 wt %, if present tridecanedioic acid is present up to about 4 wt %, if present tetradecanedioic acid is present up to about 2 wt %, and if present pentadecanedioic acid is present up to about 0.4 wt %, or an equivalent amount of the salts or esters thereof.

In some embodiments, the composition may further include at least one of nitro-suberic acid, nitro-azelaic acid, nitro-sebacic acid, nitro-undecanedioic acid, nitro-dodecanedioic acid, nitro-brassylic acid, nitro-tetradecanedioic acid, nitro-pentadecanedioic acid, nitro-hexadecanedioic acid, nitro-heptadecanedioic acid, nitro-octadecanedioic acid, nitro-nonadecanedioic acid, or nitro-icosanedioic acid, or the salts or esters thereof. In some embodiments, the dicarboxylic acid is 2-nitro-suberic acid, 2-nitro-azelaic acid, 2-nitro-sebacic acid, 2-nitro-undecanedioic acid, 2-nitro-dodecanedioic acid, 2-nitro-brassylic acid, 2-nitro-tetradecanedioic acid, 2-nitro-pentadecanedioic acid, 2-nitro-hexadecanedioic acid, 2-nitro-heptadecanedioic acid, 2-nitro-octadecanedioic acid, 2-nitro-nonadecanedioic acid, or 2-nitro-icosanedioic acid, or the salts or esters thereof.

Some embodiments described herein relate to a composition that includes succinic acid, glutaric acid, adipic acid, pimelic acid, and azelaic acid, or the salts or esters thereof, and at least one $C_8$-$C_{20}$ dicarboxylic acid substituted with a single nitro group, or the salts or esters thereof.

In some embodiments, the $C_8$-$C_{20}$ dicarboxylic acid substituted with a single nitro group may be nitro-suberic acid, nitro-azelaic acid, nitro-sebacic acid, nitro-undecanedioic acid, nitro-dodecanedioic acid, nitro-brassylic acid, nitro-tetradecanedioic acid, nitro-pentadecanedioic acid, nitro-hexadecanedioic acid, nitro-heptadecanedioic acid, nitro-octadecanedioic acid, nitro-nonadecanedioic acid, and nitro-icosanedioic acid, or the salts or esters thereof. In some embodiments, the $C_8$-$C_{20}$ dicarboxylic acid is 2-nitro-suberic acid, 2-nitro-azelaic acid, 2-nitro-sebacic acid, 2-nitro-undecanedioic acid, 2-nitro-dodecanedioic acid, 2-nitro-brassylic acid, 2-nitro-tetradecanedioic acid, 2-nitro-pentadecanedioic acid, 2-nitro-hexadecanedioic acid, 2-nitro-heptadecanedioic acid, 2-nitro-octadecanedioic acid, 2-nitro-nonadecanedioic acid, or 2-nitro-icosanedioic acid, or the salts or esters thereof.

In some embodiments, the at least one $C_8$-$C_{20}$ dicarboxylic acid substituted with a single nitro group may be present up to 1 wt % in the composition.

In some embodiments, the composition may further include at least one of oxalic acid, suberic acid, sebacic acid, undecanedioic acid, dodecanedioic acid, tridecanedioic acid, tetradecanedioic acid, pentadecanedioic acid, 2-octenedioic acid, 2-nonenedioic acid, 2-decenedioic acid, and 2-undecenedioic acid, or the salts or esters thereof.

In some embodiments, succinic acid may be present in an amount of from about 5 to about 18 wt %, glutaric acid is present in an amount of from about 8 to about 28 wt %, adipic acid is present in an amount of about 10 to about 29 wt %, pimelic acid is present in an amount of about 10 to about 20 wt %, and azelaic acid is present in an amount of about 8 to about 13 wt %, or an equivalent amount of the salts or esters thereof, and if present, oxalic acid may be present in an amount up to 10 wt %, if present suberic acid is present in an amount of to about 9 to about 20 wt %, if present sebacic acid is present in an amount of about 1 to about 10 wt %, if present undecanedioic acid is present in an amount of about 1 to about 8 wt %, if present dodecanedioic acid is present up to about 5 wt %, if present tridecanedioic acid is present up to about 4 wt %, if present tetradecanedioic acid is present up to about 2 wt %, and if present pentadecanedioic acid is present up to about 0.4 wt %, or an equivalent amount of the salts or esters thereof.

In some embodiments, succinic acid is present in an amount of from about 10 to about 11 wt %, glutaric acid is present in an amount of from about 15 to about 18 wt %, adipic acid is present in an amount of about 16 to about 18 wt %, pimelic acid is present in an amount of about 15 to about 17 wt %, and azelaic acid is present in an amount of about 10 to about 12 wt %, or an equivalent amount of the salts or esters thereof, and if present, oxalic acid is present in an amount up to 10 wt %, if present suberic acid is present in an amount of about 13 to about 15 wt %, if present sebacic acid is present in an amount of about 5 to about 9 wt %, if present undecanedioic acid is present in an amount of about 3 to about 6 wt %, if present dodecanedioic acid is present in an amount of about 1 to about 3 wt %, if present tridecanedioic acid is present in an amount of about 0.5 to about 1.5 wt %, if present tetradecanedioic acid is present up to about 0.2 wt %, and if present pentadecanedioic acid is present up to about 0.2 wt %, or an equivalent amount of the salts or esters thereof.

In some embodiments, succinic acid is present in an amount of from about 5 to about 40 wt %, glutaric acid is present in an amount of from about 8 to about 27 wt %, adipic acid is present in an amount of about 10 to about 29 wt %, pimelic acid is present in an amount of about 10 to about 20 wt %, and azelaic acid is present in an amount of about 1 to about 13 wt %, or an equivalent amount of the salts or esters thereof, and if present, oxalic acid is present in an amount up to 10 wt %, if present suberic acid is present in an amount of to about 4 to about 20 wt %, if present sebacic acid is present up to about 10 wt %, if present undecanedioic acid is present up to about 8 wt %, if present dodecanedioic acid is present up to about 5 wt %, if present tridecanedioic acid is present up to about 4 wt %, if present tetradecanedioic acid is present up to about 2 wt %, and if present pentadecanedioic acid is present up to about 0.4 wt %, or an equivalent amount of the salts or esters thereof.

In some embodiments, the acids may be at least partially in the form of an alkaline metal salt.

In some embodiments, the acids may be at least partially in the form of esters.

In some embodiments, the esters may be $C_{1-4}$ alkyl esters

In some embodiments, the acids may be in the form of free acids.

Some embodiments described herein relate to a method for decomposing plastic waste that includes a. adding plastic waste to a reaction vessel, b. adding aqueous nitric acid ($HNO_3$) to the reaction vessel to give a mixture, wherein the wt. ratio of plastic waste to aqueous nitric acid is greater than 1:3, c. subjecting the mixture obtained in b. to conditions effective to decompose the plastic waste to produce decomposition products, wherein the decomposition products include succinic acid, glutaric acid, adipic acid, pimelic acid, and azelaic acid, and at least one of oxalic acid, suberic acid, sebacic acid, undecanedioic acid, dodecanedioic acid, tridecanedioic acid, tetradecanedioic acid, pentadecanedioic acid, 2-octenedioic acid, 2-nonenedioic acid, 2-decenedioic acid, and 2-undecenedioic acid.

Some embodiments described herein relate to a method for decomposing plastic waste, that includes a. adding plastic waste to a reaction vessel, b. adding aqueous nitric acid ($HNO_3$) to the reaction vessel to give a mixture, wherein the wt. ratio of plastic waste to aqueous nitric acid is greater than 1:3, c. subjecting the mixture obtained in b. to conditions effective to decompose the plastic waste to produce decomposition products, wherein the decomposition products include succinic acid, glutaric acid, adipic acid, pimelic acid, and azelaic acid, and at least one of $C_8$-$C_{20}$ dicarboxylic acid substituted with a single nitro group, or the salts or esters thereof.

In some embodiments, the at least one $C_8$-$C_{20}$ dicarboxylic acid substituted with a single nitro group may be nitro-suberic acid, nitro-azelaic acid, nitro-sebacic acid, nitro-undecanedioic acid, nitro-dodecanedioic acid, nitro-brassylic acid, nitro-tetradecanedioic acid, nitro-pentadecanedioic acid, nitro-hexadecanedioic acid, nitro-heptadecanedioic acid, nitro-octadecanedioic acid, nitro-nonadecanedioic acid, or nitro-icosanedioic acid, or the salts or esters thereof. In some embodiments, the $C_8$-$C_{20}$ dicarboxylic acid is 2-nitro-suberic acid, 2-nitro-azelaic acid, 2-nitro-sebacic acid, 2-nitro-undecanedioic acid, 2-nitro-dodecanedioic acid, 2-nitro-brassylic acid, 2-nitro-tetradecanedioic acid, 2-nitro-pentadecanedioic acid, 2-nitro-hexadecanedioic acid, 2-nitro-heptadecanedioic acid, 2-nitrooctadecanedioic acid, 2-nitro-nonadecanedioic acid, or 2-nitro-icosanedioic acid, or the salts or esters thereof.

In some embodiments, the at least one $C_8$-$C_{20}$ dicarboxylic acid substituted with a single nitro group may be present up to 1 wt % in the composition.

In some embodiments, the plastic waste may include polyethylene.

In some embodiments, the plastic waste further includes at least one non-plastic waste.

In some embodiments, the nitric acid may have a concentration of 10-90 wt %.

In some embodiments, the nitric acid may have a concentration of about 67 to about 70 wt %.

In some embodiments, the weight ratio of plastic waste to nitric acid may be 1:10 to 1:100.

In some embodiments, the method for decomposing plastic waste may further include adding at least one solid state catalyst to the reaction vessel.

In some embodiments, the at least one solid state catalyst may be a zeolite, alumina, silico-alumino-phosphate, sulfated zirconia, zinc oxide, titanium oxide, zirconium oxide, niobium oxide, iron carbonate, calcium carbide, or combinations thereof.

In some embodiments, the conditions effective may include a temperature range of about 60° C. to about 200° C.

In some embodiments, the conditions effective may include a batch process with a residence time in the reaction vessel of about 1 hour to about 10 hours.

In some embodiments, the conditions effective may include a batch process with a residence time in the reaction vessel of about 3 hours to about 6 hours.

In some embodiments, the conditions effective may include a continuous process.

In some embodiments, the continuous process may include the continuous addition of plastic waste and aqueous nitric acid to the reaction vessel and the continuous removal of decomposition products. In some embodiments, the plastic waste and aqueous nitric acid are continuously added to the reaction vessel through a screw conveyor. In some embodiments, the decomposition products are continuously removed from the reaction vessel through a screw conveyor.

In some embodiments, the decomposition products include succinic acid that is present in an amount of from about 5 to about 18 wt %, glutaric acid that is present in an amount of from about 8 to about 28 wt %, adipic acid that is present in an amount of about 10 to about 29 wt %, pimelic acid that is present in an amount of about 10 to about 20 wt %, and azelaic acid that is present in an amount of about 8 to about 13 wt %, and if present, oxalic acid is present in an amount up to 10 wt %, if present suberic acid is present in an amount of about 9 to about 20 wt %, if present sebacic acid is present in an amount of about 1 to about 10 wt %, if present undecanedioic acid is present in an amount of about 1 to about 8 wt %, if present dodecanedioic acid is present up to about 5 wt %, if present tridecanedioic acid is present up to about 4 wt %, if present tetradecanedioic acid is present up to about 2 wt %, and if present pentadecanedioic acid is present up to about 0.4 wt %.

In some embodiments, the decomposition produces may include succinic acid that is present in an amount of from about 10 to about 11 wt %, glutaric acid that is present in an amount of from about 15 to about 18 wt %, adipic acid that is present in an amount of about 16 to about 18 wt %, pimelic acid that is present in an amount of about 15 to about 17 wt %, and azelaic acid that is present in an amount of about 10 to about 12 wt %, and if present, oxalic acid is present in an amount up to 10 wt %, if present suberic acid is present in an amount of about 13 to about 15 wt %, if present sebacic acid is present in an amount of about 5 to about 9 wt %, if present undecanedioic acid is present in an amount of about 3 to about 6 wt %, if present dodecanedioic acid is present in an amount of 1-3 wt %, if present tridecanedioic acid is present in an amount of about 0.5 to about 1.5 wt %, if present tetradecanedioic acid is present up to about 0.2 wt %, and if present pentadecanedioic acid is present up to about 0.2 wt %.

In some embodiments, succinic acid is present in an amount of from about 5 to about 40 wt %, glutaric acid is present in an amount of from about 8 to about 27 wt %, adipic acid is present in an amount of about 10 to about 29 wt %, pimelic acid is present in an amount of about 10 to about 20 wt %, and azelaic acid is present in an amount of about 1 to about 13 wt %, or an equivalent amount of the salts or esters thereof, and if present, oxalic acid is present in an amount up to 10 wt %, if present suberic acid is present in an amount of to about 4 to about 20 wt %, if present sebacic acid is present up to about 10 wt %, if present undecanedioic acid is present up to about 8 wt %, if present dodecanedioic acid is present up to about 5 wt %, if present tridecanedioic acid is present up to about 4 wt %, if present tetradecanedioic acid is present up to about 2 wt %, and if present pentadecanedioic acid is present up to about 0.4 wt %, or an equivalent amount of the salts or esters thereof.

In some embodiments, the conditions effective further include the presence of a zeolite catalyst.

In some embodiments, the method further includes isolating the decomposition products. In some embodiments, the decomposition products may be isolated by removal of insoluble products. In some embodiments, the removal of insoluble products is by filtration.

In some embodiments, the method may further include evaporation of solvent. In some embodiments, the solvent may include nitric acid.

Some embodiments described herein relate to a method for the decomposition of polyethylene, that includes reacting polyethylene with an oxidizing agent in a reactor to produce a reaction product and a reaction gas, supplying the reaction gas to an absorption unit for recovering the oxidizing agent from the reaction gas, and recycling the oxidizing agent from the absorption unit to the reactor.

In some embodiments, the oxidizing agent may be nitric acid.

In some embodiments, the reaction product may include a dicarboxylic acid.

In some embodiments, the reaction product may include succinic acid, glutaric acid, adipic acid, pimelic acid, and azelaic acid, or the salts or esters thereof, and at least one of oxalic acid, suberic acid, sebacic acid, undecanedioic acid, dodecanedioic acid, tridecanedioic acid, tetradecanedioic acid, pentadecanedioic acid, 2-octenedioic acid, 2-nonenedioic acid, 2-decenedioic acid, and 2-undecenedioic acid, or the salts or esters thereof.

In some embodiments, the reaction product may include at least one of 2-nitro-suberic acid, 2-nitro-azelaic acid, 2-nitro-sebacic acid, 2-nitro-undecanedioic acid, 2-nitro-dodecanedioic acid, 2-nitro-brassylic acid, 2-nitro-tetradecanedioic acid, 2-nitro-pentadecanedioic acid, 2-nitro-hexadecanedioic acid 2-nitro-heptadecanedioic acid, 2-nitro-octadecanedioic acid, 2-nitro-nonadecanedioic acid, and 2-nitro-icosanedioic acid, or the salts or esters thereof.

In some embodiments, the reaction product may include succinic acid, glutaric acid, adipic acid, pimelic acid, and azelaic acid, and at least one of $C_8$-$C_{20}$ dicarboxylic acid substituted with a single nitro group, or the salts or esters thereof.

In some embodiments, the $C_8$-$C_{20}$ dicarboxylic acid substituted with a single nitro group may be nitro-suberic acid, nitro-azelaic acid, nitro-sebacic acid, nitro-undecanedioic acid, nitro-dodecanedioic acid, nitro-brassylic acid, nitro-tetradecanedioic acid, nitro-pentadecanedioic acid, nitro-hexadecanedioic acid, nitro-heptadecanedioic acid, nitro-octadecanedioic acid, nitro-nonadecanedioic acid, or nitro-icosanedioic acid, or the salts or esters thereof. In some embodiments, the $C_8$-$C_{20}$ dicarboxylic acid is 2-nitro-suberic acid, 2-nitro-azelaic acid, 2-nitro-sebacic acid, 2-nitro-undecanedioic acid, 2-nitro-dodecanedioic acid, 2-nitro-brassylic acid, 2-nitro-tetradecanedioic acid, 2-nitro-pentadecanedioic acid, 2-nitro-hexadecanedioic acid, 2-nitro-heptadecanedioic acid, 2-nitro-octadecanedioic acid, 2-nitro-nonadecanedioic acid, or 2-nitro-icosanedioic acid, or the salts or esters thereof.

In some embodiments, the method may further include reacting polyethylene and the oxidizing agent with a catalyst selected from the group consisting of hydrochloric acid, hydrobromic acid, zinc oxide, titanium oxide, zirconium oxide, niobium oxide, zeolite, alumina, silico-alumino-phosphate, iron carbonate, calcium carbide, sulfated zirconia, and combinations thereof.

In some embodiments, the method may further include separating the reaction product from the oxidizing agent in a separation unit. In some embodiments, the method may further include recycling the oxidizing agent recovered from the separation unit to the reactor. In some embodiments, the method may further include concentrating the oxidizing agent recovered from the separation unit prior to recycling the oxidizing agent to the reactor.

In some embodiments, the method may further include mixing the reaction gas with air, enriched air, or oxygen prior to supplying the reaction gas to the absorption unit.

In some embodiments, the polyethylene and the oxidizing agent may be reacted at a temperature of about 60° C. to about 200° C. in the reactor.

In some embodiments, a ratio of the mass of polyethylene to the mass of oxidizing agent in the reactor may be 1:3 to 1:100. In some embodiments, the ratio of the mass of polyethylene to the mass of oxidizing agent in the reactor may be 1:10 to 1:100.

Some embodiments described herein relate to a system for the decomposition of polyethylene that includes a reactor configured to carry out a reaction of polyethylene with an oxidizing agent to produce a reaction product and a reaction gas, an absorption unit configured to recover the oxidizing agent from the reaction gas, and return the oxidizing agent to the reactor, and a separation unit configured to separate the reaction product from the oxidizing agent.

In some embodiments, the separation unit may include an evaporator. In some embodiments, the evaporator may be a wiped-film evaporator, a falling-film evaporator, a forced-circulation evaporator, or a flash evaporator.

In some embodiments, the separation unit may further include an oxidizing agent harvester.

In some embodiments, the oxidizing agent harvester may be selected from the group of a chromatography column, a crystallizer, a liquid-liquid extractor, and a Nutsche filter dryer.

In some embodiments, the separation unit may further include a dryer.

In some embodiments, the reactor may include a stirred tank reactor.

In some embodiments, the reactor may include a chopping blade configured to blend and breakdown the polyethylene.

In some embodiments, the reactor may include a screw conveyor configured to convey the polyethylene into or through the reactor.

In some embodiments, the separation unit may be configured to recycle the separated oxidizing agent to the reactor.

In some embodiments, the system may further include a distillation unit configured to concentrate the oxidizing agent prior to recycling the oxidizing agent to the reactor from the absorption unit.

In some embodiments, the system may further include a condenser for condensing the reaction gas from the reactor.

BRIEF DESCRIPTION OF THE DRAWINGS

Exemplary embodiments are illustrated in referenced figures. It is intended that the embodiments and figures disclosed herein are to be considered illustrative rather than restrictive.

FIGS. 22A, B, and C depict, in accordance with various embodiments of the invention, a table showing the various dicarboxylic acids detected by liquid chromatography mass spectrometry (LCMS) in a reaction product.

DETAILED DESCRIPTION OF THE INVENTION

Figure 1:
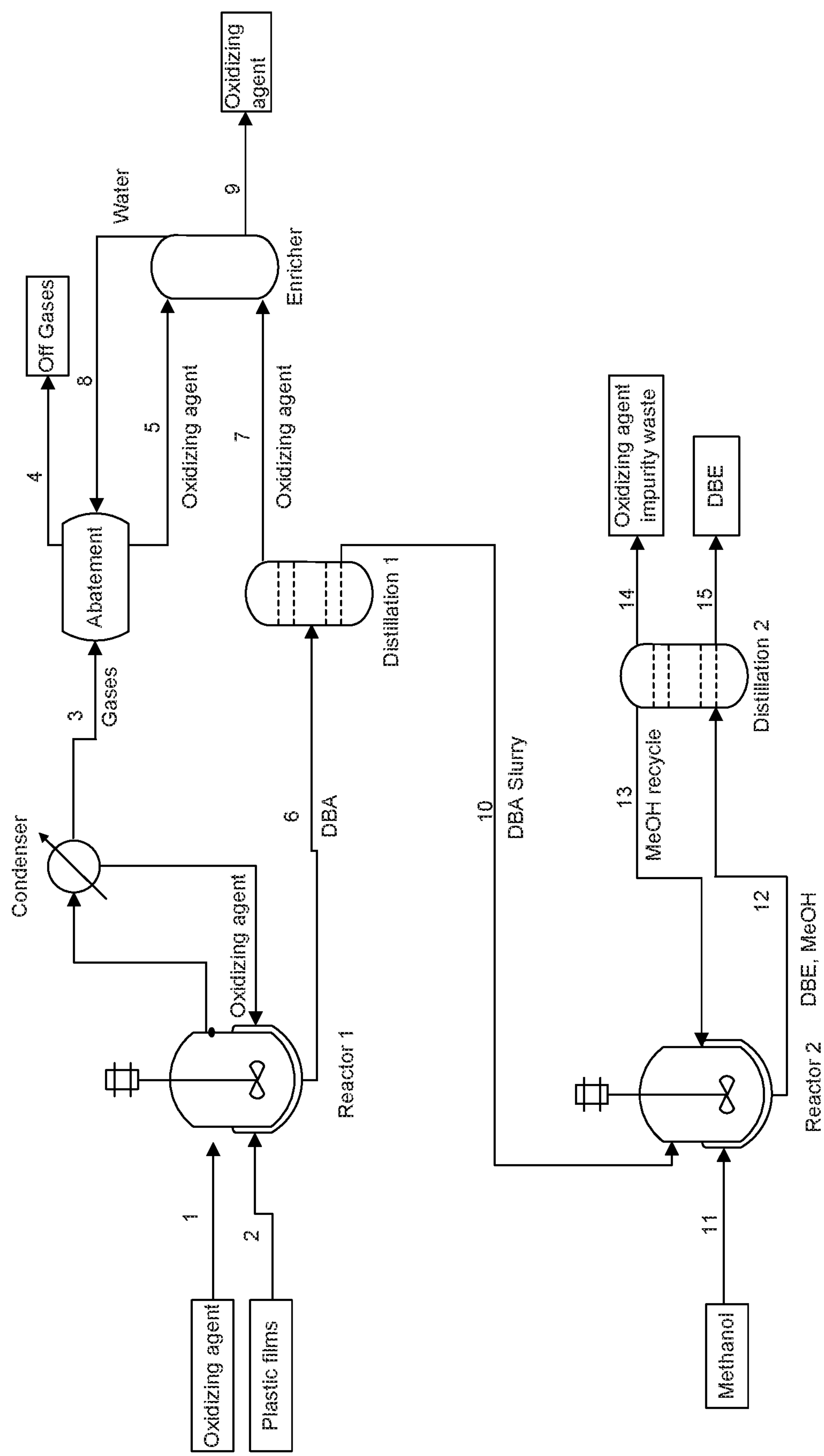
FIG. 1 depicts, in accordance with various embodiments of the invention, a schematic diagram of a reactor system of the present invention for the decomposition of contaminated plastic waste.

All references cited herein are incorporated by reference in their entirety as though fully set forth. Unless otherwise defined, all technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, systems, articles of manufacture, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). As used herein, the term "comprising" or "comprises" means that other elements can also be present in addition to the defined elements presented. The use of "comprising" indicates inclusion rather than limitation. Although the open-ended term "comprising" as a synonym of terms such as including, containing, or having, is used herein to describe and claim the invention, the present invention, or embodiments thereof, may alternatively be described using alternative terms such as "consisting of" or "consisting essentially of".

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

Groupings of alternative elements or embodiments of the present invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

"Optional" or "optionally" means that the subsequently described circumstance may or may not occur, so that the description includes instances where the circumstance occurs and instances where it does not.

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amidine, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls including ketones, carboxy, carboxylates, $CF_3$, cyano (CN), cycloalkyl, cycloalkylene, ester, ether, haloalkyl, halogen, halogen, heteroaryl, heterocyclyl, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring. In some cases, two or more substituents, together with the carbon(s) to which they are attached to, can form one or more rings.

Substituents may be protected as necessary and any of the protecting groups commonly used in the art may be employed. Non-limiting examples of protecting groups may be found, for example, in Greene and Wuts, Protective Groups in Organic Synthesis, $44^{th}$. Ed., Wiley & Sons, 2006.

The term "carboxy" means the radical —C(O)O—. It is noted that compounds described herein containing carboxy moiety can include protected derivatives thereof, i.e., where the oxygen is substituted with a protecting group. Suitable protecting groups for carboxy moieties include benzyl, tert-butyl, methyl, ethyl, and the like. The term "carboxyl" means —COOH.

The term "polymer" means a substance, chemical compound or mixture of compounds, that has a molecular structure consisting chiefly or entirely of a large number of similar units (e.g., monomer units) bonded together. Of which, linear polymer is also called straight-chain because it consists of a long string of carbon-carbon bonds; branching polymer has branches at irregular intervals along the polymer chain; cross linking polymer contains branches that connect polymer chains, via covalent, ionic, or H-bonding; optionally substituted polymer is a polymer that contains functionality at random points along the hydrocarbon chain backbone where one or more of the hydrogen atoms linked to the chain backbone may be, but are not required to be substituted with a substituent independently selected from the group of substituents provided herein in the definition for "substituents" or otherwise specified. Such polymers are said to be optionally substituted because they generally do not exhibit a regular substitution pattern along the chain backbone; addition polymer is formed by adding monomers to a growing polymer chain; condensation polymer is formed when a small molecule condenses out during the polymerization reaction; homopolymer is formed by polymerizing a single monomer; copolymer is formed by polymerizing more than one monomer; synthetic polymer is synthesized through chemical reactions; natural polymer is originated in nature and can be extracted; biopolymer is produced by living organisms, modified or natural; organic polymers are polymers that contain carbon atoms in the backbone of the polymer chain.

The term "oligomer" means a substance, chemical compound or mixture of compounds that has a molecular structure consisting chiefly or entirely of a few number of similar units (e.g., monomer units) bonded together.

The term "plastic" means a synthetic material comprising a wide range of organic polymers such as polyolefins, polyesters, polyamides, etc., that can be molded into shape while soft and then set into a rigid, semi-elastic, or elastic form.

The term "about" means the recited number ±10%. For example, "about 100" means 90-110, inclusive.

Various Non-Limiting Embodiments of the Invention

It is an object of the present invention to provide methods and systems that provide for the decomposition of contaminated plastic waste that overcome the limitations of known methods and systems.

Referring to FIG. 1, a reactor system for decomposing contaminated waste plastic according to embodiments of the present invention are illustrated, where like numerals represent like parts.

Referring to FIG. 1, at least one oxidizing agent (1) and contaminated plastic waste (2) enter Reactor 1, which is then heated to the desired temperature. During the reaction, the contents are agitated or stirred, and the vapors are condensed back as liquid. Gases (3) that escape through the condenser are channeled into an Abatement system (8) to regenerate the oxidizing agent (5). Other off gases (4) are scrubbed. The aqueous product stream (6), carrying dibasic acids, enters Distillation 1, where the oxidizing agent is distilled and collected in the Enricher. The oxidizing agent (5) and the oxidizing agent (7) are combined into the Enricher, which adjusts the oxidizing agent (9) to the desired starting concentration. Close to the end of the distillation, a slurry (10) of dibasic acids and residual oxidizing agent are transferred into Reactor 2, where methanol (11) is added for the esterification. The product stream (12), carrying dibasic esters, excess methanol, and residual oxidizing agent, enters Distillation 2, where the three types of outputs (13, 14, 15) are separated. In some embodiments the reactor system shown in FIG. 1 can be modified to accommodate batch, continuous, substantially continuous and/or semi-continuous processes.

Other useful flow schemes are contemplated via various embodiments of the present invention.

In various embodiments, equipment that may be used in the methods (processes) and/or systems described herein includes conventional reactors, piping, etc. The equipment are amenable and economical for use in process plants that can be either large or small.

In various embodiments, the present invention provides a method for decomposing contaminated plastic waste, comprising: adding contaminated plastic waste to a first reaction vessel; adding at least one oxidizing agent to the first reaction vessel; subjecting the contaminated plastic waste to conditions effective to decompose the contaminated plastic waste to produce a decomposition mixture in the first reaction vessel. In some embodiments, the method further comprises producing at least one first off-gas. In some embodiments, the method further comprises collecting and regenerating the oxidizing agent. In some embodiments, the method further comprises transferring the decomposition mixture to a first distillation unit. In some embodiments, the method further comprises removing at least a portion of the oxidizing agent from the decomposition mixture to form a decomposition slurry. In some embodiments, the decomposition slurry comprises at least one compound containing at least one carboxyl group; and at least one residual oxidizing agent. In some embodiments, the at least one compound containing at least one carboxyl group is at least one organic acid. In some embodiments, the method further comprises transferring the decomposition slurry to a second reaction vessel. In some embodiments, the method further comprises adding at least one alcohol to the second reaction vessel to form an esterification reaction mixture; and subjecting the esterification reaction mixture to conditions effective to form an esterification product mixture. In some embodiments, the esterification product mixture comprises at least one residual oxidizing agent, at least one alcohol, and at least one ester. In some embodiments, the method further comprises transferring the esterification product mixture to a second distillation unit. In some embodiments, the method further comprises separating the esterification product mixture in the second distillation unit into a residual oxidizing agent waste stream, an ester stream, and an alcohol stream. In some embodiments, the ester stream comprises at least one organic acid in at least one ester form. In some embodiments, the method further comprises adding at least one solid state catalyst to the first reaction vessel. In some embodiments, the method comprises optionally adding at least one solid state catalyst to the first reaction vessel. In some embodiments, the method may include adding at least one solid state catalyst to the first reaction vessel.

In various embodiments, the present invention provides a method for decomposing contaminated plastic waste, comprising: adding contaminated plastic waste to a reaction vessel; adding at least one oxidizing agent to the reaction vessel; and subjecting the contaminated plastic waste to conditions effective to decompose the contaminated plastic waste to produce a decomposition mixture. In some embodiments, the method further comprises adding at least one solid state catalyst to the reaction vessel. In some embodiments, the method comprises optionally adding at least one solid state catalyst to the reaction vessel. In some embodiments, the method may include adding at least one solid state catalyst to the reaction vessel. In some embodiments, the conditions comprise a temperature range; an initial pressure range of a gas; and a residence time in the reaction vessel.

In various embodiments, the present invention provides a method for decomposing contaminated plastic waste, comprising: adding contaminated plastic waste to a reaction vessel; adding at least one oxidizing agent to the reaction vessel; optionally adding at least one solid state catalyst to the reaction vessel; and subjecting the contaminated plastic waste to conditions effective to decompose the contaminated plastic waste to produce a decomposition mixture. In some embodiments, the conditions comprise a temperature range; an initial pressure range of a gas; and a residence time in the reaction vessel.

In various embodiments, the present invention provides a method for decomposing contaminated plastic waste, comprising: adding contaminated plastic waste to a reaction vessel; adding at least one oxidizing agent to the reaction vessel; optionally adding at least one solid state catalyst to the reaction vessel; and subjecting the contaminated plastic waste to conditions effective to decompose the contaminated plastic waste to produce a decomposition mixture, wherein the conditions comprise: a temperature range; an initial pressure range of a gas; and a residence time in the reaction vessel.

In some embodiments, the method is selected from the group consisting of a batch process, continuous process, substantially continuous process, and semi-continuous process.

In some embodiments, the present invention provides a system for decomposing contaminated plastic waste, comprising: a first reaction vessel; a condenser; an abatement unit; an enricher unit; a first distillation unit; a second reaction vessel; and a second distillation unit; wherein the first reaction vessel is connected to the condenser and to the first distillation unit; the condenser is connected to the abatement unit and to the first reaction vessel; the abatement unit is connected to the enricher unit; the enricher unit is connected to the abatement unit; the first distillation unit is connected to the enricher unit and to the second reaction vessel; the second reaction vessel is connected to the second distillation unit; and the second distillation unit is connected to the second reaction vessel.

Reaction Vessel

Non-limiting examples of a reaction vessel (e.g., reactors, glass lined reactors, glass flasks, containers and the like in which the methods and/or processes of the present invention are performed) suitable for use in a processes and/or methods of the invention are generally closed (not open to the surrounding atmosphere) and, optionally, pressurizable reactors; non-limiting types of closed, pressurizable reactors suitable for, in particular, batch processes, continuous processes, substantially continuous processes, or semi-continuous processes according to the invention include reactors and autoclaves from Parr Instrument Company, Amar Equipments, Buchiglas, and Berghof. In some embodiments, the reaction vessel is pressurized. In some embodiments, the reaction vessel is not pressurized.

In some embodiments, the reaction vessel is at least one selected from the group consisting of reactor, glass flask, glass lined reactor, and combinations thereof.

In some embodiments relevant types of reaction vessels for performing batch processes or continuous processes, substantially continuous processes, or semi-continuous processes include substantially vertically disposed reaction vessels in which the contaminated plastic waste and any additional reagents/materials (e.g. gases, liquids, solids) in question may be contained and into which gases may be introduced-continuously or at intervals-under pressure or at ambient pressure via one or more inlets, ports, valves or the like situated at or near the bottom of, and/or at other locations along the length of, the reaction vessel; such reaction vessels, which may suitably, but optionally, have an upper headspace or free volume, may be essentially cylindrical, tubular or of any other appropriate form. In some embodiments, reaction vessels for performing batch processes or continuous processes, substantially continuous processes, or semi-continuous processes include substantially horizontally disposed reactors.

In batch processes, continuous processes, substantially continuous processes, or semi-continuous processes it is generally desirable, where possible, to cause mixing of the contaminated plastic waste and any additional reagents/materials (e.g. gases, liquids, solids) and any solid phase and any liquid phase and any gas phase which may be present in the reaction vessel. In some embodiments mixing may suitably be achieved by mechanical stirring, although agitation of the reaction vessel as a whole or other means of causing mixing may be applicable. In some embodiments, mixing may be suitably achieved by recirculation by means of a pump, impeller wheel, rotating scraper, or the like.

Heat may be supplied to the reaction mixture and/or reaction system (e.g., the contaminated plastic waste and any additional reagents/materials (e.g. gases, liquids, solids) and any solid phase and any liquid phase and any gas phase which may be present in the reactor) by any suitable method. Non-limiting examples include immersing the reaction vessel in an appropriate heating bath (comprising, e, g., an oil, a molten salt or molten salt mixture, superheated steam, etc.); by means of thermally conductive (typically metal) tubing which is wound around the outside of the reaction vessel, and/or is immersed in the reaction medium itself, and through which suitably hot oil, superheated steam or the like is passed; or—similarly—by means of one or more electrical resistance heating elements wound around the outside of the reaction vessel and/or immersed in the reaction medium; by a heating mantle; or by means of a jacketed reactor as known in the art. Other applicable methods of heating include induction heating (e. g. of a metal reactor casing) and microwave heating.

In some embodiments, the reaction is carried out in a batch process. In other embodiments, the reaction is carried out in a continuous process.

In a batch process, in some embodiments, oxidizing agent (e.g., nitric acid) is added to the reactor before heating and stirring begins. As the reactor reaches the desired temperature, the plastic (e.g., polyethylene) is added and the reaction is allowed to proceed with stirring for the desired time. In some embodiments, the oxidizing agent (e.g., nitric oxide) is refluxed in the reaction vessel using a condenser during the process. After the reaction is complete, the reactor is left to cool and the reaction mixture (comprising liquid and solid streams), are filtered, e.g., through filter paper, a sieve, Buchner funnel or the like. The solid stream comprises unreacted or incompletely reacted plastic. The liquid stream comprises dilute nitric acid, dissolved dicarboxylic acids and other compounds such as nitro-substituted dicarboxylic acids. In some embodiments, the liquid stream is then heated and the oxidizing agent (e.g., nitric acid) and water are separated from the dicarboxylic acids by distillation.

In a continuous process, in some embodiments, the initial desired amount of oxidizing agent (e.g., nitric acid) is added to the reactor before heating a stirring begins. As the reactor reaches the desired temperature, the plastic (e.g., polyethylene) is added. The reaction vessel exit valve is then opened and adjusted so that the amount of product exiting the reaction vessel is at a constant flow rate that is about the same as the amounts of plastic and oxidizing agent being added to the reaction vessel, thus maintaining about a constant amount of reactants and products in the reaction vessel during the process. In some embodiments, the oxidizing agent (e.g., nitric acid) is refluxed in the reaction vessel using a condenser during the process. In some embodiments, samples are taking at time intervals, cooled, and filtered, e.g., through filter paper, with a sieve, Buchner funnel or the like. The liquid stream comprises dilute nitric acid, dissolved dicarboxylic acids and other compounds such as nitro-substituted dicarboxylic acids. In some embodiments, the liquid stream is then heated and the oxidizing agent (e.g., nitric acid) and water are separated from the dicarboxylic acids by distillation.

Temperature Range

In some embodiments, the temperature range is from 60° C. to 200° C. In some embodiments, the temperature range in the reaction vessel is from 60° C. to 200° C. In some embodiments, the reaction vessel is the first reaction vessel.

In some embodiments, the temperature range is from 60° C. to 200° C., 60° C. to 175° C., 60° C. to 150° C., 60° C. to 125° C., 60° C. to 100° C., 60° C. to 90° C., 60° C. to 80° C., or 60° C. to 70° C.

In some embodiments, the temperature range is from 60° C. to 200° C., 70° C. to 200° C., 80° C. to 200° C., 90° C. to 200° C., 100° C. to 200° C., 100° C. to 200° C., 120° C. to 200° C., 130° C. to 200° C., 140° C. to 200° C., 150° C. to 200° C., 160° C. to 200° C., 170° C. to 200° C., 180° C. to 200° C., or 190° C. to 200° C.

Initial Pressure Range of a Gas

In some embodiments, the initial pressure of the gas is 0 psi to 1000 psi. In some embodiments, the initial pressure of the gas in the reaction vessel is 0 psi to 1000 psi. In some embodiments, the reaction vessel is the first reaction vessel.

In some embodiments, the initial pressure of the gas is 0 psi to 900 psi, 0 psi to 800 psi, 0 psi to 700 psi, 0 psi to 600 psi, 0 psi to 500 psi, 0 psi to 400 psi, 0 psi to 300 psi, 0 psi to 200 psi, or 0 psi to 100 psi.

Residence Time in the Reaction Vessel

In some embodiments, the residence time in the reaction vessel is one selected from the group consisting of 30 minutes to 30 hours, less than 30 minutes, and more than 30 hours. In some embodiments, the reaction vessel is the first reaction vessel.

In some embodiments the residence time in the reaction vessel is 30 minutes to 30 hours, 30 minutes to 29 hours, 30 minutes to 28 hours, 30 minutes to 27 hours, 30 minutes to 26 hours, 30 minutes to 25 hours, 30 minutes to 24 hours, 30 minutes to 23 hours, 30 minutes to 22 hours, 30 minutes to 21 hours, 30 minutes to 20 hours, 30 minutes to 19 hours, 30 minutes to 18 hours, 30 minutes to 17 hours, 30 minutes to 16 hours, 30 minutes to 15 hours, 30 minutes to 14 hours, 30 minutes to 13 hours, 30 minutes to 12 hours, 30 minutes to 11 hours, 30 minutes to 10 hours, 30 minutes to 9 hours, 30 minutes to 8 hours, 30 minutes to 7 hours, 30 minutes to 6 hours, 30 minutes to 5 hours, 30 minutes to 4 hours, 30 minutes to 3 hours, 30 minutes to 2 hours, or 30 minutes to 1 hour.

In some embodiments, the residence time in the reaction vessel is 30 minutes, 25 minutes, 20 minutes, 15 minutes, 10 minutes, or 5 minutes.

In some embodiments, the residence time in the reaction vessel is 30 hours, 35 hours, 40 hours, 45 hours, 50 hours, 55 hours, 60 hours, 65 hours, 70 hours, or 75 hours. In some embodiments, the residence time in the reaction vessel is about 1 hour to about 10 hours. In some embodiments, the residence time in the reaction vessel is about 3 hours to about 6 hours.

In some embodiments, the reaction vessel for a batch process is Reactor 1 (e.g., Reactor 1 as identified in FIG. 1). In some embodiments, the reaction vessel is a first reaction vessel. In some embodiments, the reaction vessel is Reactor 2 (e.g., Reactor 2 as identified in FIG. 1). In some embodiments, the reaction vessel is a second reaction vessel.

Effects of Time, Temperature, Pressure and Concentration

Different products and amounts of products are obtained depending on the time, temperature and pressure of the reaction. In general, more longer chain dicarboxylic acids are obtained at shorter reaction times and less longer chain dicarboxylic acids are obtained at longer reaction times. Higher amounts of oxalic acid are obtained at shorter reaction times and lower reaction temperatures (e.g., at 100° C. vs. 110° C. vs. 120° C.). Mild reaction conditions give oxalic acid as the main reaction product. Oxalic acid is the major product at 100° C. with reaction times of less than 6 h. Oxalic acid is produced in large amounts with short reaction times, even with elevated temperatures. See, the Examples.

Different products and amounts of products are also obtained depending on the concentration of nitric acid and the ratio of polyethylene to nitric acid. For example, when 70 wt % aqueous nitric acid is used as the solvent, the product is enriched with $C_4$-$C_9$ dicarboxylic acids. With 50 and 60 wt % aqueous nitric acid, the reactions are significantly slower and the product comprises more oxalic acid and significantly higher amounts of $C_{10}$-$C_{15}$ dicarboxylic acids. A higher ratio of nitric acid to polyethylene gives higher amounts of $C_4$-$C_9$ dicarboxylic acids and lower amounts of oxalic acid and longer chain dicarboxylic acids. The higher the concentration of nitric acid, the faster the reaction. The faster the reaction, the more the long chain dicarboxylic acids are broken down into $C_4$-$C_9$ dicarboxylic acids. The amount of oxalic acid decreases with longer reaction time and harsher conditions. See, the Examples.

Different products and amounts of products are also obtained depending on the pressure of the reaction. At lower nitric acid concentrations and higher pressure, a higher yield of dicarboxylic acids is obtained and compared to reactions conducted at atmospheric pressure and higher nitric acid concentrations. For example, 70 wt % aqueous nitric acid, 1:10 polyethylene to nitric acid weight ratio, 6 hour reaction time, 150° C., and atmospheric pressure gave a 29% dicarboxylic acid yield, while 25 wt % aqueous nitric acid, 1:10 polyethylene to nitric acid weight ratio, 6 hour reaction time, 150° C., and 500 psi pressure gave a 42% dicarboxylic acid yield, with notably higher amounts of shorter chain dicarboxylic acids. See, the Examples.

Oxidizing Agent

In some embodiments, the at least one oxidizing agent is selected from the group consisting of oxygen ($O_2$), nitric oxide (NO), nitrous oxide ($N_2O$), nitrogen dioxide ($NO_2$), nitric acid ($HNO_3$), aqueous nitric acid ($HNO_3$), and combinations thereof.

In some embodiments, the aqueous nitric acid has a concentration of 10%-100% by weight, 10%-90% by weight, 10%-80% by weight, 10%-70% by weight, 10%-60% by weight, 10%-50% by weight, 10%-40% by weight, 10%-30% by weight, or 10%-20% by weight.

In some embodiments, the aqueous nitric acid has a concentration of 10%-100% by weight, 20%-100% by weight, 30%-100% by weight, 40%-100% by weight, 50%-100% by weight, 60%-100% by weight, 70%-100% by weight, 80%-100% by weight, or 90%-100% by weight. In some embodiments, the aqueous nitric acid has a concentration of about 67 to about 70% by weight.

Solid State Catalyst

In some embodiments, the at least one solid state catalyst is selected from the group consisting of zeolite, alumina, silico-alumino-phosphate, sulfated zirconia, zinc oxide, titanium oxide, zirconium oxide, niobium oxide, iron carbonate, calcium carbide, and combinations thereof.

Contaminated Plastic Waste

In various embodiments, without limitation the plastic waste may be contaminated by non-plastic waste and may be obtained from at least one of the following sources: municipal waste or marine debris.

The term "municipal waste", commonly known as trash, garbage, refuse, or rubbish, refers to a waste type consisting of various items that are discarded by the public. The composition of municipal solid waste can comprise various waste types and can vary from municipality to municipality and can also change over time. In some embodiments municipal solid waste can further comprise at least one other waste type such as biodegradable waste, recyclable materials, inert waste, electrical and electronic waste, composite wastes, contaminated plastic waste, and combinations thereof.

The term "marine debris" refers to human created waste type that has deliberately or accidentally been released in a lake, river, sea, ocean, canal, or waterway. In some instances, marine debris may be mixed with naturally occurring materials (e.g., driftwood, kelp, microorganisms, etc.). In some embodiments, marine debris comprises at least one contaminated plastic waste.

The term "contaminated plastic waste" means any plastic and/or plastic material that is used and/or produced and subsequently discarded, wherein the plastic and/or plastic material is mixed or contaminated with at least one non-plastic material. In various embodiments, contaminated plastic waste comprises at least one plastic material; and at least one non-plastic material. In various embodiments, contaminated plastic waste consists of at least one plastic material; and at least one non-plastic material. In various embodiments, contaminated plastic waste consists essentially of at least one plastic material; and at least one non-plastic material.

Non-limiting examples of biodegradable waste include food and kitchen waste, green waste, paper, etc. Non-limiting examples of recyclable materials include paper, cardboard, glass, bottles, jars, tin cans, aluminum cans, aluminum foil, metals, certain plastics, fabrics, clothes, tires, batteries, etc. Non-limiting examples of inert waste include construction and demolition waste, dirt, rocks, debris, sand, concrete. Non-limiting examples of electrical and electronic waste include electrical appliances, light bulbs, washing machines, TVs, computers, screens, mobile phones, alarm clocks, watches, etc. Non-limiting examples of composite wastes include waste clothing, toys, etc.

Plastic Material

In various embodiments, the plastic material comprises at least one selected from the group consisting of plastic film, plastic foam, plastic packaging, plastic bags, plastic wrap, and combinations thereof. In some embodiments, the plastic material is at least one selected from the group consisting of plastic film, plastic foam, plastic packaging, plastic bags, plastic wrap, and combinations thereof.

In various embodiments, the plastic material comprises polyethylene.

In various embodiments, the plastic material comprises at least one selected from the group consisting of polyethylene (PE), very low density polyethylene, low density polyethylene (LDPE), linear low density polyethylene, medium density polyethylene, cross-linked polyethylene, high density polyethylene (HDPE), high density cross-linked polyethylene, high molecular weight polyethylene, ultra-low molecular weight polyethylene, ultra-high molecular weight polyethylene, and combinations thereof. In some embodiments, the plastic material is at least one selected from the group consisting of polyethylene, very low density polyethylene, low density polyethylene, linear low density polyethylene, medium density polyethylene, cross-linked polyethylene, high density polyethylene, high density cross-linked polyethylene, high molecular weight polyethylene, ultra-low molecular weight polyethylene, ultra-high molecular weight polyethylene, and combinations thereof.

Non Plastic Material

In the broadest sense, the non-plastic material is any material that is not plastic or a plastic material. Non-limiting examples of non-plastic materials include non-plastic organic materials, inorganic materials, fluids (non-plastic fluids), etc. In various embodiments, the non-plastic material comprises at least one selected from the group consisting of non-plastic organic material, inorganic material, fluid, and combinations thereof.

Non Plastic Organic Material

In some embodiments, the non-plastic organic material is at least one selected from the group consisting of plant material, animal material, algae material, bacteria material, fungus material, virus material, biological material, cellulose material, cellulose based material, cellulose containing material, and combinations thereof.

As used herein, the term "biological material" denotes a material originating, taken, isolated, derived, and/or obtained from a biological organism.

In some embodiments, the non-plastic organic material is at least one selected from the group consisting of plant derived material, animal derived material, algae derived material, bacteria derived material, fungus derived material, virus based material, biological derived material, and combinations thereof.

In some embodiments, the non-plastic organic material is at least one cellulose based material. In some embodiments, the at least one cellulose based material is at least one selected from the group consisting of paper-based materials, paper, paperboard, wood, engineered wood, plant fibers, textile, fabric, and combinations thereof.

Inorganic Material

In the broadest sense, the term "inorganic material" generally means materials that are not organic compounds or organic materials. Non-limiting examples of inorganic materials include rocks, minerals, glass, ceramics, metals, etc.

Fluid

Non-limiting examples of fluids include water, hydrocarbons, synthetic fluids, naturally derived fluids, acids, bases, or biological fluids, or any mixtures or combinations thereof.

In some embodiments, the fluid is at least one selected from the group consisting of water, hydrocarbons, synthetic fluids, naturally derived fluids, acids, bases, biological fluids, and combinations thereof.

Non-limiting examples of water include salt water, sea water, fresh water, reclaimed water, recycled water, or waste water, or any mixtures or combinations thereof.

In some embodiments, the water is at least one selected from the group consisting of salt water, sea water, fresh water, reclaimed water, recycled water, waste water, and combinations thereof.

Decomposition Mixture

In various embodiments, the decomposition mixture comprises a solid phase and a liquid phase.

In various embodiments, the solid phase comprises at least one selected from the group consisting of oligomer, polymer, and combinations thereof.

In various embodiments, the solid phase further comprises at least one solid state catalyst. In some embodiments, the solid phase optionally comprises at least one solid state catalyst. In some embodiments, the solid phase may include at least one solid state catalyst.

In various embodiments, the liquid phase comprises at least one compound comprising at least one carboxyl group. In various embodiments, the liquid phase comprises at least one compound containing at least one carboxyl group.

In various embodiments, the at least one compound comprising at least one carboxyl group is at least one organic acid. In various embodiments, the at least one compound containing at least one carboxyl group is at least one organic acid.

In some embodiments, the at least one organic acid is at least one selected from the group consisting of optionally substituted organic acid, substituted organic acid, and unsubstituted organic acid.

In some embodiments, the at least one organic acid is at least one selected from the group consisting of monocarboxylic acid, dicarboxylic acid, polycarboxylic acid, and combinations thereof.

In some embodiments, the at least one monocarboxylic acid is at least one selected from the group consisting of optionally substituted monocarboxylic acid, substituted monocarboxylic acid, unsubstituted monocarboxylic acid, and combinations thereof.

In some embodiments, the at least one dicarboxylic acid is at least one selected from the group consisting of optionally substituted dicarboxylic acid, substituted dicarboxylic acid, unsubstituted dicarboxylic acid, and combinations thereof.

In some embodiments, the at least one polycarboxylic acid is at least one selected from the group consisting of optionally substituted polycarboxylic acid, substituted polycarboxylic acid, unsubstituted polycarboxylic acid, and combinations thereof.

In some embodiments, the at least one organic acid is at least one $\alpha,\omega$-dicarboxylic acid.

In some embodiments, the at least one $\alpha,\omega$-dicarboxylic acid is at least one selected from the group consisting of optionally substituted $\alpha,\omega$-dicarboxylic acid, substituted $\alpha,\omega$-dicarboxylic acid, unsubstituted $\alpha,\omega$-dicarboxylic acid, and combinations thereof.

In some embodiments, the at least one organic acid is at least one selected from the group consisting of succinic acid, glutaric acid, adipic acid, pimelic acid, suberic acid, azelaic acid, sebacic acid, undecanedioic acid, dodecanedioic acid, and combinations thereof.

In some embodiments, the at least one organic acid is selected from the group consisting of 5-50% succinic acid, 5-50% glutaric acid, 5-50% adipic acid, 5-50% pimelic acid, 0-30% suberic acid, 0-30% azelaic acid, 0-20% sebacic acid, 0-10% undecanedioic acid, 0-10% dodecanedioic acid, and combinations thereof.

In some embodiments, the decomposition mixture comprises a composition comprising at least one selected from the group consisting of succinic acid, glutaric acid, adipic acid, pimelic acid, suberic acid, azelaic acid, sebacic acid, undecanedioic acid, dodecanedioic acid, and combinations thereof.

In some embodiments, the decomposition mixture comprises a composition comprising at least one selected from the group consisting of 5-50% succinic acid, 5-50% glutaric acid, 5-50% adipic acid, 5-50% pimelic acid, 0-30% suberic acid, 0-30% azelaic acid, 0-20% sebacic acid, 0-10% undecanedioic acid, 0-10% dodecanedioic acid, and combinations thereof.

In some embodiments, the decomposition mixture comprises:

a. succinic acid, glutaric acid, adipic acid, pimelic acid, and azelaic acid, or the salts or esters thereof, and b. at least one of oxalic acid, suberic acid, sebacic acid, undecanedioic acid, dodecanedioic acid, tridecanedioic acid, tetradecanedioic acid, pentadecanedioic acid, 2-octenedioic acid, 2-nonenedioic acid, 2-decenedioic acid, and 2-undecenedioic acid, or the salts or esters thereof.

In some embodiments, a. succinic acid is present in an amount of from about 5 to about 18 wt %, glutaric acid is present in an amount of from about 8 to about 28 wt %, adipic acid is present in an amount of about 10 to about 29 wt %, pimelic acid is present in an amount of about 10 to about 20 wt %, and azelaic acid is present in an amount of about 8 to about 13 wt %, or an equivalent amount of the salts or esters thereof, and b. if present, oxalic acid is present in an amount up to 10 wt %, if present suberic acid is present in an amount of to about 9 to about 20 wt %, if present sebacic acid is present in an amount of about 1 to about 10 wt %, if present undecanedioic acid is present in an amount of about 1 to about 8 wt %, if present dodecanedioic acid is present up to about 5 wt %, if present tridecanedioic acid is present up to about 4 wt %, if present tetradecanedioic acid is present up to about 2 wt %, and if present pentadecanedioic acid is present up to about 0.4 wt %, or an equivalent amount of the salts or esters thereof.

In some embodiments, a. succinic acid is present in an amount of from about 10 to about 11 wt %, glutaric acid is present in an amount of from about 15 to about 18 wt %, adipic acid is present in an amount of about 16 to about 18 wt %, pimelic acid is present in an amount of about 15 to about 17 wt %, and azelaic acid is present in an amount of about 10 to about 12 wt %, or an equivalent amount of the salts or esters thereof, and b. if present, oxalic acid is present in an amount up to 10 wt %, if present suberic acid is present in an amount of about 13 to about 15 wt %, if present sebacic acid is present in an amount of about 5 to about 9 wt %, if present undecanedioic acid is present in an amount of about 3 to about 6 wt %, if present dodecanedioic acid is present in an amount of about 1 to about 3 wt %, if present tridecanedioic acid is present in an amount of about 0.5 to about 1.5 wt %, if present tetradecanedioic acid is present up to about 0.2 wt %, and if present pentadecanedioic acid is present up to about 0.2 wt %, or an equivalent amount of the salts or esters thereof.

In some embodiments, a. succinic acid is present in an amount of from about 5 to about 40 wt %, glutaric acid is present in an amount of from about 8 to about 27 wt %, adipic acid is present in an amount of about 10 to about 29 wt %, pimelic acid is present in an amount of about 10 to about 20 wt %, and azelaic acid is present in an amount of about 1 to about 13 wt %, or an equivalent amount of the salts or esters thereof, and b. if present, oxalic acid is present in an amount up to 10 wt %, if present suberic acid is present in an amount of to about 4 to about 20 wt %, if present sebacic acid is present up to about 10 wt %, if present undecanedioic acid is present up to about 8 wt %, if present dodecanedioic acid is present up to about 5 wt %, if present tridecanedioic acid is present up to about 4 wt %, if present tetradecanedioic acid is present up to about 2 wt %, and if present pentadecanedioic acid is present up to about 0.4 wt %, or an equivalent amount of the salts or esters thereof.

In some embodiments, the decomposition mixture further comprises:

c. at least one of 2-nitro-suberic acid, 2-nitro-azelaic acid, 2-nitro-sebacic acid, 2-nitro-undecanedioic acid, 2-nitro-dodecanedioic acid, 2-nitro-brassylic acid, 2-nitro-tetradecanedioic acid, 2-nitro-pentadecanedioic acid, 2-nitro-hexadecanedioic acid 2-nitro-heptadecanedioic acid, 2-nitro-octadecanedioic acid, 2-nitro-nonadecanedioic acid, and 2-nitro-icosanedioic acid, or the salts or esters thereof.

In some embodiments, the decomposition mixture comprises:

a. succinic acid, glutaric acid, adipic acid, pimelic acid, and azelaic acid, or the salts or esters thereof, and b. at least one $C_8$-$C_{20}$ dicarboxylic acid substituted with a single nitro group, or the salts or esters thereof.

In some embodiments, the at least one $C_8$-$C_{20}$ dicarboxylic acid substituted with a single nitro group is nitro-suberic acid, nitro-azelaic acid, nitro-sebacic acid, nitro-undecanedioic acid, nitro-dodecanedioic acid, nitro-brassylic acid, nitro-tetradecanedioic acid, nitro-pentadecanedioic acid, nitro-hexadecanedioic acid, nitro-heptadecanedioic acid, nitro-octadecanedioic acid, nitro-nonadecanedioic acid, or nitro-icosanedioic acid, or the salts or esters thereof. In some embodiments, the $C_8$-$C_{20}$ dicarboxylic acid is 2-nitro-suberic acid, 2-nitro-azelaic acid, 2-nitro-sebacic acid, 2-nitro-undecanedioic acid, 2-nitro-dodecanedioic acid, 2-nitro-brassylic acid, 2-nitro-tetradecanedioic acid, 2-nitro-pentadecanedioic acid, 2-nitro-hexadecanedioic acid, 2-nitro-heptadecanedioic acid, 2-nitro-octadecanedioic acid, 2-nitro-nonadecanedioic acid, or 2-nitro-icosanedioic acid, or the salts or esters thereof. In some embodiments, the at least one $C_8$-$C_{20}$ dicarboxylic acid substituted with a single nitro group is present up to 1 wt % in the decomposition mixture.

In some embodiments, the liquid phase comprises a composition comprising at least one selected from the group consisting succinic acid, glutaric acid, adipic acid, pimelic acid, suberic acid, azelaic acid, sebacic acid, undecanedioic acid, dodecanedioic acid, and combinations thereof.

In some embodiments, the liquid phase comprises a composition comprising at least one selected from the group consisting of 5-50% succinic acid, 5-50% glutaric acid, 5-50% adipic acid, 5-50% pimelic acid, 0-30% suberic acid, 0-30% azelaic acid, 0-20% sebacic acid, 0-10% undecanedioic acid, 0-10% dodecanedioic acid, and combinations thereof.

In some embodiments, the method further comprises separating the at least one organic acid.

Non-limiting examples of separation techniques include simple distillation, fractional distillation, azeotropic distillation, co-distillation, fractional crystallization, standard crystallization, lyophilization, supercritical fluid extraction, solvent extraction, precipitation, and combinations thereof. In some embodiments, the separating is carried out by at least one selected from the group consisting of simple distillation, fractional distillation, azeotropic distillation, co-distillation, fractional crystallization, standard crystallization, lyophilization, supercritical fluid extraction, solvent extraction, precipitation, and combinations thereof.

Esterification

Without being bound by theory, it is hypothesized that the conversion of at least one compound containing at least one carboxyl group (e.g., an organic acid) from an acid form to an ester form occurs by a process commonly known in the art as esterification. In some embodiments, the conversion of the at least one compound containing at least one carboxyl group from an acid form to an ester form is performed under esterification conditions. In some embodiments, the dicarboxylic acids are at least partially in the form of esters.

In some embodiments, the method further comprises converting the at least one organic acid into at least one corresponding ester. In some embodiments, the at least one corresponding ester is at least one selected from the group consisting of methyl ester, ethyl ester, propyl ester, isopropyl ester, butyl ester, isobutyl ester, sec-butyl ester, tert-butyl ester, pentyl ester, and hexyl ester, and combinations thereof. In some embodiments, the at least one corresponding ester is a methyl ester. In some embodiments, the converting is carried out by esterification or esterifying.

In some embodiments, the method further comprises combining the at least one organic acid with at least one alcohol to form an esterification mixture; and subjecting the esterification mixture to conditions effective to form at least one ester. Any suitable esterification conditions known in the art may be used to form the at least one ester. For example, the at least one organic acid can be admixed with at least one alcohol and the admixture heated to cause esterification. A mineral acid may be added as a catalyst.

In some embodiments, the at least one alcohol is at least one selected from a group consisting of linear alcohol, branched alcohol, cyclic alcohol, and combinations thereof. In some embodiments, the at least one alcohol is at least one selected from the group consisting of methanol, ethanol, propanol, isopropanol, butanol, isobutanol, sec-butanol, tert-butanol, pentanol, hexanol, and combinations thereof. In some embodiments, the at least one alcohol is a $C_1$-$C_{10}$ alcohol. In some embodiments, the at least one alcohol is a $C_1$-$C_4$ alcohol. In some embodiments, the at least one alcohol is methanol.

In some embodiments, the at least one organic acid is independently in at least one ester form. In some embodiments, the at least one ester or ester form is at least one selected from the group consisting of methyl ester, ethyl ester, propyl ester, isopropyl ester, butyl ester, isobutyl ester, sec-butyl ester, tert-butyl ester, pentyl ester, and hexyl ester, and combinations thereof. In some embodiments, the at least one ester form or ester is a methyl ester.

In some embodiments, the at least one organic acid is in an ester form. In some embodiments, the α,ω-dicarboxylic acids are in an ester form. In some embodiments the succinic acid is in an ester form. In some embodiments, the glutaric acid is in an ester form. In some embodiments, the adipic acid is in an ester form. In some embodiments, the pimelic acid is in an ester form. In some embodiments the suberic acid is in an ester form. In some embodiments, the azelaic acid is in an ester form. In some embodiments, the sebacic acid is in an ester form. In some embodiments, the undecanedioic acid is in an ester form. In some embodiments, the dodecanedioic acid is in an ester form.

In some embodiments, the succinic acid, glutaric acid, adipic acid, pimelic acid, suberic acid, and azelaic acid are each independently in an ester form.

In some embodiments, the oxalic acid, suberic acid, sebacic acid, undecanedioic acid, dodecanedioic acid, tridecanedioic acid, tetradecanedioic acid, pentadecanedioic acid, 2-octenedioic acid, 2-nonenedioic acid, 2-decenedioic acid, and 2-undecenedioic acid are independently in an ester form.

In some embodiments, the 2-nitro-suberic acid, 2-nitro-azelaic acid, 2-nitro-sebacic acid, 2-nitro-undecanedioic acid, 2-nitro-dodecanedioic acid, 2-nitro-brassylic acid, 2-nitro-tetradecanedioic acid, 2-nitro-pentadecanedioic acid, 2-nitro-hexadecanedioic acid 2-nitro-heptadecanedioic acid, 2-nitro-octadecanedioic acid, 2-nitro-nonadecanedioic acid, and 2-nitro-icosanedioic acid are independently in an ester form.

In some embodiments, the $C_8$-$C_{20}$ dicarboxylic acid substituted with a single nitro group is in an ester form. In some embodiments, the $C_8$-$C_{20}$ dicarboxylic acid substituted with a single nitro group in the form of an ester is nitro-suberic acid, nitro-azelaic acid, nitro-sebacic acid, nitro-undecanedioic acid, nitro-dodecanedioic acid, nitro-brassylic acid, nitro-tetradecanedioic acid, nitro-pentadecanedioic acid, nitro-hexadecanedioic acid, nitro-heptadecanedioic acid, nitro-octadecanedioic acid, nitro-nonadecanedioic acid, or nitro-icosanedioic acid. In some embodiments, the $C_8$-$C_{20}$ dicarboxylic acid is 2-nitro-suberic acid, 2-nitro-azelaic acid, 2-nitro-sebacic acid, 2-nitro-undecanedioic acid, 2-nitro-dodecanedioic acid, 2-nitro-brassylic acid, 2-nitro-tetradecanedioic acid, 2-nitro-pentadecanedioic acid, 2-nitro-hexadecanedioic acid, 2-nitro-heptadecanedioic acid, 2-nitro-octadecanedioic acid, 2-nitro-nonadecanedioic acid, or 2-nitro-icosanedioic acid, or the salts or esters thereof. In some embodiments, the ester form is selected from the group consisting of monoester, diester, multiester, mixed diester, mixed multiester, and combinations thereof.

The term "multiester" as used herein means an ester formed by converting more than one carboxyl group from an acid form to an ester form under esterification conditions.

In some embodiments, the ester form comprises a α,ω-diester, optionally substituted α,ω-dicarboxylic acid, or substituted α,ω-dicarboxylic acid, unsubstituted dicarboxylic acid, and combinations thereof.

In some embodiments, the at least one ester comprises dimethyl succinate, dimethyl glutarate, dimethyl adipate, dimethyl pimelate, dimethyl suberate, dimethyl azelate, dimethyl sebacate, dimethyl undecanedioate, dimethyl dodecanedioate, dimethyl oxalate, dimethyl tridecanedioate, dimethyl tetradecanedioate, dimethyl pentadecanedioate, dimethyl 2-octendioate, dimethyl 2-nonendioate, 2-dimethyl 2-decendioate, dimethyl 2-undecendioate, dimethyl 2-nitro-suberate, dimethyl 2-nitro-azelate, dimethyl 2-nitro-sebacate, dimethyl 2-nitro-undecanedioate, dimethyl 2-nitro-dodecanedioate, dimethyl 2-nitro-brassylate, dimethyl 2-nitro-heptadecanedioate, dimethyl 2-nitro-octadecanedioate, dimethyl 2-nitro-tetradecanedioate, dimethyl 2-nitro-pentadecanedioate, dimethyl 2-nitro-hexadecanedioate, 2-nitro-heptadecanedioate, dimethyl 2-nitro-suberate, dimethyl 2-nitro-sebacate, dimethyl 2-nitro-undecanedioate, dimethyl 2-nitro-dodecanedioate, dimethyl 2-nitro-tetradecanedioate, and dimethyl 2-nitro-pentadecanedioate and combinations thereof.

In some embodiments, the at least one corresponding ester comprises dimethyl succinate, dimethyl glutarate, dimethyl adipate, dimethyl pimelate, dimethyl suberate, dimethyl azelate, dimethyl sebacate, dimethyl undecanedioate, dimethyl dodecanedioate, and combinations thereof.

In some embodiments, the at least one ester comprises of 5-50% dimethyl succinate, 5-50% dimethyl glutarate, 5-50% dimethyl adipate, 5-50% dimethyl pimelate, 0-30% dimethyl suberate, 0-30% dimethyl azelate, 0-20% dimethyl sebacate, 0-10% dimethyl undecanedioate, 0-10% dimethyl dodecanedioate, and combinations thereof.

In some embodiments, the at least one corresponding ester is comprises of 5-50% dimethyl succinate, 5-50% dimethyl glutarate, 5-50% dimethyl adipate, 5-50% dimethyl pimelate, 0-30% dimethyl suberate, 0-30% dimethyl azelate, 0-20% dimethyl sebacate, 0-10% dimethyl undecanedioate, 0-10% dimethyl dodecanedioate, and combinations thereof.

In some embodiments, the esterification mixture comprises a composition comprising at least one of dimethyl succinate, dimethyl glutarate, dimethyl adipate, dimethyl pimelate, dimethyl suberate, dimethyl azelate, dimethyl sebacate, dimethyl undecanedioate, dimethyl dodecanedioate, and combinations thereof.

In some embodiments, the esterification mixture comprises a composition comprising at least one of 5-50% dimethyl succinate, 5-50% dimethyl glutarate, 5-50% dimethyl adipate, 5-50% dimethyl pimelate, 0-30% dimethyl suberate, 0-30% dimethyl azelate, 0-20% dimethyl sebacate, 0-10% dimethyl undecanedioate, 0-10% dimethyl dodecanedioate, and combinations thereof.

In some embodiments, the esterification mixture comprises at least one of dimethyl succinate in an amount of from about 5 to about 18 wt %, dimethyl glutarate in an amount of from about 8 to about 28 wt %, dimethyl adipate in an amount of about 10 to about 29 wt %, dimethyl pimelate in an amount of about 10 to about 20 wt %, and dimethyl azelate in an amount of about 8 to about 13 wt %, and combinations thereof.

In some embodiments, the esterification mixture comprises at least one of dimethyl oxalate in an amount up to 10 wt %, dimethyl suberate in an amount of about 9 to about 20 wt %, dimethyl sebacate in an amount of about 1 to about 10 wt %, dimethyl undecanedioate in an amount of about 1 to about 8 wt %, dimethyl dodecanedioate up to about 5 wt %, dimethyl tridecanedioate up to about 4 wt %, dimethyl tetradecanedioate up to about 2 wt %, and dimethyl pentadecanedioate up to about 0.4 wt %, and combinations thereof.

In some embodiments, the esterification mixture comprises at least one of dimethyl succinate in an amount of from about 5 to about 40 wt %, dimethyl glutarate in an amount of from about 8 to about 27 wt %, dimethyl adipate in an amount of about 10 to about 29 wt %, dimethyl pimelate in an amount of about 10 to about 20 wt %, and dimethyl azelate in an amount of about 1 to about 13 wt %, and combinations thereof.

In some embodiments, the esterification mixture comprises at least one of dimethyl oxalate in an amount up to 10 wt %, dimethyl suberate in an amount of to about 4 to about 20 wt %, dimethyl sebacate up to about 10 wt %, dimethyl undecanedioate up to about 8 wt %, dimethyl dodecanedioate up to about 5 wt %, dimethyl tridecanedioate up to about 4 wt %, dimethyl tetradecanedioate up to about 2 wt %, and dimethyl pentadecanedioate up to about 0.4 wt %, and combinations thereof.

In some embodiments, the method further comprises separating the at least one corresponding ester. In some embodiments, the separating is carried out by distillation. In some embodiments, the separating of the at least one corresponding ester is carried out by distillation. In some embodiments, the distillation is at least one selected from the group consisting of simple distillation, fractional distillation, vacuum distillation, azeotropic distillation, co-distillation, and combinations thereof.

In some embodiments, the method further comprises converting the at least one compound containing at least one carboxyl group from the ester form to an acid form (e.g., converting the ester form back to the acid form). In some embodiments, the converting of the ester form to the acid form is performed under ester hydrolysis conditions.

Salts

In some embodiments, the methods further comprise converting the at least one dicarboxylic acid into at least one corresponding salt. In some embodiments, the at least one corresponding salt is prepared by reacting with a base to form the ion salt of the at least one dicarboxylic acid. Bases include, but are not limited to, alkali metal salts, alkaline earth metal salts and other metal ions. Exemplary ions include aluminum, calcium, lithium, magnesium, potassium, sodium and zinc in their usual valences. Organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine.

In some embodiments, the dicarboxylic acids are converted into alkaline metal salts. In some embodiments, the dicarboxylic acids are at least partially in the form of an alkaline metal salt. The alkaline metal salts can be made by reacting the dicarboxylic acids with an alkaline metal hydroxide. Exemplary alkaline metal hydroxides include sodium hydroxide, potassium hydroxide and lithium hydroxide. Exemplary alkaline metal salts of the dicarboxylic acids include the sodium, potassium and lithium salts.

In some embodiments, the oxalic acid, suberic acid, sebacic acid, undecanedioic acid, dodecanedioic acid, tridecanedioic acid, tetradecanedioic acid, pentadecanedioic acid, 2-octenedioic acid, 2-nonenedioic acid, 2-decenedioic acid, and 2-undecenedioic acid are independently in the form of an alkaline metal salt.

In some embodiments, the 2-nitro-suberic acid, 2-nitro-azelaic acid, 2-nitro-sebacic acid, 2-nitro-undecanedioic acid, 2-nitro-dodecanedioic acid, 2-nitro-brassylic acid, 2-nitro-tetradecanedioic acid, 2-nitro-pentadecanedioic acid, 2-nitro-hexadecanedioic acid 2-nitro-heptadecanedioic acid, 2-nitro-octadecanedioic acid, 2-nitro-nonadecanedioic acid, and 2-nitro-icosanedioic acid are in the form of an alkaline metal salt.

In some embodiments, the $C_8$-$C_{20}$ dicarboxylic acid substituted with a single nitro group is in the form of an alkaline metal salt. In some embodiments, the $C_8$-$C_{20}$ dicarboxylic acid substituted with a single nitro group is nitro-suberic acid, nitro-azelaic acid, nitro-sebacic acid, nitro-undecanedioic acid, nitro-dodecanedioic acid, nitro-brassylic acid, nitro-tetradecanedioic acid, nitro-pentadecanedioic acid, nitro-hexadecanedioic acid, nitro-heptadecanedioic acid, nitro-octadecanedioic acid, nitro-nonadecanedioic acid, and nitro-icosanedioic acid in the form of an alkaline metal salt. In some embodiments, the $C_8$-$C_{20}$ dicarboxylic acid is 2-nitro-suberic acid, 2-nitro-azelaicacid, 2-nitro-sebacic acid, 2-nitro-undecanedioic acid, 2-nitro-dodecanedioic acid, 2-nitro- brassylic acid, 2-nitro-tetradecanedioic acid, 2-nitro-pentadecanedioic acid, 2-nitro-hexadecanedioic acid, 2-nitro-heptadecanedioic acid, 2-nitro-octadecanedioic acid, 2-nitro-nonadecanedioic acid, or 2-nitro-icosanedioic acid, or the salts or esters thereof.

Some embodiments of the present invention can be defined as any of the following numbered paragraphs:

1. A method for decomposing contaminated plastic waste, comprising: adding contaminated plastic waste to a reaction vessel; adding at least one oxidizing agent to the reaction vessel; and subjecting the contaminated plastic waste to conditions effective to decompose the contaminated plastic waste to produce a decomposition mixture.

2. The method of paragraph 1, further comprising adding at least one solid state catalyst to the reaction vessel.

3. The method of paragraph 1, wherein the conditions comprise a temperature range; an initial pressure range of a gas; and a residence time in the reaction vessel.

4. The method of paragraph 1, wherein the contaminated plastic waste comprises at least one plastic material; and at least one non-plastic material.

5. The method of paragraph 4, wherein the plastic material comprises at least one selected from the group consisting of plastic film, plastic foam, plastic packaging, plastic bags, plastic wrap, and combinations thereof.

6. The method of paragraph 4, wherein the plastic material comprises polyethylene.

7. The method of paragraph 4, wherein the plastic material comprises at least one selected from the group consisting of very low density polyethylene, low density polyethylene, linear low density polyethylene, medium density polyethylene, cross-linked polyethylene, high density polyethylene, high density cross-linked polyethylene, high molecular weight polyethylene, ultra-low molecular weight polyethylene, ultra-high molecular weight polyethylene, and combinations thereof.

8. The method of paragraph 4, wherein the non-plastic material comprises at least one selected from the group consisting of non-plastic organic material, inorganic material, fluid, and combinations thereof.

9. The method of paragraph 1, further comprising separating the decomposition mixture into a solid phase and a liquid phase.

10. The method of paragraph 9, wherein the solid phase comprises at least one selected from the group consisting of oligomer, polymer, and combinations thereof.

11. The method of paragraph 10, wherein the solid phase further comprises at least one solid state catalyst.

12. The method of paragraph 9, wherein the liquid phase comprises at least one compound containing at least one carboxyl group.

13. The method of paragraph 12, wherein the at least one compound containing at least one carboxyl group is at least one organic acid.

14. The method of paragraph 13, further comprising converting the at least one organic acid into at least one corresponding ester.

15. The method of paragraph 13, wherein the at least one organic acid is selected from the group consisting of monocarboxylic acid, dicarboxylic acid, polycarboxylic acid, and combinations thereof.

16. The method of paragraph 13, wherein the at least one organic acid is an α,ω-dicarboxylic acid.

17. The method of paragraph 13, wherein the at least one organic acid is selected from the group consisting of succinic acid, glutaric acid, adipic acid, pimelic acid, suberic acid, azelaic acid, sebacic acid, undecanedioic acid, dodecanedioic acid, and combinations thereof.

18. The method of paragraph 13, further comprising separating the at least one organic acid.

19. The method of paragraph 14, further comprising separating the at least one corresponding ester.

20. The method of paragraph 2, wherein the at least one solid state catalyst is selected from the group consisting of zeolite, alumina, silico-alumino-phosphate, sulfated zirconia, zinc oxide, titanium oxide, zirconium oxide, niobium oxide, iron carbonate, calcium carbide, and combinations thereof.

21. The method of paragraph 1, wherein the at least one oxidizing agent is selected from the group consisting of oxygen ($O_2$), nitric oxide (NO), nitrous oxide ($N_2O$), nitrogen dioxide ($NO_2$), nitric acid ($HNO_3$), aqueous nitric acid ($HNO_3$), and combinations thereof.

22. The method of paragraph 3, wherein the temperature range is from 60° C. to 200° C.

23. The method of paragraph 3, wherein the gas is at least one selected from the group consisting of air, nitrogen (N2), oxygen (O2), and combinations thereof.

24. The method of paragraph 3, wherein the initial pressure of the gas is 0 psi to 1000 psi.

25. The method of paragraph 3, wherein the residence time in the reaction vessel is one selected from the group consisting of 30 minutes to 30 hours, less than 30 minutes, and more than 30 hours.

26. The method of paragraph 10, further comprising feeding the oligomer, the polymer, and combinations thereof back into the reactor.

27. The method of paragraph 9, wherein the liquid phase further comprises the at least one oxidizing agent.

28. The method of paragraph 27, further comprising collecting and regenerating the at least one oxidizing agent.

29. The method of paragraph 11, wherein the at least one solid state catalyst is selected from the group consisting of zeolite, alumina, silico-alumino-phosphate, sulfated zirconia, zinc oxide, titanium oxide, zirconium oxide, niobium oxide, iron carbonate, calcium carbide, and combinations thereof.

30. The method of paragraph 14, wherein the at least one corresponding ester is selected from the group consisting of dimethyl succinate, dimethyl glutarate, dimethyl adipate, dimethyl pimelate, dimethyl suberate, dimethyl azelate, dimethyl sebacate, dimethyl undecanedioate, dimethyl dodecanedioate, and combinations thereof.

Some embodiments described herein relate to a system that combines Polyethylene (definition provided at the end of the document) with an Oxidizing Agent (definition provided at the end of the document) in a reactor to break-down polyethylene into Product (definition provided at the end of the document) and recycle the Oxidizing Agent. The system is comprised of multiple units and to attain high conversion of polyethylene, low waste production, and minimize the makeup of Oxidizing Agent. In addition to the Oxidizing Agent, a catalyst (definition provided at the end of the document) may be used in the process to enhance the reaction rate or product yield. The main components of the system include a reactor, Reaction Gas (definition provided at the end of the document) recovery and regeneration unit, Product recovery unit, and an Oxidizing Agent concentration unit. This process can be run in multiple modes of operation: batch, semi-batch, and continuous. The layout of the process will be different depending on the mode of operation.

This disclosure defines the complete polyethylene chemical recycling system that currently does not exist commercially. The chemical recycling process disclosed herein is unique and addresses a huge plastic waste problem by diverting polyethylene from landfills. This process transforms polyethylene to Product that can be used for value-adding industrial applications (e.g., performance materials, polymers, fibers, compostable plastics, paints and coatings, lubricants, adhesives, fragrances, skincare products, etc.) serving as a drop-in replacement of existing chemical intermediates, or as new chemical intermediates.

In the existing literature, there have been attempts to convert polyethylene into chemical compounds such as dicarboxylic acids. Pifer et al. ("Chemical Recycling of Plastics to Useful Organic Compounds by Oxidative Degradation,"*Angewandte Chemie International Edition*, Vol. 37, Issue 23; pp. 3306-3308, 1998) as well as Remias et al. ("Oxidative Chemical Recycling of Polyethene," *Comptes Rendus de lAcadémie des Sciences—Series IIC—Chemistry*, Vol. 3, Issue 7; pp. 627-629, 2000) have converted low density and high density polyethylene into valuable chemicals including succinic acid, glutaric acid, adipic acid, and pimelic acid. However, such methods involve using reactive gases (i.e. nitric oxide) in pressurized autoclaves and suggest scale-up challenges due to high operating and capital expenses. The system and method disclosed herein is able to produce valuable chemicals, such as the dicarboxylic acids mentioned above, from polyethylene using reflux methods with industrially common Oxidizing Agent (e.g., nitric acid). Although Garaeva et al. ("Composition, Properties, and Application of Products Formed in Oxidation of Polyethylene by Nitric Acid," *Russian Journal of Applied Chemistry*, Vol. 83, Issue 1; pp. 97-101, 2010) has attempted nitric acid reflux with polyethylene, the research group produced a majority output of nitrocarboxylic acids, which are less valuable and have fewer industrial applications compared to the non-nitrated dicarboxylic acids such as those capable of being produced as disclosed herein.

In this disclosure, polyethylene is a polymer with many repeating carbon units that is continually broken down into shorter segments and functionalized (e.g., carbon chains can become oxidized forming dicarboxylic acids or monocarboxylic acids). The scission event continues as long-chain polymers depolymerize into gradually shorter-chain species by the Oxidizing Agent until the chain-length has reached a terminal length range and is no longer broken down (e.g., C2-C9 dicarboxylic acids). Alternatively, the reaction process can be controlled to stop the scission event prematurely to achieve chain lengths that are longer than the terminal length range. These various chain lengths are collectively considered Product. To enable the reaction of polyethylene into Product, an appropriate amount of Oxidizing Agent is added to breakdown the polymer into desired chain lengths and the Oxidizing Agent should be at an appropriate concentration as well as Polyethylene-to-Oxidizing Agent ratio to produce Product quantities large enough for commercial application. The processes and equipment described in this disclosure allow for control over the process to enable conversion of polyethylene into Product, including terminal reaction species and/or other species of desired chain-lengths.

Both the overall process and individual units are optimized to economically convert polyethylene to Product and minimize use of Oxidizing Agent and Catalyst. The equipment for chemical recycling of polyethylene is designed to optimize process performance metrics within that unit (e.g., the reactor is designed to maximize conversion of polyethylene, the separation units are designed to recover Oxidizing Agent and recycle back to the reactor, and the absorption unit to recover Reaction Gas and regenerate the Oxidizing Agent). These units are designed to minimize energy use and are combined into a process system that recovers and re-uses Oxidizing Agent and Catalyst to minimize the amount made-up in the process. This process is also designed to minimize waste in the gas and liquid phases. Overall, this process can significantly improve the economics of producing Product while diverting polyethylene from waste streams (e.g., landfill and the ocean), extending the lifetime of the carbon. In addition, use of polyethylene for Product reduces the use of petrochemical feedstock that is conventionally used to make Product.

Method to Convert Polyethylene Into a Reaction Product

Disclosed herein is a method/process to convert polyethylene into a reaction product, or "product," using an Oxidizing Agent and specific operating conditions (e.g., temperatures between 60° C. and 200° C.). This is a chemical reaction that is controlled in a reactor. The problem is that the Oxidizing Agent is partially converted into a Reaction Gas that exits the reactor in the gas phase. To make the process economical, this Reaction Gas is converted back into the Oxidizing Agent and recycled to the reactor. The Product and Oxidizing Agent that remain in the liquid phase are removed from the reactor and the Product is separated. This disclosure details solutions to separate, recover, and recycle the Oxidizing Agent as well as recover the Product.

Figure 21:
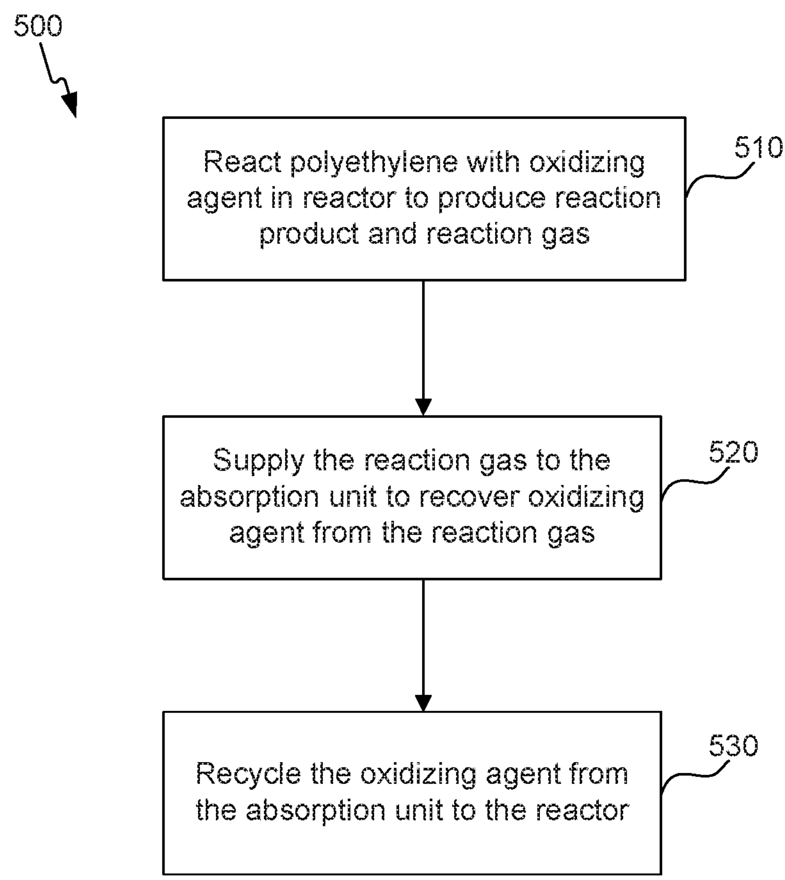
FIG. 21 depicts, in accordance with various embodiments of the invention, a flow diagram of a method to convert polyethylene into a reaction product.

In an embodiment of a method for decomposition of polyethylene 500 as shown in FIG. 21, polyethylene and an oxidizing agent are supplied to and react in a reactor to produce a reaction gas and a reaction product 510. The reaction gas is supplied to an absorption unit to recover oxidizing agent from the reaction gas 520. The recovered oxidizing agent from the absorption unit is then recycled to the reactor 530 in order to improve the economics of the decomposition process. The reaction product may be supplied to a separation unit for separating the product and oxidizing agent. The oxidizing agent recovered from the separation unit may also be recycled to the reactor.

Figure 5:
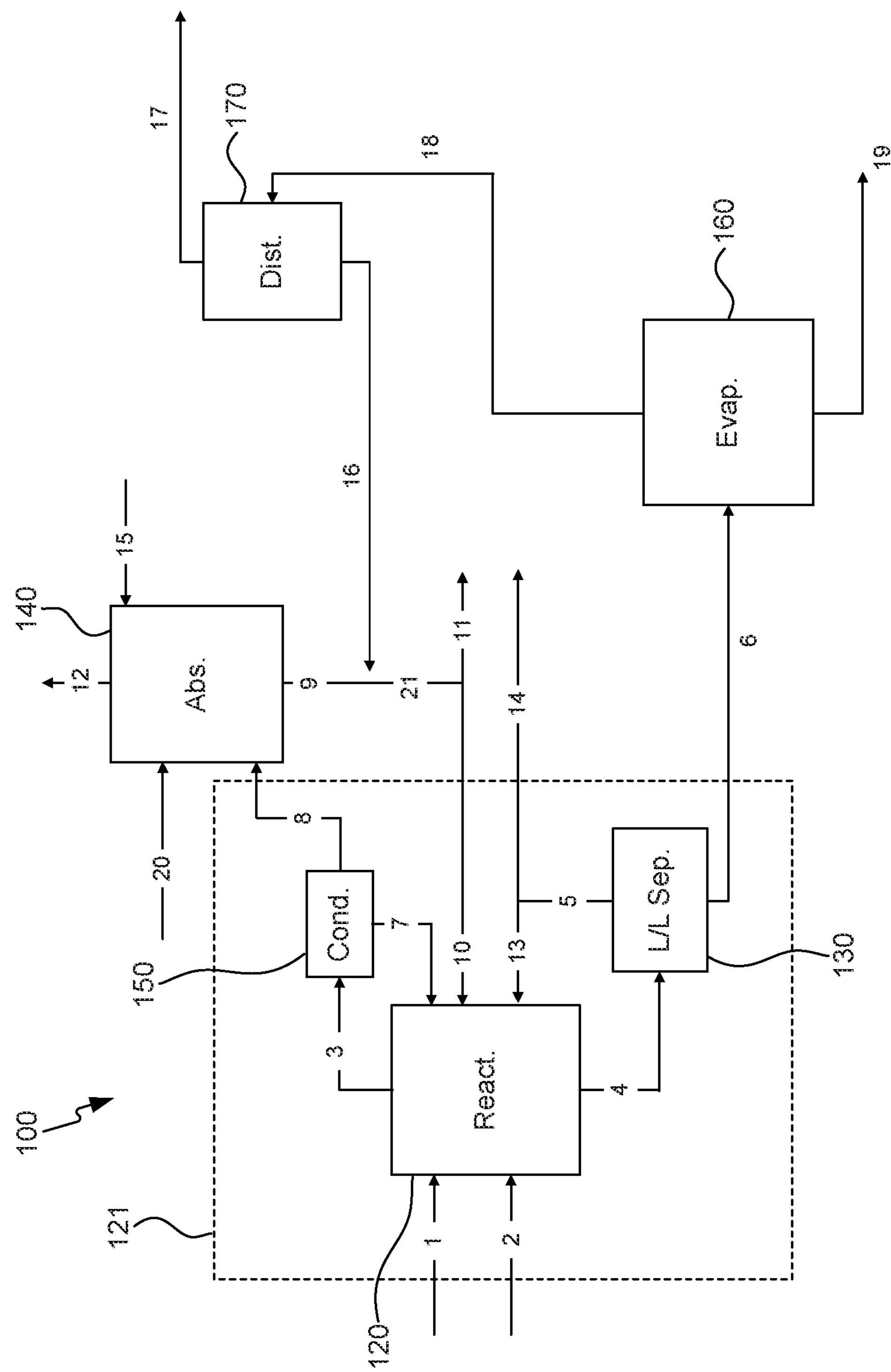
FIG. 5 depicts, in accordance with various embodiments of the invention, a chemical recycling process flow diagram.

System that Uses an Oxidizing Agent to Break-Down Polyethylene Into Product and Recycles the Oxidizing Agent A simplified illustration of the process flow 100 for a chemical recycling process is shown in FIG. 5. The main process to produce Products, consists of four key units: the reactor (React.) 120, Oxidizing Agent regeneration in an absorption unit (Abs.) 140, Product/Oxidizing Agent separation unit 160 to separate the Oxidizing Agent and Product (Evap) into two separate streams, and then a unit 170 to concentrate the Oxidizing Agent back to concentrations necessary for the reactor 120, enabling recycle. The chemical reactor 120 breaks down polyethylene into Product. Key metrics for the reaction are the relative amounts of the polyethylene to Oxidizing Agent fed into the reactor 120, the concentration of Oxidizing Agent in the aqueous phase, and the other process variables like pressure, temperature, mixing, and residence time. In addition, a catalyst may be fed into the reactor 120 to speed the conversion of polyethylene into Product. The relative amount of polyethylene in mass to Oxidizing Agent in mass added into the reactor 120 as well as the concentration of Oxidizing Agent dictates the reaction rates and polyethylene conversion to Product and also the type of chemical reactor used. For a stirred tank reactor, the amount of polyethylene to Oxidizing Agent on a mass basis may be in the range of (e.g., 1:3 to 1:100, e.g., 1:10 to 1:100, e.g., 1:3 to 1:50, e.g., 1:3 to 1:25, e.g., 1:3 to 10, e.g. 1:3 to 1:5).

In FIG. 5, the reactor section 121 of the process is highlighted and within the box with a dashed-line. Two feed streams labeled 1 and 2 contain the polyethylene and Oxidizing Agent, respectively. Many different reactor types, geometries, and configurations are possible as well as how the feed streams are added into the reactor. Once in the reactor 120, the polyethylene and Oxidizing Agent react at elevated temperatures (e.g., 60° C. to 200° C., e.g., 75° C. to 150° C., e.g., 100° C. to 125° C.), producing a Reaction Gas. The Reaction Gas as well as volatilized Oxidizing Agent and entrained liquid/solid droplets will exit the top of the reactor 120 [stream 3] and can enter either into a condenser unit (Cond.) 150 or directly into the absorption unit 140. The purpose of the condenser unit 150 is to condense any volatilized liquids if the process is run around the boiling point of the Oxidizing Agent (e.g., any boiled off liquid vapors will be cooled in the condenser and sent back to the reactor) [stream 7]. The non-condensable gases will continue to the feed of the absorption unit 140 [stream 8]. The absorption unit 140 will be designed to convert any Reaction Gas back into the Oxidizing Agent. An intermediate step will be to fully oxidize the Reaction Gas using air, enriched oxygen, or pure oxygen (e.g., converting NO to $NO_2$). The air, enriched oxygen, or pure oxygen stream will be fed into the absorption unit 140 or mixed with the Reaction Gas [stream 8] prior to being fed into the absorption unit 140. It is also possible that air or enriched oxygen is added directly into the reactor 120. The Reaction Gas that can be regenerated directly back into the Oxidizing Agent flows up the absorption column that is packed with different internal structured materials or trays, contacting a liquid phase that is fed into the top of the absorption column [stream 15]. The Reaction Gas absorbs into the liquid phase (e.g., NO, $NO_2$, $N_2O_3$, $N_2O_4$ absorbs into water), reacting and converting back into the Oxidizing Agent (e.g., $HNO_3$). This recovered and regenerated Oxidizing Agent in stream 9 can be sent directly back to the reactor 120 or sent to the unit 170 used to concentrate the Oxidizing Agent (e.g., mixed with stream 18). The gas exiting the absorption unit [stream 12] will contain very small amounts of the Reaction Gas and can be emitted to the atmosphere or sent to additional units to remove any VOCs or to further reduce the Reaction Gas concentration.

At the bottom of the reactor 120, liquid is withdrawn [stream 4] and can be sent directly to the separation section (Evap.) 160 to separate Product (e.g., 1 wt % to 20 wt % dicarboxylic acid) from the Oxidizing Agent or sent to other units prior to the separation (like a liquid-liquid separator 130 or another reactor). The case of having an intermediate liquid-liquid separation unit (L/L Sep.) 130 prior to the separation unit 160 is shown in FIG. 5. The purpose of the liquid-liquid separation unit 130 is to enable recycling of the separate phase of unreacted or partially reacted polyethylene that is either a solid or liquid. The liquid-liquid separation unit 130 could be a vessel that is designed to let two or more different density phases separate and then remove each of the phases individually (e.g., the low-density phase is removed from the top of the vessel and the high-density phase is removed from the bottom of the vessel). The unreacted or partially reacted polyethylene [stream 5] will be recycled back to the reactor [stream 13] or sent in stream 14 to another unit or purged from the system to prevent buildup of any inert or species that do not react. The liquid-liquid separation unit 130 may be a separator vessel, a centrifugal type device (cyclone or hydrocyclone), a mechanical device like a continuous flow centrifuge, among others. The liquid-liquid separation unit 130 may also incorporate filtration to remove any solids or additional modifications to handle solids that may come into the process in the form of contamination on the polyethylene (e.g., the separation vessel may be designed for three or more phases (gas, low-density liquid, high-density liquid, and high-density solids).

The product stream from the reactor 120 and liquid-liquid separation unit [stream 6] primarily contains Product and Oxidizing Agent. This stream is sent to the separation unit (Evap.) 160 to separate the Product from the Oxidizing Agent. This can be done in single or multiple steps and using different physical principles. For example, stream 6 could be sent to an evaporator where the Oxidizing Agent is vaporized [stream 18] and the Product [stream 19] remains a liquid, taking advantage of the different boiling points of the species. The type of evaporator could be a wiped-film evaporator, falling-film evaporator, forced-circulation evaporator or a flash evaporator, for example. The degree of separation may vary. In one case, all of the low boiling material is removed causing the Product to form a solid (e.g. all Oxidizing Agent is removed), recovering nearly all of the Oxidizing Agent. This would improve the overall economics and may simplify Product storage and transportation. Examples of types of equipment that allow for complete removal of all Product into solid-form from stream 6:

1. hybrid wiped-film evaporator with internals to prevent solid buildup and to convey solids out of the equipment like a screw conveyor, and 2. spray dryer where all of the volatile liquid and active-Oxidizing Agent is evaporated. This may also include the option where part of the volatile liquid in stream 6 is removed in equipment discussed above, concentrating the product stream (e.g., 25-90% of the volatile liquid in stream 6 is removed) and then the concentrated product stream is sent to a spray dryer, or fluidized bed dryer, or rotary drum dryer) where the remaining liquid is removed.

The separation unit 160 could also be a crystallizer, where the products are solidified and removed via filtration or some other technique. The separation unit 160 could also be an extraction unit where stream 18 is contacted with another liquid that the Product is soluble in, but that the Oxidizing Agent is insoluble.

The vaporized or separated Oxidizing Agent stream out of the separation unit 160 [stream 18] may be recycled directly to the reactor 120 (e.g., connected and mixed with streams 21 or 10) or the Oxidizing Agent may need to be concentrated in a separate unit. This unit could be a distillation unit (Dist.) 170 where the aqueous phase is partially separated from the Oxidizing Agent and removed [stream 17], concentrating the Oxidizing Agent to a concentration necessary to be recycled to the reactor 120 (e.g., 45 wt % to 95 wt %, e.g., 50 wt % to 75 wt %) [stream 16]. This concentrating section may be a distillation column with different internals or packing, or a rectifying column that this attached the top of evaporation unit where the vapor stream 18 would be the feed. The feed into the distillation unit 170 may be a mix of any number of streams into the process where the Oxidizing Agent concentration of the mixed stream is less than what is needed for the reactor 120. Stream 16 out of the distillation column 170 or Oxidizing Agent concentrator may flow at a rate necessary to supply all Oxidizing Agent to the reactor 120 (e.g. 1 to 50 times the rate of the polyethylene feed) or partially supply Oxidizing Agent to the reactor 120, in which case additional Oxidizing Agent is added to the process [stream 2]. In addition, a dilute makeup Oxidizing Agent stream may be sent to the distillation unit 170 to offer more options for process feed and potentially reduce costs (e.g., [stream 2] is a dilute Oxidizing Agent that is mixed with [stream 18] instead of being directly fed to the reactor). In this scenario, the distillation column 170 or concentration unit supplies all oxidizing agent to the reactor 120.

An example of the overall process considers the process configuration, which is one of many. This example illustrates the importance of each step and how when combined, creates an efficient complete process. The basis considered for this example is 1000 kg/hr of feed polyethylene and a ratio of 1:20 for the amount of polyethylene to Oxidizing Agent fed into the reactor 120 (the amount of Oxidizing Agent fed into the reactor includes recycle and make-up, which may be 20,000 kg/hr). For a single stirred tank reactor, polyethylene is added into the system as well as Oxidizing Agent. The polyethylene and Oxidizing Agent react forming Product and Reaction Gas. In this example, polyethylene is 100% converted into Product by mass (the relative fraction of dicarboxylic acids to other species is 80%). Oxidizing Agent reacts with Polyethylene and 15 wt % of the Oxidizing Agent converts into Reaction Gas and Product (alternatively, for every mole of Oxidizing Agent reacted a mole of Reaction Gas is produced). The product and unreacted Oxidizing Agent stream exits the bottom of the reactor 120 and is fed to a first unit (e.g., evaporator) to separate Oxidizing Agent and Product. In this unit, 92 wt % of the stream is vaporized and all of the Product and some of the Oxidizing Agent exit the bottom of the unit (e.g., about 5 w % to 20 wt % of this stream is Oxidizing Agent) and may continue for further processing to purify the Product and remove any residual Oxidizing Agent (e.g., separate dicarboxylic acids from other species or separate dicarboxylic acids into individual species). The vapor stream out of the first unit (e.g., evaporator) is primarily Oxidizing Agent at a concentration lower (e.g., 55 wt % to 63 wt %) than the specified feed Oxidizing Agent concentration (e.g., 65 wt % to 70 wt %), because a fraction of the Oxidizing Agent has reacted and converted to Reaction Gas and Product. The vapor is sent to another separation unit (e.g., distillation column, or addition tank) to concentrate the Oxidizing Agent (e.g., remove water from an aqueous Oxidizing Agent, or add higher concentrations of the Oxidizing Agent) to the desired starting concentration. This recovered Oxidizing Agent is recycled back to the reactor 120 and makes up ~85% of the Oxidizing Agent added into the reactor 120 as Oxidizing Agent feed. At the top of the reactor 120, the Reaction Gas is mixed with air to oxidize some of the Reaction Gas (e.g., convert NO into $NO_2$). The Reaction Gas stream is then sent to an absorption column 140 to react the Reaction Gas with water and convert into Oxidizing Agent (e.g., the Reaction Gas is contacted with water to produce Oxidizing Agent). The regenerated Oxidizing Agent is recycled back to the reactor 120 and the tail gas exiting the absorption column 140 is mostly $N_2$ (e.g., ~95%). Recovering and recycling the Oxidizing Agent from the reactor bottoms separated from the Product and concentrated and the Oxidizing Agent regenerated from the Reaction Gas, results in >97.5 wt % Oxidizing Agent recovery, requiring only a small makeup Oxidizing Agent stream. This overall process example highlights how different process units integrate to enable efficient conversion of polyethylene to Product, minimizing waste and the need to consume Oxidizing Agent, reducing operating costs of the process.

The process may have multiple reactor units 120, different types of reactor units, and different sizes of reactor units. The reactor units 120 may be in series or parallel configuration with heating, cooling, or different types of equipment between the reactor units (like liquid-liquid separators to separate any polyethylene from Product that is not fully reacted). The process may be operated in batch, semi-batch, or continuous mode. Different sections may be operated in different modes. For example, multiple reactors connected in parallel may be individually operated in batch mode. The reactor process is staggered so that one reactor is always being emptied and supplies other parts of the process. After emptying, that reactor is filled again and another reactor that has completed the process is emptied.

The piping layout connecting the process equipment and how the streams are mixed and added into each unit can be varied. The flow rates, the pressure, temperature, and Reynolds number of the fluid in the pipe may vary as well as varying the, size and materials of the piping and lines.

The layout and construction of the system may be an entirely new plant (green field), built on an existing plant site (brownfield), a retro-fit of a process that has some applicable existing process equipment, a stick-build plant, a single modular plant, a modular plant where eat unit is a separate module.

Reactor for Converting Polyethylene Into Product

A reactor 120 is used to convert polyethylene into product. The chemical reaction involved in this conversion happens in the chemical reactor mentioned in this disclosure.

An embodiment includes a reactor 120 as a component of the whole process and uses an Oxidizing Agent to convert polyethylene into chemical Product and generate Reaction Gas. The reactor 120 can be a continuous stirred tank reactor, semi-continuous reactor, or batch reactor with controlled heating, agitation to mix the reactor content, reflux to condense the vapors, control valve to control the flow of product stream from reactor to separation unit, and feeder unit that feeds the inputs at a uniform rate. There may also be multiple reactor vessels to enable staged reactions.

Generally, pretreated or untreated polyethylene enters the reactor 120 along with Oxidizing Agent (e.g., 45 wt % to 95 wt % nitric acid). This pretreatment involves one or more of the unit operations including shredding, cleaning, pulverizing, melting, washing and drying. The reactor 120 is designed to handle different forms of polyethylene and can be operated with variable temperature, stirring and flowrate of the mixture. As the reactor 120 reaches desired temperature (e.g. temperatures between 60° C. and 200° C., e.g., 80° C. to 150° C.), the conversion reaction starts. Near the start of the reaction, Oxidizing Agent will enable the polyethylene to be depolymerized into shorter-chain species, and as the reaction proceeds, these shorter-chain species will be further broken down into Product. A Reaction Gas will be generated. Any unreacted polyethylene or shorter-chain species can be further reacted into Product.

Figure 6:
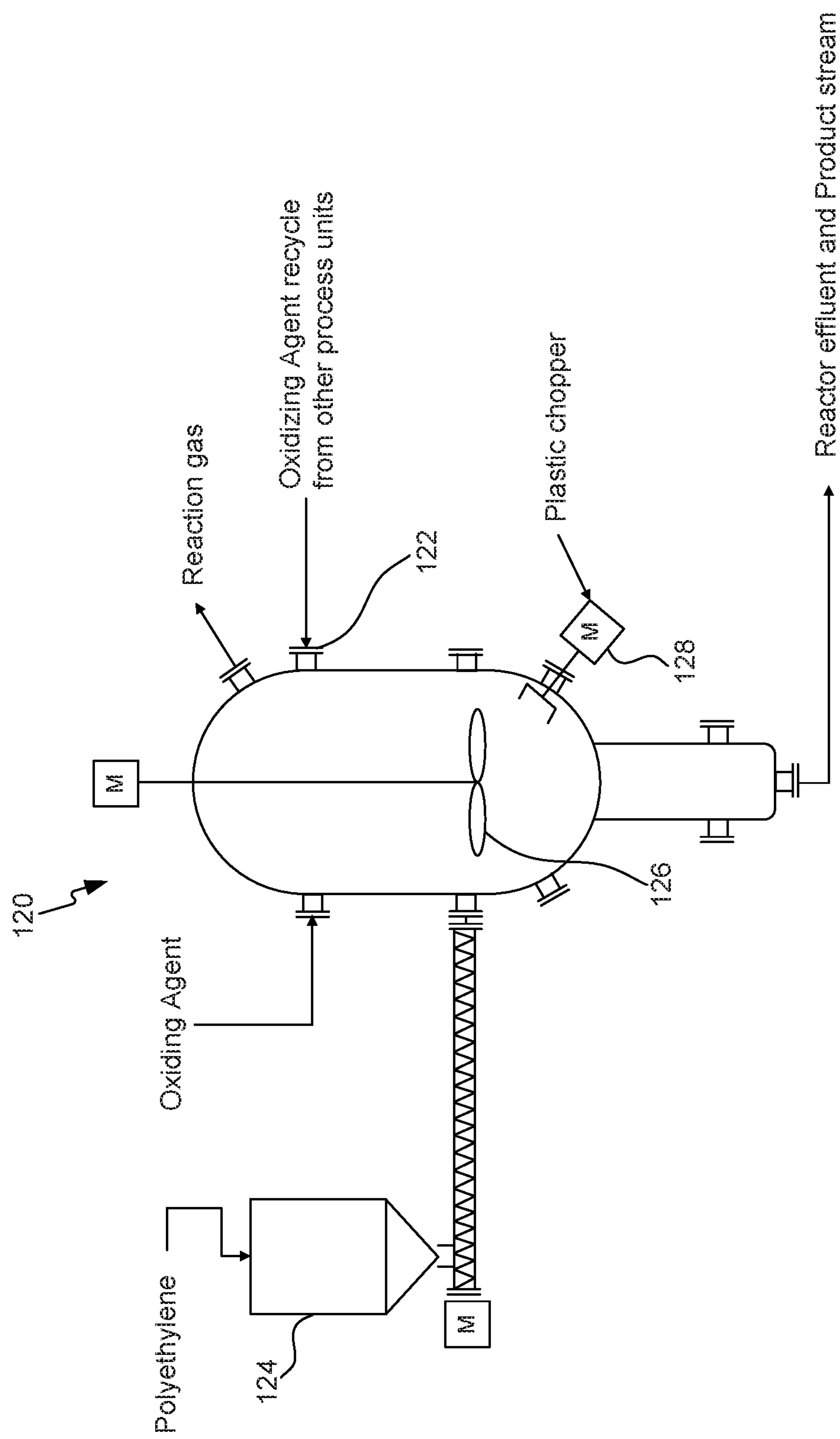
FIG. 6 depicts, in accordance with various embodiments of the invention, a continuous stirred tank reactor (CSTR) chemical recycle reactor.

FIG. 6 shows a stirred tank reactor that can be operated in batch, semi-batch or continuous mode (in one embodiment, continuous mode). This reactor 120 has multiple ports to add and remove material from the reactor 120 (e.g., feed, recycle, outlets, etc.). The Oxidizing Agent is added into the reactor 120 at a specified concentration through a recycle stream 122 or make-up feed stream or both. Polyethylene is added separately into the reactor 120, but the make-up Oxidizing Agent could be combined with the polyethylene to create a dispersion that is fed into the reactor 120. The reactor 120 can include a system 124 to add the polyethylene into the reactor 120 such as a screw conveyor or melting of the polyethylene and extruding the liquid polyethylene into the reactor. The form factor and size of the polyethylene is important to the process as well. The smaller the polyethylene size the more exposed surface area of the dispersed or emulsified polyethylene there is per unit volume of the polyethylene that is exposed to the Oxidizing Agent, resulting in a faster reaction. The tank will be stirred and capable of creating high turbulence and shear rates to disperse the polyethylene and Oxidizing Agent and also mix the Oxidizing Agent and polyethylene. Different types of impellers 126 may be used (e.g., paddle, anchor, helical, propeller, pitched blade, etc.). There may be an additional feature at the bottom of the reactor where a motor drives a chopping blade 128 within the reactor 120. The chopping blade 128 acts to blend and breakdown the polyethylene even further using very high rotation rates, creating very high shear like in a blender (e.g., rotating at 500 to 10,000 rpm). This chopping blade 128 may be used in lieu of feeding a pre-treated polyethylene or in combination. The reactor 120 may also have different geometries and features. This may include a boot at the bottom to separate the Oxidizing Agent phase from the fresh or incompletely reacted polyethylene phase to enable a product stream that is entirely or mostly the Oxidizing Agent and Product. The reactor vessel may have different size and geometries, but the size is primarily determined from the desired residence time in the reactor (e.g., 30 min to 12 hr, e.g., lhr to 9 hr, e.g., 1 hr to 5 hr, e.g., 3 hr to 9 hr, e.g., 3 hr to 5 hr). The residence time may vary depending on the process conditions (e.g., higher temperature may require a shorter residence time). The residence time is scale independent and is determined from the mass of material in the reactor divided by the flow rate of the combined feed streams into the reactor.

For example, one metric ton of polyethylene per hour is added into the reactor 120. The ratio of polyethylene to Oxidizing Agent is 1:100, making the combined Oxidizing Agent recycle and make-up mass flow 100 metric tons per hour. For a residence time of 3 hours, the required reactor capacity is 3 hrs×101 metric tons/hour or 303 metric tons. To process the same polyethylene feed rate, a concentrated feed ratio of 1:10 would require the feed stream flows of one metric ton of polyethylene per hour and a combined Oxidizing Agent recycle and make-up mass flow of 10 metric tons per hour. The reactor capacity for a 3 hour residence time is only 33 metric tons. An even more concentrated feed ratio of 1:3 would require the feed stream flows of one metric ton of polyethylene per hour and a combined Oxidizing Agent recycle and make-up mass flow of 3 metric tons per hour. The reactor capacity for a 3 hour residence time is only 12 metric tons. Higher ratios of polyethylene to Oxidizing Agent are preferable to reduce the reactor size and volume. But higher ratios of polyethylene to Oxidizing Agent may require different residence times (e.g. 3-12 hrs, e.g., 3-9 hrs, e.g., 3-5 hrs) and Oxidizing Agent concentrations in a single reactor or multiple reactors to allow for replenishment of the Oxidizing Agent to increase the Oxidizing Agent concentration and speed the breakdown of polyethylene.

Figure 7:
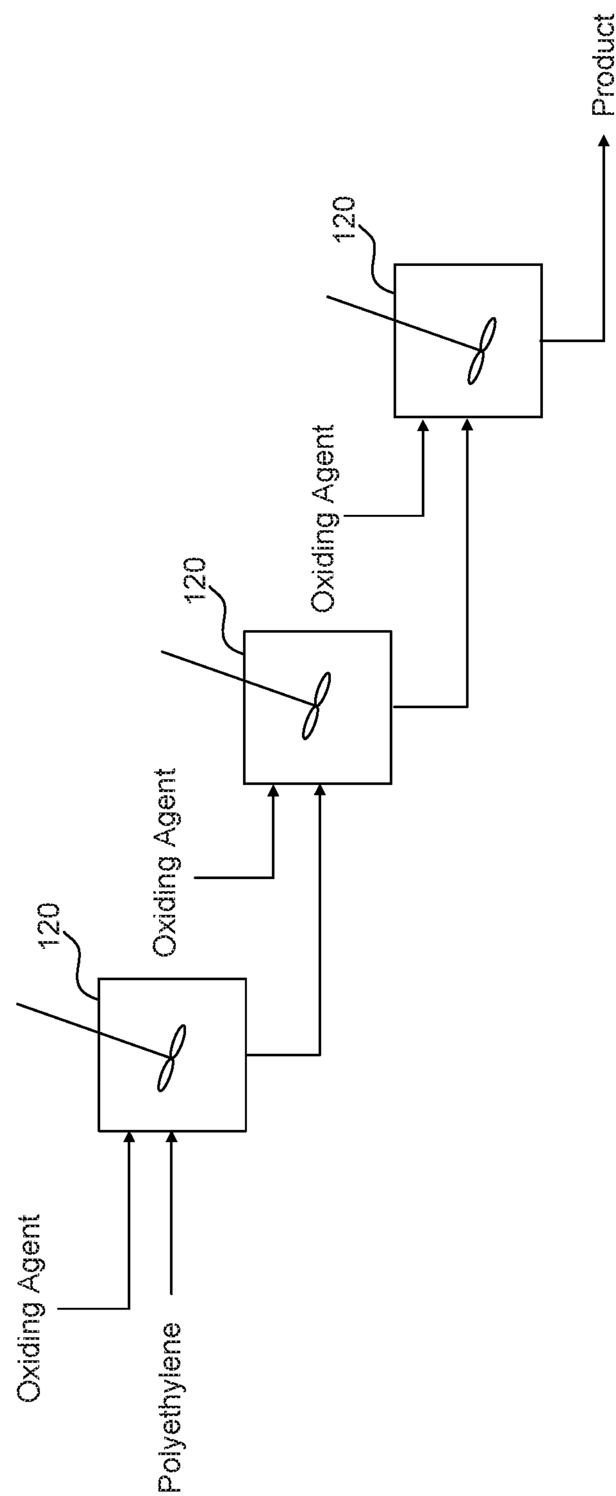
FIG. 7 depicts, in accordance with various embodiments of the invention, a continuous stirred tank reactor train for chemical recycle.

FIG. 7 shows a reactor scheme used to promote complete conversion of the polyethylene into Product. This scheme shows multiple stirred tank reactors 120 in series where the effluent from one reactor 120 feeds into a next reactor 120. There is a capability to add fresh Oxidizing Agent at a specified concentration to the feed of the next reactor 120 that will increase the concentration of the Oxidizing Agent in the tank once mixed. The number of stirred tanks can be influenced by the relative amount of polyethylene to Oxidizing Agent phase in the first reactor. The more polyethylene added into the system, the more reactors may be required as well as the need to add more Oxidizing Agent to maintain a high reaction rate. In this multiple reactor scheme, stirred tanks and plug flow reactors may be alternated (e.g., a plug flow reactor is followed by a stirred tank and vice versa).

Figure 8:
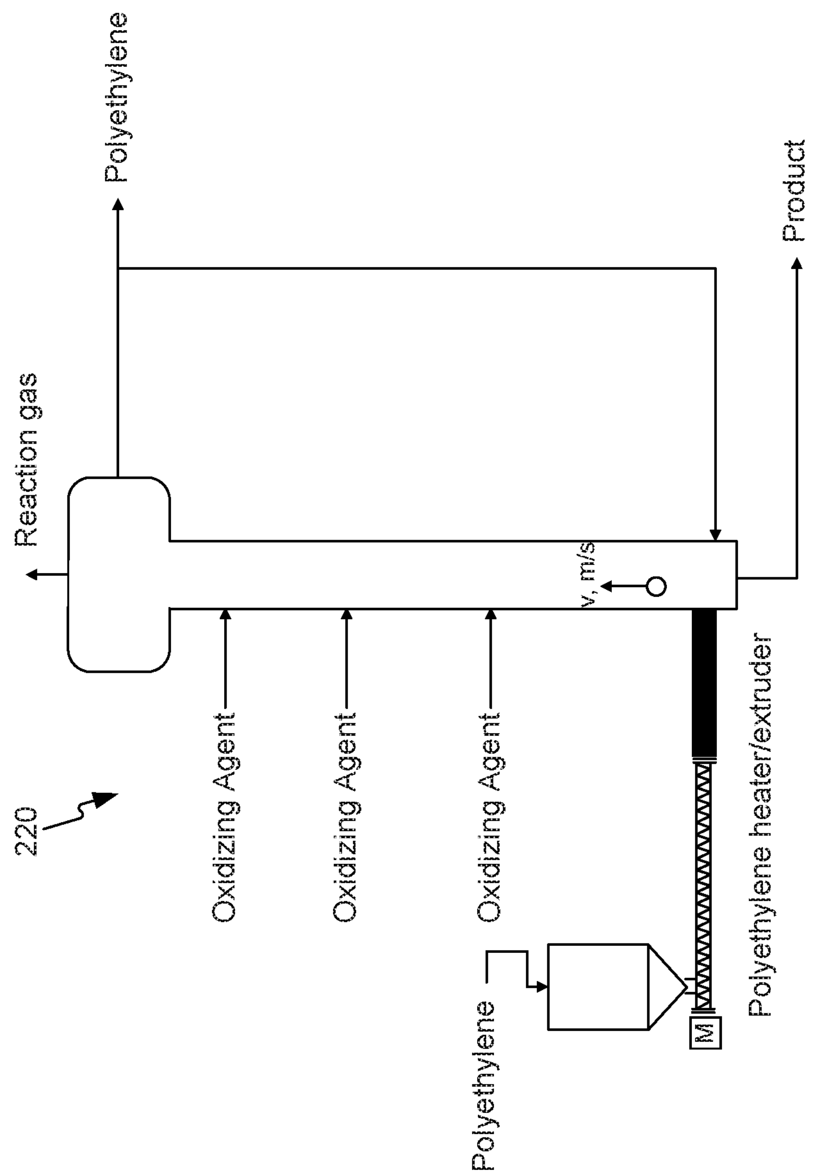
FIG. 8 depicts, in accordance with various embodiments of the invention, a gravity separation reactor for chemical recycling.

FIG. 8 shows a gravity flow reactor 220 that is a tall vessel maintained at the specified temperature and pressure. The Oxidizing Agent phase is added to the top of the reactor vessel and flows down the reactor 220. The polyethylene is added to the bottom of the reactor vessel by adding solid polyethylene or melting polyethylene and extruding the polyethylene into the vessel in a liquid form. Because the polyethylene is lower density than the Oxidizing Agent phase, the polyethylene (in solid or liquid state) will rise up the reactor 220 if the solid particle or liquid droplet velocity is larger than the downward velocity of the aqueous fluid. As the particles or droplets rise up the reactor 220, they react with the Oxidizing Agent. The concentration of the Oxidizing Agent is lowest at the bottom of the reactor 220 and increases toward the top where fresh "high-concentration" Oxidizing Agent is added. As the solid particles or liquid droplets rise up the reactor 220 they react and the diameter decreases. In addition, as they rise, the Oxidizing Agent concentration increases, increasing the rate, consuming more polyethylene and further reducing the diameter. This counter-current flow reactor maximizes the reaction driving force throughout the reactor. The Product is removed from the bottom of the reactor 220 and any unreacted polyethylene and Reaction Gas is separated and removed separately. Unreacted polyethylene or partially reacted polyethylene can be removed or recycled back to the reactor 220. Additionally, Oxidizing Agent at a specified concentration can be added at different locations within the reactor 220 to increase the Oxidizing Agent concentration.

Figure 9:
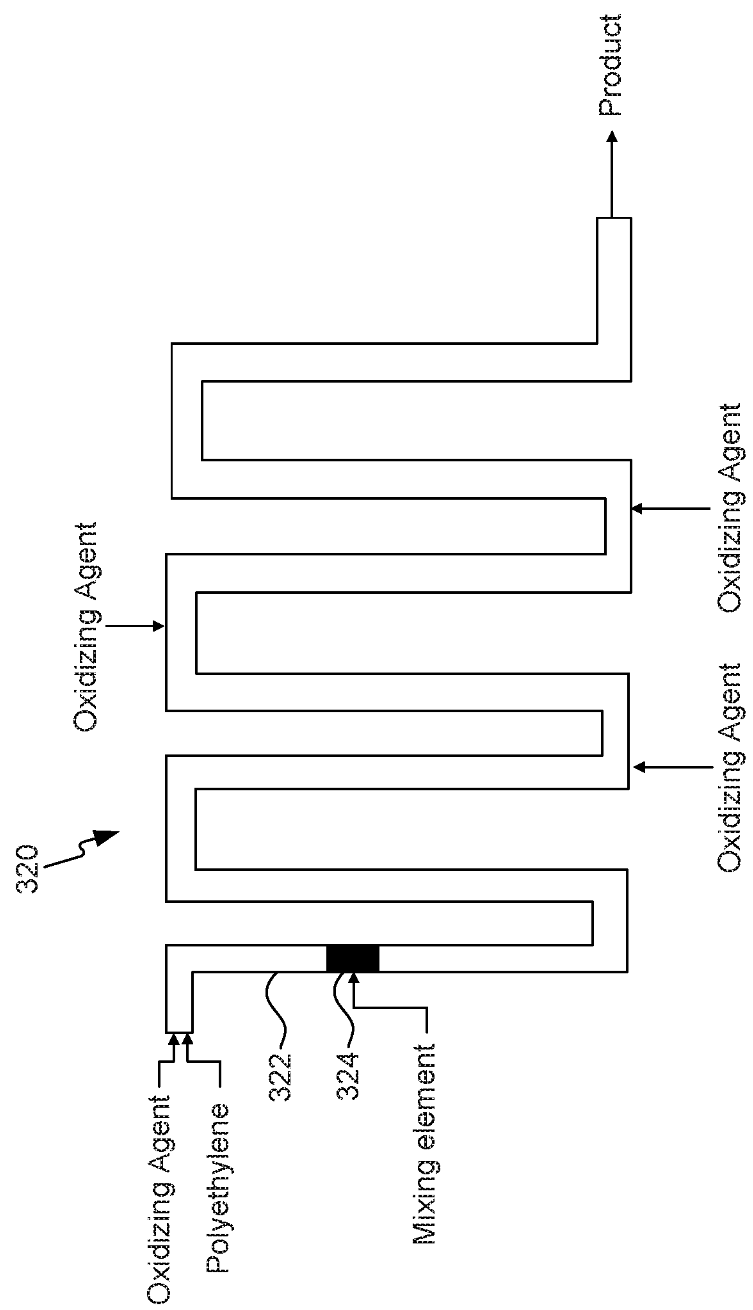
FIG. 9 depicts, in accordance with various embodiments of the invention, a long-residence time plug flow reactor for chemical recycling.

FIG. 9 shows a plug flow reactor 320. Polyethylene and Oxidizing Agent are pumped into a tube 322 where the temperature and pressure are controlled. As the mixture is heated and mixed through turbulence, the polyethylene and Oxidizing Agent react. The mixing may be augmented by using static mixers or other inline mixers 324. The diameter and length of the reactor tube 322 is chosen to meet a specific residence time and also the fluid flow regime. As the fluid mixture moves down the reactor 320 the polyethylene and Oxidizing Agent continue to react. Pumps and knock-out vessels can be added periodically to move the fluid and also remove any Reaction Gas. Additionally, Oxidizing Agent at a specified concentration can be added at different locations within the reactor to increases the Oxidizing Agent concentration.

Figure 10:
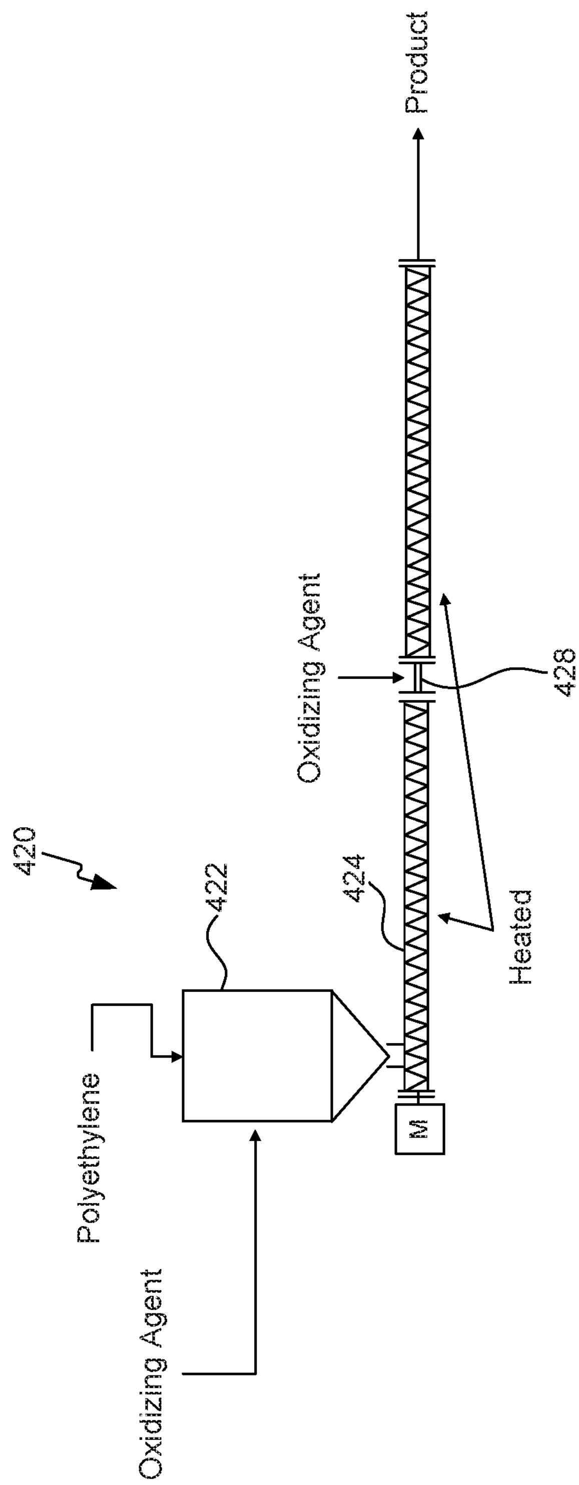
FIG. 10 depicts in, accordance with various embodiments of the invention, a screw reactor for chemical recycling.

FIG. 10 shows a reactor 420 that may be useful for very viscous mixtures (e.g., for feed ratios of 5:1 to 1:2 of polyethylene to Oxidizing Agent on a mass basis) or for polyethylene that has not been pre-treated. Here the polyethylene is added into a hopper 422 with the Oxidizing Agent. This mixture is pulled into the entrance of a reactor tube 424 with a screw auger (single or twin). The auger blades are designed to both mix and convey the mixture down the reactor 420. The reactor walls are heated and as the fluid mixture moves down the reactor the polyethylene and Oxidizing Agent continue to react. The auger can act to mix and breakdown the polyethylene. This reactor system can have multiple sections with breaks 428 that allow for separation of any Reactant Gas and reintroduction of fresh Oxidizing Agent. The fresh Oxidizing Agent could also be added through holes in the reactor walls at specified locations down the length of the reactor tube.

Various materials can be employed for construction of the reactor, impeller, piping and valves (some options include wetted parts to be made of Teflon, hastelloy C, glass reinforced steel, titanium, tantalum, fiberglass reinforced plastic, glass, glass-lined steel). Other variables to be considered include:

Size of the reactor (length and diameter) and pipe sizing.

Temperature of reactor: 50° C. to 300° C.

Pressure of reactor: 10 torr to 10 bar.

Type of reactor (stirred tank, plug flow, slurry).

Mode of operation (batch, semi-batch, continuous).

There may be a reactor train of multiple reactors in parallel or series. These reactors may be of the same or different size and type.

Heating source (induction heating, jacketed with oil, etc.).

Reactor may be insulated or jacketed.

Temperature of the reactor or its heating element may be adjusted; higher temperature ranges may provide harsher conditions to break down polyethylene.

Pressure of the reactor system may be adjusted; higher pressure ranges may increase the rate of reaction and also allow for higher temperatures.

Residence time determines how long the reactants stay in the reactor before exiting. The residence time can range from 30 minutes to 30 hours.

Type of the feedstock and physical form of the feed.

Reflux capacity.

The amount of polyethylene relative to Oxidizing Agent in the feed into the reactor on a mass basis.

5:1 to 1:2 of Polyethylene [mass]:Oxidizing Agent [mass].

1:3 to 1:10 of Polyethylene [mass]:Oxidizing Agent [mass].

1:10 to 1:20 of Polyethylene [mass]:Oxidizing Agent [mass].

1:20 to 1:50 of Polyethylene [mass]:Oxidizing Agent [mass]

1:50 to 1:100 of Polyethylene [mass]:Oxidizing Agent [mass].

1:100 to 1:500 of Polyethylene [mass]:Oxidizing Agent [mass].

The relative amount of polyethylene to the Oxidizing Agent on a mass basis will impact the type of reactor and process. For feed ratios of 1:1 to 1:20, high concentrations of Oxidizing Agent to polyethylene are preferred to keep the reaction rate high and also depolymerize the polyethylene all of the way to a terminal state. For these cases, the reaction mixture could be viscous requiring helical or screw like mixing and conveying parts to move the mixture through the reactor (e.g., screw reactor for chemical recycle in FIG. 10) and fresh Oxidizing Agent may be added at different locations of the reactor to keep the concentrations high and promote the rate of polyethylene breakdown and Product formation. In addition, multiple reactors may be used in series as shown in FIG. 7.

Stirred tank reactors and plug flow reactors are commercially available as units to control chemical reactions.

Separation of Oxidizing Agent From Product Produced From Process to Chemically Recycle Polyethylene In an embodiment during this process, polyethylene is combined with an Oxidizing Agent in a reactor, the polyethylene is broken down and oxidized (sequentially or simultaneously) into Product (e.g. 1 wt % to 20 wt % dicarboxylic acids) water, (e.g. 10 wt % to 90 wt % of aqueous reaction content), and Reaction Gas (e.g. 10 wt % to 60 wt % NO and 40 wt % to 90 wt % $NO_2$). One challenge is that the Product has high miscibility with the Oxidizing Agent at and below the reaction temperature; this can make it difficult to separate Product from the Oxidizing Agent. Additionally, the Oxidizing Agent concentration decreases with increased polyethylene conversion due to the formation of water and Reaction Gas. To make the process economical, Product is separated from the Oxidizing Agent and the Oxidizing Agent should be recycled back to the reactor. This disclosure details solutions to separate the Product and the Oxidizing Agent and to recycle the Oxidizing Agent back to the reactor.

This separation unit is a component of a system for conversion of polyethylene into high value chemicals. In the system, polyethylene is combined with an Oxidizing Agent in a reactor to produce Product in the liquid phase and Reaction Gas. Polyethylene is broken down into Product that can be used for value-adding products (e.g. performance materials, paints and coatings, lubricants, adhesives, fragrances, skincare products, etc.) serving as a drop-in replacement of existing chemical intermediates, or as new chemical intermediates. By combining this separation step to the polyethylene recycling process, it is possible to isolate high value chemicals and to recover the majority of the Oxidizing Agent. The disclosure enables recycling of the Oxidizing Agent and also limits Oxidizing Agent waste generation.

Figure 11:
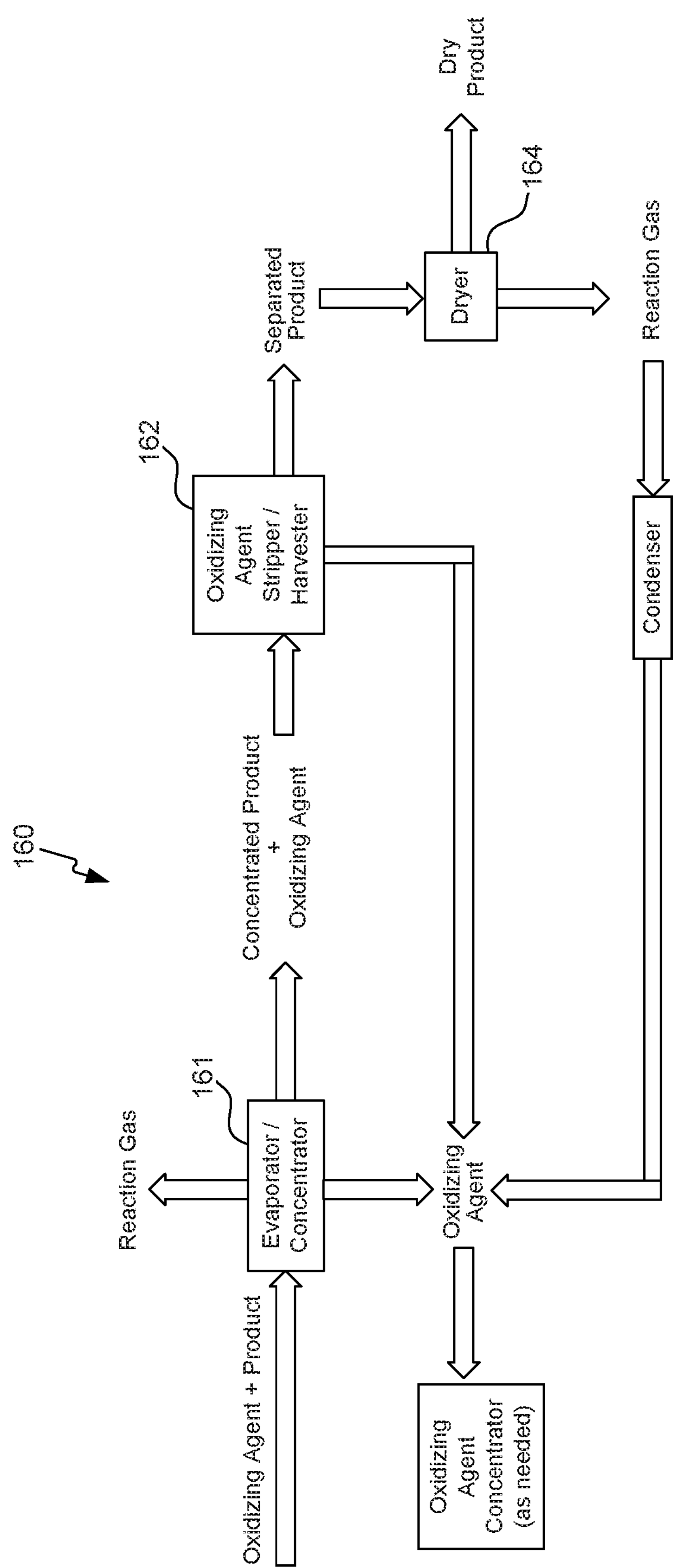
FIG. 11 depicts, in accordance with various embodiments of the invention, a basic separation unit for separation of solid product from aqueous oxidizing agent.

FIG. 11 shows the basic separation unit 160 for polyethylene conversion to Product. Polyethylene conversion products and an Oxidizing Agent exit the reactors of the system in the process and are passed through an evaporator 161 or concentrator (e.g. thin film evaporator) to remove the Oxidizing Agent (e.g. 10 wt % to 80 wt % of reactor stream) from the Product. The concentrated mixture of Product and the Oxidizing Agent is then passed through an Oxidizing Agent stripper/harvester 162 (e.g., a Nutsche filter dryer) to separate Product in solid state and remaining Oxidizing Agent. The separated Product is then passed through a dryer (e.g. spray dryer) 164 to remove residual Oxidizing Agent. All Oxidizing Agent streams generated from the separation process are combined and passed through an Oxidizing Agent concentrator (e.g. a distillation column) as needed, and then recycled back in the reactor section of the polyethylene conversion system to be reused. This component of the system is designed to recover as much as >90% of the Product and >90% of the Oxidizing Agent while minimizing the need to add more Oxidizing Agent to the system.

The evaporator/concentrator 161 can be a thin film evaporator, a centrifugal evaporator, a blow-down evaporator, a vortex evaporator and/or combinations thereof as a single unit of multiple units in series or parallel.

The Oxidizing Agent stripper/harvester 162 can be a chromatography column, a crystallizer, a liquid-liquid extractor, a Nutsche filter dryer, and/or combinations thereof as a single unit or multiple units in a sequence.

The dryer 164 can be a freezer dryer, a spray dryer, a rotary dryer, a centrifugal dryer, a vacuum dryer and/or combinations thereof as a single unit or multiple units in a sequence.

The Oxidizing Agent concentrator can be a distillation column, an absorption column and/or combinations thereof as a single unit or multiple units in a sequence.

The separation unit 160 can have many unique and process-specific features tailored to the processing of Product from polyethylene conversion. It can operate continuously and handle the specific liquid flow and chemical composition out of the reactor. If the Oxidizing Agent after separation from Product is not at the desired concentration then it could be sent to an Oxidizing Agent concentrator (e.g., a distillation column) to be further purified for direct introduction into the reactor.

Another unique application would be to combine the separation unit with an absorption column. Reaction Gas emitted in the separation unit can be combined with Reaction Gas absorption unit to regenerate the Oxidizing Agent for direct introduction into the reactor.

Figure 12:
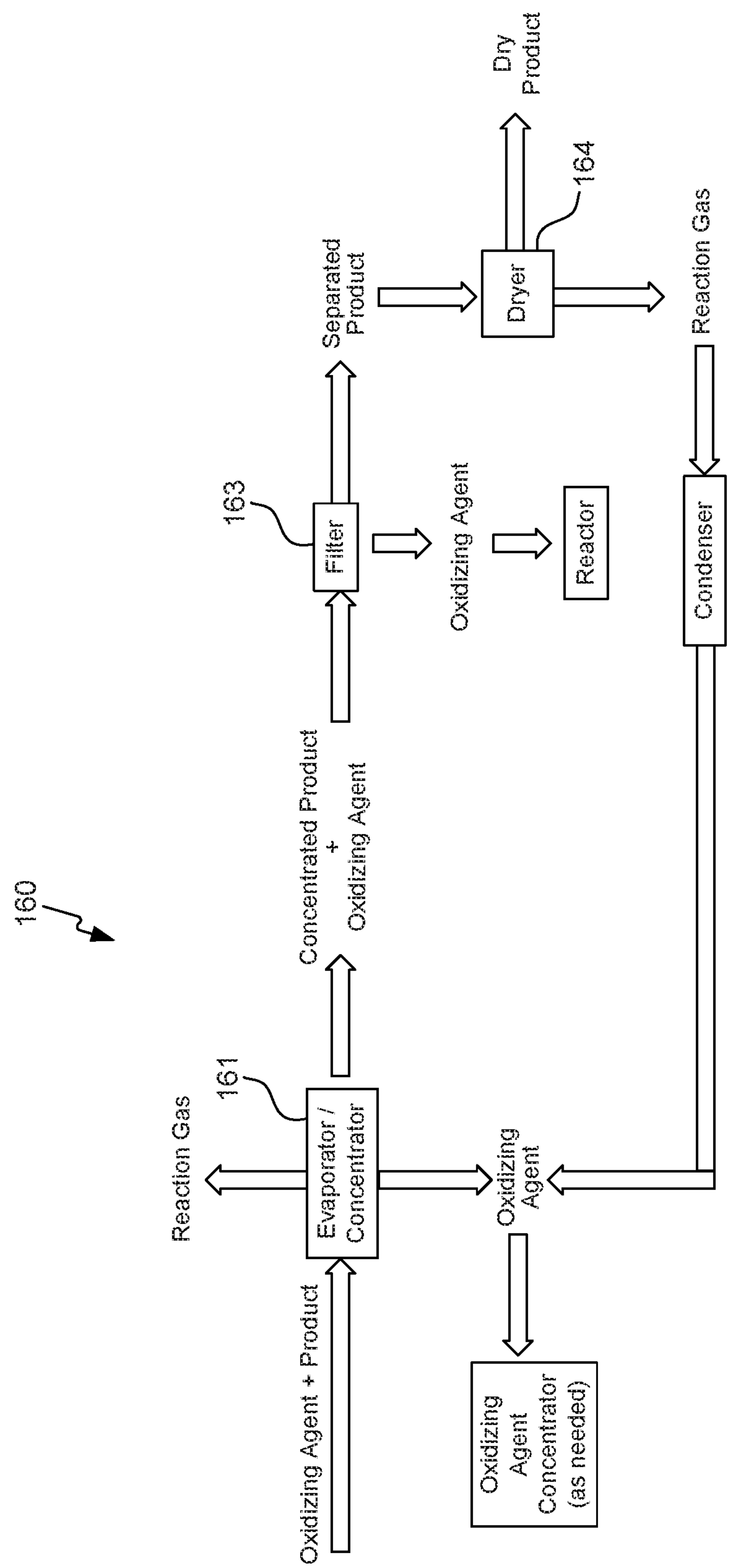
FIG. 12 depicts, in accordance with various embodiments of the invention, a separation unit for separation of solid product from aqueous oxidizing agent.

FIG. 12 shows modifications to separation unit 160. The concentrated Product (e.g. 15 wt % to 80 wt % dicarboxylic acids) and Oxidizing Agent (e.g., 5 wt % to 85 wt % nitric acid) can be passed through a filter 163 (e.g., a Nutsche filter) to collect the Oxidizing Agent and directly introduce the Oxidizing Agent into the reactor for polyethylene conversion. Additionally, in cases where reaction species from incomplete conversion of polyethylene are exiting out of the reactor, filtration step helps to recover such species and the Oxidizing Agent in the filtrate which can be re-introduced into the reactor for further conversion to Product. The filter 163 can be gravity filter, vacuum filter, turbo filter, centrifugal filter, a membrane filter, and/or combinations thereof.

Figure 13:
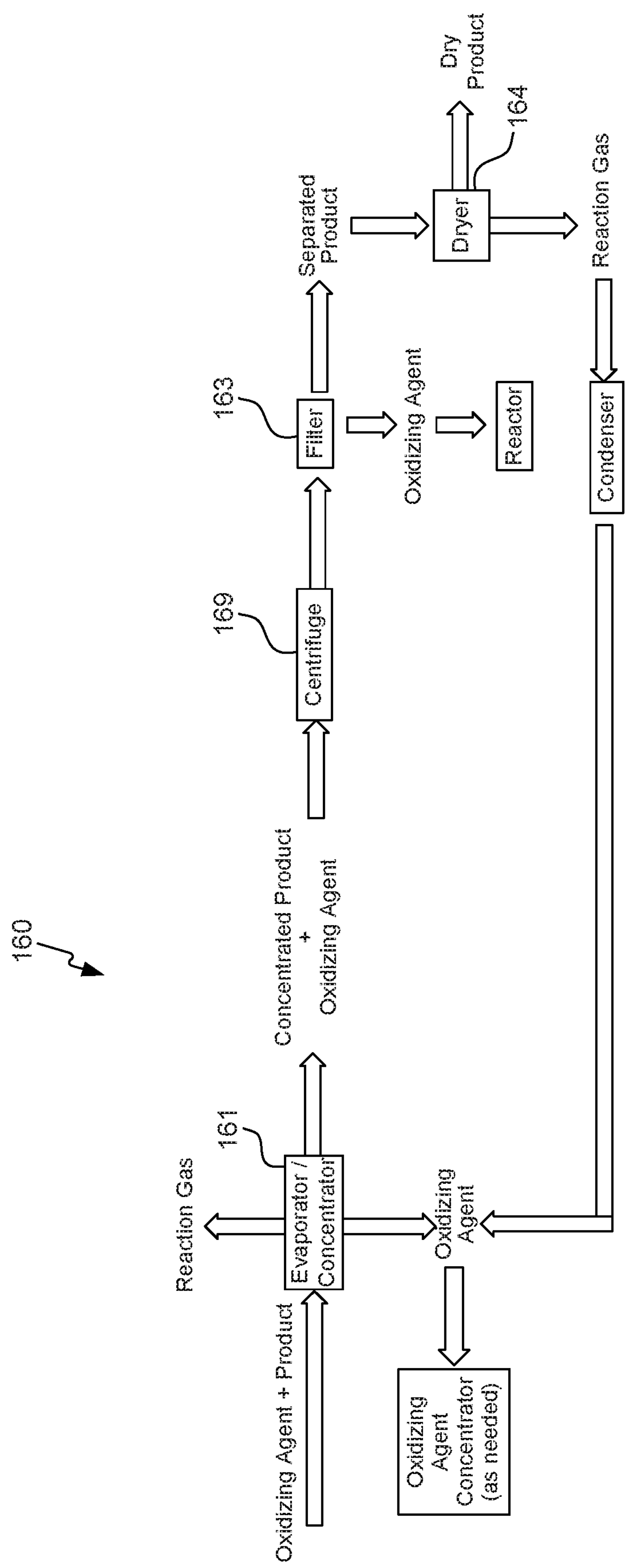
FIG. 13 depicts, in accordance with various embodiments of the invention, a separation unit with centrifugation and filtration and oxidizing agent re-introduction to the reactor.

FIG. 13 shows additional modifications. The concentrated Product (e.g., 15 wt % to 80 wt % dicarboxylic acids) and Oxidizing Agent (e.g., 45 wt % to 95 wt % nitric acid) is first centrifuged 169 and then passed through a filter 163. Centrifugation settles solid particles in the concentrated Product and Oxidizing Agent mixture, minimizes clogging of filter pores and accelerates the filtration process.

Figure 14:
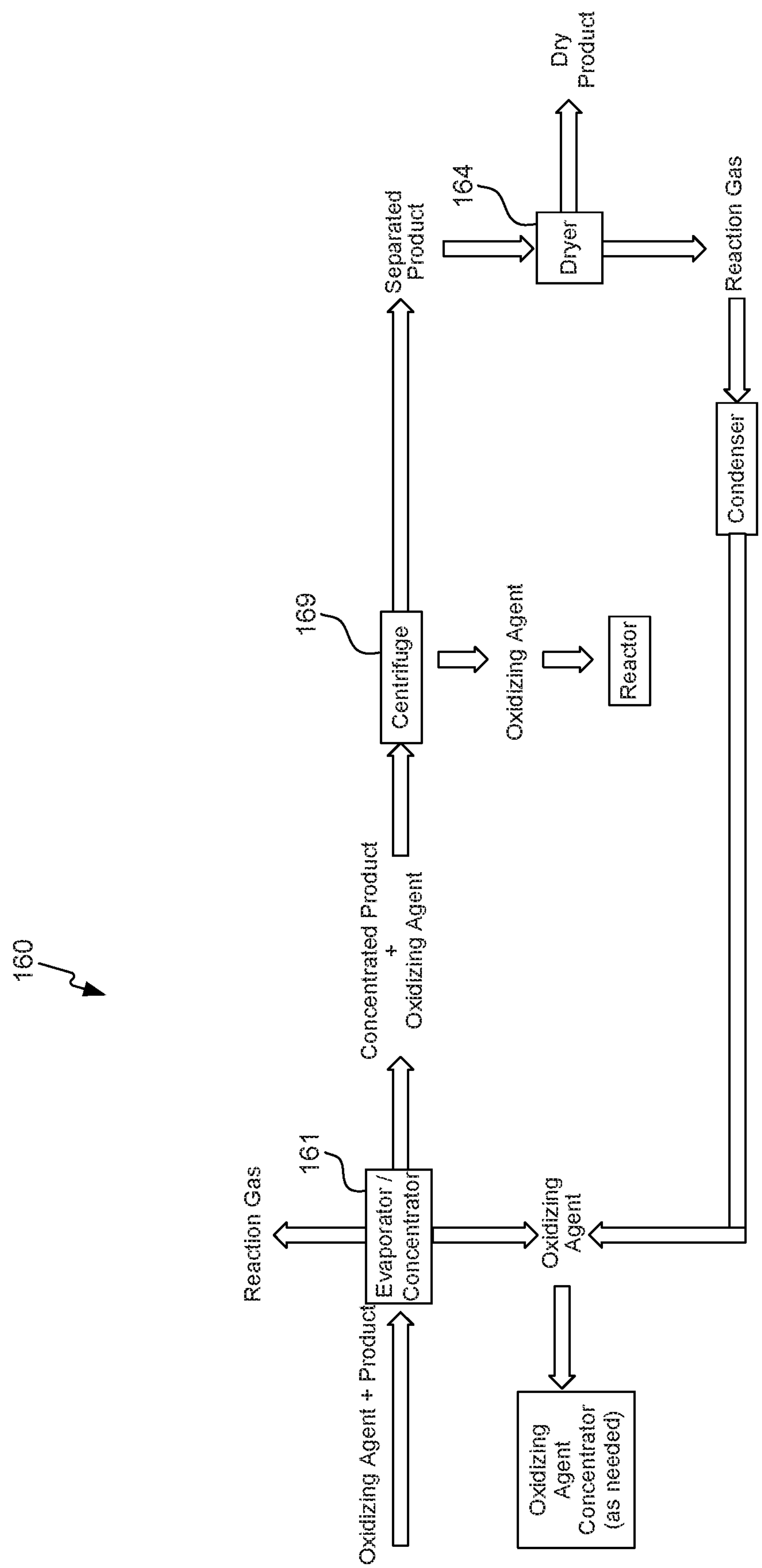
FIG. 14 depicts, in accordance with various embodiments of the invention, a separation unit with centrifugation and oxidizing agent re-introduction to the reactor.

Alternatively, the Oxidizing Agent can be directly collected after centrifugation and directly introduced into the reactor without an additional filtration step as shown in FIG. 14. Centrifugation can also be applied depending on the viscosity of the concentrated Product and Oxidizing Agent mixture. Highly viscous mixtures are difficult to filter and an added step of centrifugation can be highly efficient for separation of Product from the Oxidizing Agent.

FIG. 14 shows the process in FIG. 13 without the filtration step after the centrifugation.

Figure 15:
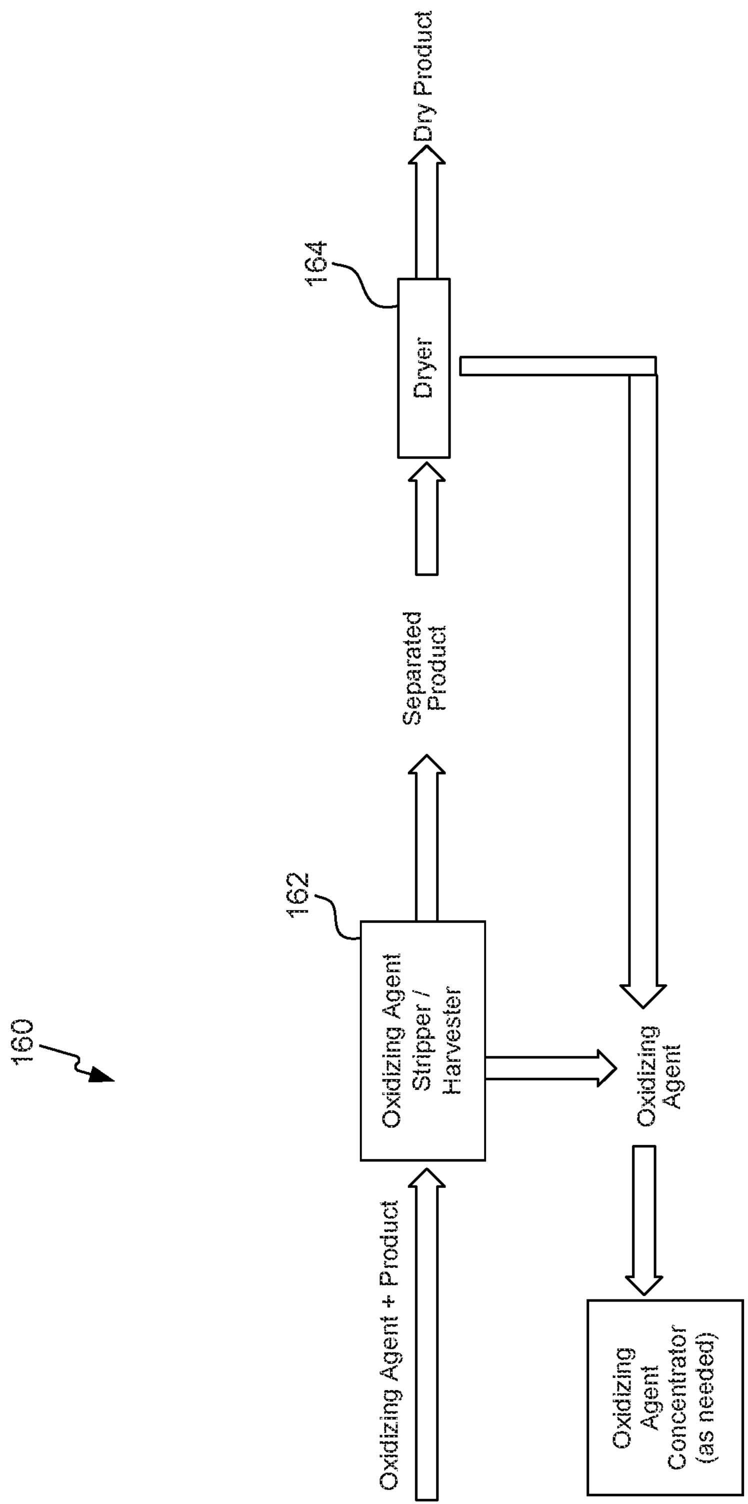
FIG. 15 depicts, in accordance with various embodiments of the invention, a separation unit without evaporation or concentration.

FIG. 15 shows additional modification to FIG. 11. The system eliminates evaporator/concentrator step, as in some cases, it can be combined with the Oxidizing Agent stripper/harvester. In cases where loss of Oxidizing Agent from separation is low, extra equipment for Oxidizing Agent and Product recovery may not be required and completely eliminated or possibly combined in a single step.

Figure 16:
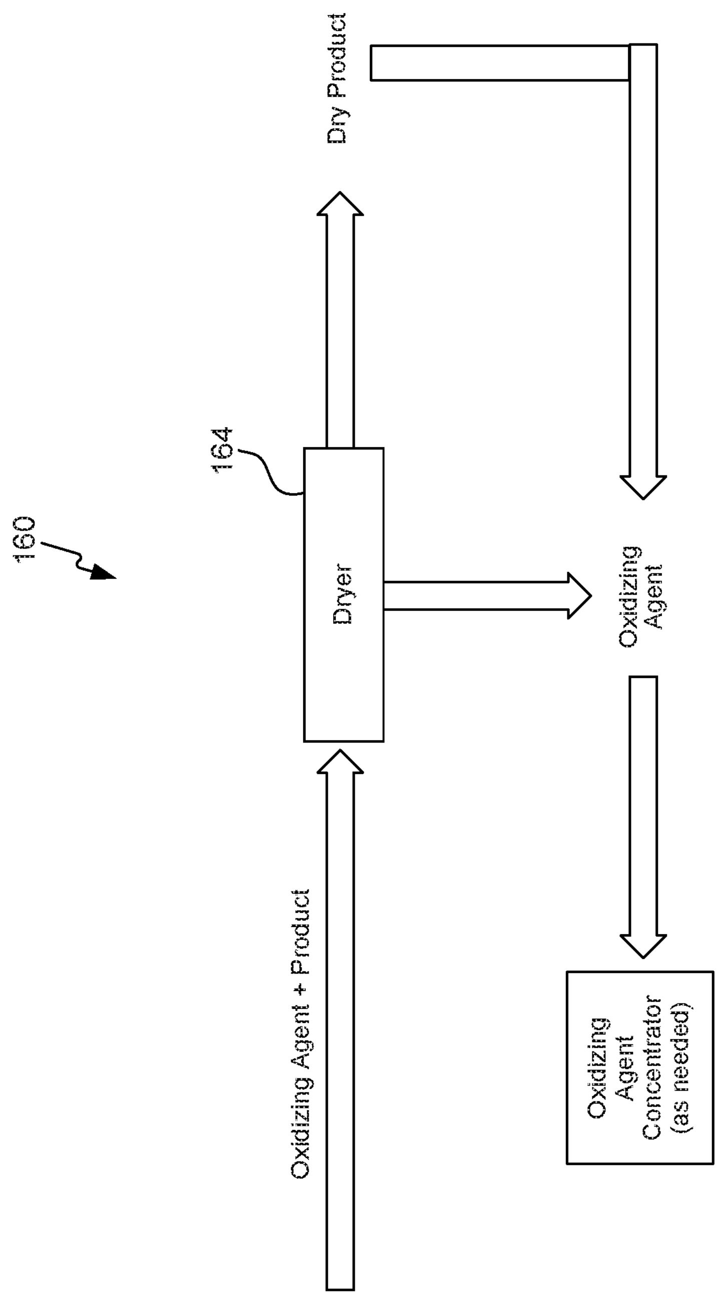
FIG. 16 depicts, in accordance with various embodiments of the invention, a separation unit for direct separation to product and oxidizing agent.

FIG. 16 shows a separation unit 160 with a dryer 164 (e.g., a spray dryer) to directly obtain dry Product (e.g. 90 wt % to 99.9 wt % dicarboxylic acids) and Oxidizing Agent (e.g., 45 wt % to 95 wt % nitric acid) in a single step. Rapid drying of liquid stream out of the reactor can be achieved by blowing hot air into the stream to remove most of the Oxidizing Agent. This method can be applied for liquid streams with low viscosity that can be easily dispersed into controlled size small droplets.

Figure 17:
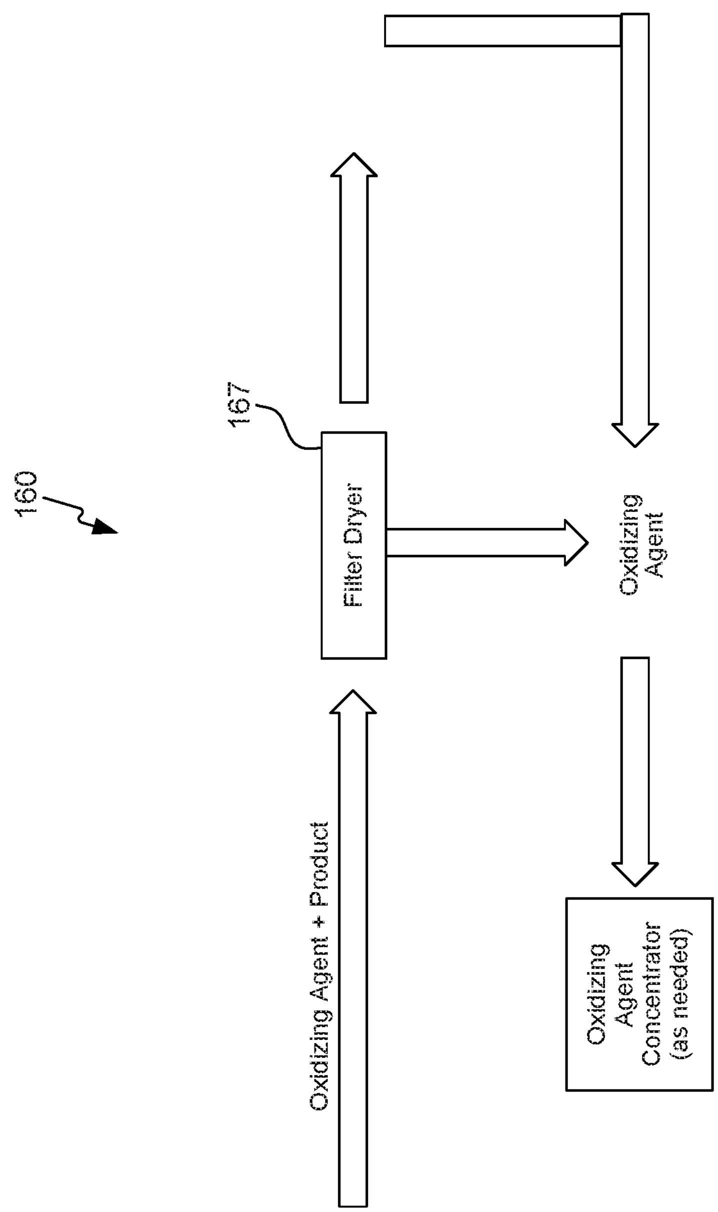
FIG. 17 depicts, in accordance with various embodiments of the invention, a separation unit with combined filtration and drying in a single step.

FIG. 17 shows separation unit 160 with combined filtration and drying in a single step. This can be accomplished with a filter dryer 167 (e.g., a Nutsche filter) at a desired temperature and can be operated either under vacuum or at pressure. The method can be used with or without agitation depending on required drying rate. Faster drying is possible with agitation and changing the speed of agitation. Vacuum filtration can also be applied for faster drying. Other variables include:

- polyethylene processed liquid stream flow rate into the evaporator/concentrator.
- Residence time of liquid stream in the evaporator. This can be modified to alter the amount of Oxidizing Agent removal and may also be modified depending on the flow rate of liquid stream out of the reactor.
- The temperature of the evaporator/concentrator (e.g. thin film evaporator) may be adjusted to adjust evaporation rate required based on flow rate out of the reactor and into the separation unit. Faster flow rate out of the reactor would require higher temperature and slower flow rate out of the reactor would require lower temperature.
- The pressure of the evaporator/concentrator. Faster evaporation can be achieved at lower temperature with reduced pressure and at higher temperature with higher pressure. Operating the evaporator/concentrator at reduced or increased pressure may add extra cost and potentially other pieces of equipment.
- The evaporator/concentrator can be a single unit for cumulative removal of Oxidizing Agent or multiple units for sequential removal of the Oxidizing Agent
- Oxidizing Agent stripper/harvester may be at ambient or reduced pressure. Reduced pressure improves filtration rates but this adds cost and potentially other pieces of equipment like vacuum pumps.
- Temperature and pressure of the dryer.
- Temperature of the condenser.
- Speed of the centrifuge.
- Temperature and pressure of the Oxidizing Agent concentrator. Faster evaporation can be achieved at lower temperature with reduced pressure and at higher temperature with higher pressure.
- Pore size of the filter.
- Materials of construction for evaporator/concentrator, filter, dryer, distillation, Oxidizing Agent stripper/harvester, centrifuge (some options include wetted parts to be made of Teflon, hastelloy C, glass reinforced steel, titanium, tantalum, fiberglass reinforced plastic, glass, glass-lined steel).
- Heating source for evaporator/concentrator, distillation/dryer, Oxidizing Agent stripper/harvester (induction heating, jacketed with oil).

Oxidizing Agent Recovery and Regeneration for Polyethylene Chemical Recycling

In an embodiment of this process, Reaction Gas is formed after the Oxidizing Agent oxidizes the polyethylene. Commercially, nitric acid is produced from absorption of $NO_x$—generated from ammonia—into water, using absorption column in continuous mode of operation. These plants are typically designed to produce significant volumes of nitric acid and thus, the absorption columns are tailored to this application. We are currently not aware of this technology being applied to polyethylene recycling. Furthermore, many features of the chemical recycling process are unique. In addition to Oxidizing Agent recovery, the Reaction Gas is reduced to below a threshold level, as defined by state or regional regulations, to be released into the environment. The absorption column may be capable of reducing the Reaction Gas composition to these levels.

This absorption/reaction unit is a component of a chemical recycling system. In the system, polyethylene is combined with an Oxidizing Agent in a reactor to produce Product in the liquid phase and a Reaction Gas. The Reaction Gas can be absorbed in water and reacted and converted back into Oxidizing Agent. By combining this absorption step to the chemical recycling process it is possible to recover the majority of the produced Reaction Gas enabling recycle of the Oxidizing Agent and also limiting emission of Reaction Gas out of the process. The tail gases out of the process are scrubbed gases (e.g. <1 wt % NO and <1 wt % $NO_2$).

Figure 18:
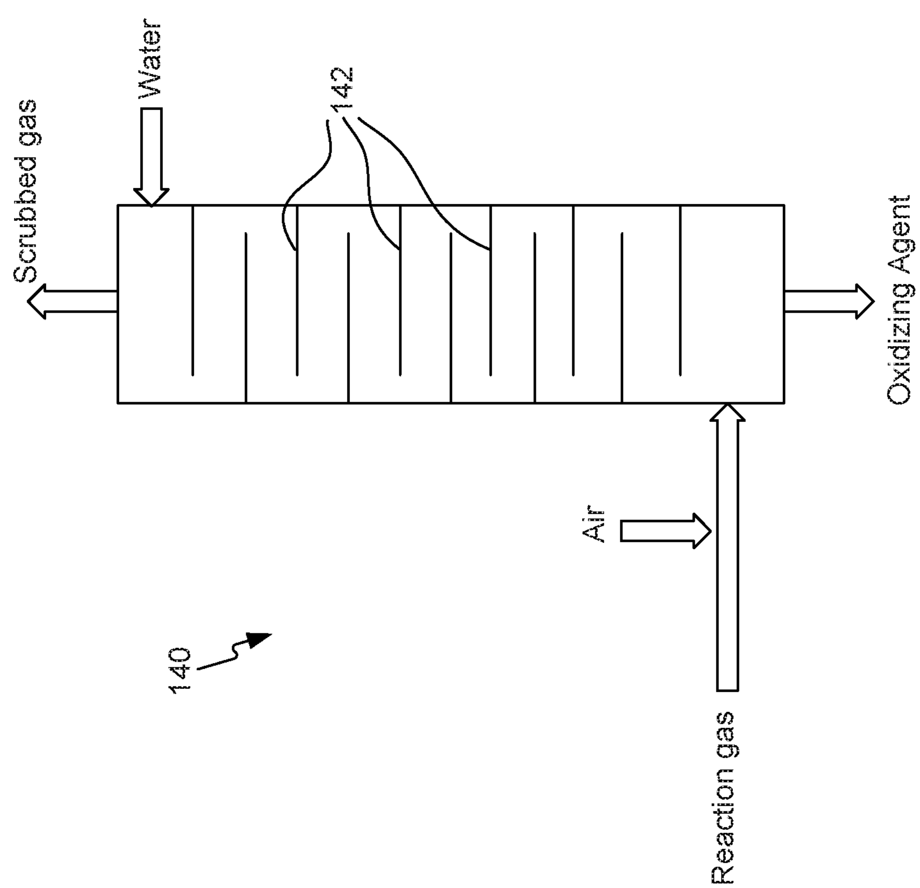
FIG. 18 depicts, in accordance with various embodiments of the invention, a basic absorption unit for reaction gas capture and conversion back into oxidizing agent.

FIG. 18 shows the basic absorption unit 140 for polyethylene chemical recycling. The Reaction Gas (e.g. 10-60 wt % NO and 40-90 wt % $NO_2$) exits the reactor and other process units and are combined and then mixed with air, enriched air, or oxygen to convert the Reaction Gas into an oxidized state (e.g. conversion of NO to $NO_2$). The gases then flow into and are distributed at the bottom of an absorption column 140. The Reaction Gas flows up the column that has internals 142 (trays or other packing) to enhance contacting area and transport of the Reaction Gas into the aqueous phase to reach equilibrium at all positions within the system. Pure water is added at the top of the absorption column 140 and absorbs the Reaction Gas that react and transform into the Oxidizing Agent (e.g. NO, $NO_2$, $N_2O_3$, and $N_2O_4$ react with water to form $HNO_3$) continually becoming more concentrated in Oxidizing Agent as it traverses toward the column bottom. At the bottom of the column 140, the Oxidizing Agent can reach high concentrations (e.g. 40 wt % to 70 wt % $HNO_3$). The Oxidizing Agent is then recycled back in the reactor section of the chemical recycling system to be reused. This component of the system is designed to recover as much as 99.9% of the Reaction Gas and convert back into Oxidizing Agent to minimize the need to add more Oxidizing Agent into the system. The high recovery rate also permits the scrubbed gas to be emitted to the atmosphere if the concentration of Reaction Gas is low enough.

For example, the Reactor Gas may exit the reactor with a composition of 50 mol % NO and 50 mol % $NO_2$. If this flows at 1 kmol per hour then 0.5 kmol of NO can be oxidized to $NO_2$. Air with a flow rate of greater than or equal to 1.7 kmol per hour to be mixed with this Reaction Gas stream to provide sufficient oxygen to oxidize the NO. After the NO is oxidized to $NO_2$ the mixed stream will have $N_2$ and mostly $NO_2$ (and other lower concentration species found in air). The stream will have ~1 kmol per hour of $NO_2$ and ~1.35 kmol per hour of $N_2$. The mixed stream will be sent through the absorption column 140 and the $NO_2$ will absorb into the water in the column ultimately converting the majority of the $NO_2$ back into the Oxidizing Agent (e.g. converting the $HNO_3$ into a flow rate of 1 kmol per hour). The flow rate of the water is chosen to maximize the concentration of $HNO_3$ in the aqueous phase.

The absorption column 140 can have many unique and process specific features tailored to the polyethylene recycling process. It can operate continuously and handle the specific Reaction Gas composition out of the reactor (e.g. 60 wt % to 99 wt % $NO_2$ and 10 wt % to 60 wt % NO). In addition, less concentrated Oxidizing Agent from other parts of the process may be added to the column at intermediate stages. If the concentration of the Oxidizing Agent exiting the absorption column 140 is not high enough for the process (i.e., the concentration needed for the reactor) then it could be sent to an additional separation unit (like a distillation column) to be further purified.

Figure 19:
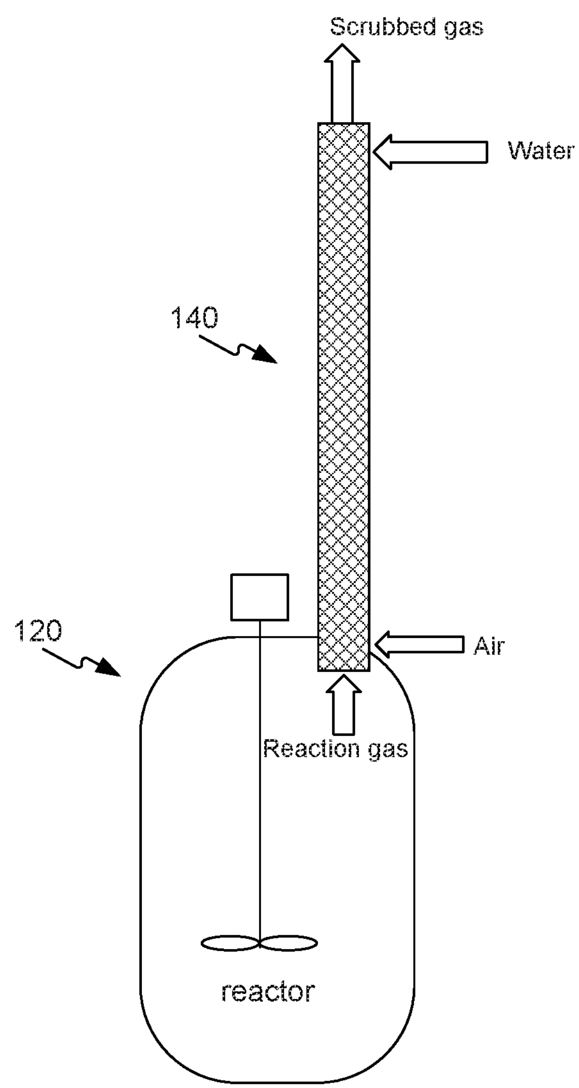
FIG. 19 depicts, in accordance with various embodiments of the invention, a hybrid reactor-absorption unit.

FIG. 19 shows another unique application, which combines the absorption column 140 with the reactor 120. In this system, the absorption column 140 would serve multiple functions. Since the fluid in the reactor 120 is at the boiling point and both Reaction Gas and Oxidizing Agent exit the reactor 120 in the gas phase, a reflux component is necessary to re-condense the vaporized Oxidizing Agent. By adding an absorption column 140 with cold water on the top, it is possible for the absorption column 140 to perform two functions: absorption of the Reaction Gas and direct condensation of the vaporized Oxidizing Agent.

Figure 20:
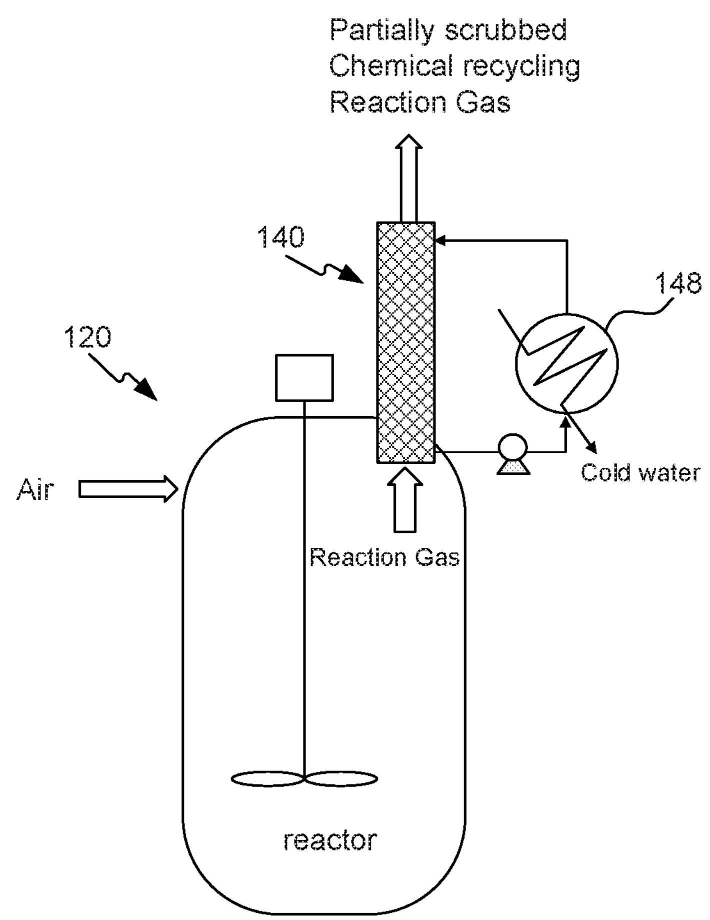
FIG. 20 depicts, in accordance with various embodiments of the invention, a catalyst gas scrubbing reflux condenser.

FIG. 20 shows another modification would be to perform partial absorption in the reflux section of the reactor. Here a packed column 140 is located on the top of the reactor 120. Near the bottom of the column 140 there is a tray or some internal to partially remove condensed liquid for the column. This liquid is pumped through a cooler 148 to further reduce the temperature (e.g., 90° C. to 150° C.) and then is sprayed from the top of the column 140 onto packing material within the column 140. The Reaction Gas exiting the reactor 120 is cooled and the vaporized Oxidizing Agent re-condenses and drains back into the reactor 120. Because Oxidizing Agent is being consumed, the concentration in the reactor 120 and vapor is less than the concentration of the Oxidizing Agent in the feed, so some Reaction Gas will be absorbed. This will reduce the amount of Reaction Gas going to the next section and also help to keep the Oxidizing Agent concentration high.

Other variables include:

The temperature of the water and Reaction Gas may be adjusted prior to entering the absorption column or cooled within the column (e.g. 5° C. to 50° C.). Typically, the colder the fluids the better the recovery and conversion to Oxidizing Agent.

Pressure may also be adjusted. High pressure improves recovery and separations, but this adds cost and potentially other pieces of equipment, like compressors.

Relative flow rates of the Reaction Gas to the water. These flow rates will impact the composition of the scrubbed gas and the aqueous Oxidizing Agent.

The length of the column and the diameter.

The internals and packing of the column.

Number of columns.

Location in the column where streams are added.

Definitions and Embodiments

Oxidizing Agent: chemical component(s) used to enable the reaction

The Oxidizing Agent comprises at least one selected from the group consisting of nitric acid, sulfuric acid, hydrogen peroxide, molecular oxygen, ozone, and combinations thereof.

In some embodiments, the Oxidizing Agent comprises at least one selected from the group consisting of aqueous nitric acid, aqueous sulfuric acid, aqueous hydrogen peroxide, molecular oxygen, ozone, and combinations thereof.

In some embodiments, the Oxidizing Agent comprises aqueous nitric acid.

In some embodiments, the Oxidizing Agent comprises 45-95 wt % aqueous nitric acid.

In some embodiments, the Oxidizing Agent comprises 50-75 wt % aqueous nitric acid.

In some embodiments, the Oxidizing Agent comprises 60-70 wt % aqueous nitric acid.

In some embodiments, the Oxidizing Agent comprises 70-80 wt % aqueous nitric acid.

Catalyst: chemical component(s) used to enhance the reaction.

The Catalyst comprises at least one selected from the group consisting of hydrochloric acid, hydrobromic acid, zinc oxide, titanium oxide, zirconium oxide, niobium oxide, zeolite, alumina, silico-alumino-phosphate, iron carbonate, calcium carbide, sulfated zirconia, and combinations thereof.

In some embodiments, the Catalyst comprises zeolite.

In some embodiments, the Catalyst comprises ZSM-5 zeolite.

In some embodiments, the Catalyst comprises alumina.

In some embodiments, the Catalyst comprises hydrochloric acid.

Polyethylene: feedstock(s) for the reaction.

Polyethylene comprises at least one selected from the group consisting of very low density polyethylene, low density polyethylene, linear low density polyethylene, medium density polyethylene, cross-linked polyethylene, high density polyethylene, high density cross-linked polyethylene, high molecular weight polyethylene, ultra-low molecular weight polyethylene, ultra-high molecular weight polyethylene, and combinations thereof.

In some embodiments, Polyethylene comprises at least one selected from the group consisting of low density polyethylene, linear low density polyethylene, high density polyethylene, and combinations thereof.

In some embodiments, Polyethylene is from a waste source.

In some embodiments, Polyethylene has at least one contaminant selected from the group consisting of pigments, additives, dirt, grease, debris, glass, paper, fluids, and combinations thereof.

In some embodiments, Polyethylene may be in the form of at least one selected from the group consisting of films, flakes, shreds, powders, rigids, resins, melts, and combinations thereof.

Reaction Gas: gas(es) produced during the reaction

Reaction Gas comprises at least one selected from the group consisting of $N_2$, $O_2$, Ar, $CO_2$, $H_2O$, CO, NO, $NO_2$, $N_2O$, $N_2O_3$, $N_2O_4$, $N_2O_5$, $HNO_3$, $SO_2$, $SO_3$, $Cl_2$, $Br_2$, VOCs, and combinations thereof.

In some embodiments, Reaction Gas comprises $NO_2$, NO, $HNO_3$, CO, $CO_2$, and $H_2O$.

In some embodiments, Reaction Gas comprises 10 to 60 wt % NO and 40 to 90 wt % $NO_2$.

In some embodiments, Reaction Gas comprises 10 to 60 wt % NO and 60 to 99 wt % $NO_2$.

In some embodiments, Reaction Gas comprises 10 to 40 wt % NO, 40 to 99 wt % $NO_2$, 0 to 10 wt % CO, 0 to 5 wt % $CO_2$, 0 to 10 wt % $HNO_3$, and 0 to 10 wt % $H_2O$. In some embodiments, Reaction Gas comprises 10 to 40 wt % NO, 40 to 99 wt % $NO_2$, 0 to 10 wt % CO, 0 to 5 wt % $CO_2$, 0 to 10 wt % $HNO_3$, 0 to 10 wt % $H_2O$, and 0 to 10 wt % VOCs.

Product: Harvestable Chemical Output(s) From the Reaction

Product comprises at least one selected from the group consisting of C2 dicarboxylic acid, C3 dicarboxylic acid, C4 dicarboxylic acid, C5 dicarboxylic acid, C6 dicarboxylic acid, C7 dicarboxylic acid, C8 dicarboxylic acid, C9 dicarboxylic acid, C10 dicarboxylic acid, C11 dicarboxylic acid, C12 dicarboxylic acid, C13 dicarboxylic acid, C14 dicarboxylic acid, C15 dicarboxylic acid, C16 dicarboxylic acid, C17 dicarboxylic acid, C18 dicarboxylic acid, C19 dicarboxylic acid, C20 dicarboxylic acid, C20+ dicarboxylic acid, C2 monocarboxylic acid, C3 monocarboxylic acid, C4 monocarboxylic acid, C5 monocarboxylic acid, C6 monocarboxylic acid, C7 monocarboxylic acid, C8 monocarboxylic acid, C9 monocarboxylic acid, C10 monocarboxylic acid, C11 monocarboxylic acid, C12 monocarboxylic acid, C13 monocarboxylic acid, C14 monocarboxylic acid, C15 monocarboxylic acid, C16 monocarboxylic acid, C17 monocarboxylic acid, C18 monocarboxylic acid, C19 monocarboxylic acid, C20 monocarboxylic acid, C20+ monocarboxylic acid, and combinations thereof.

In some embodiments, Product comprises at least one selected from the group consisting of succinic acid, glutaric acid, adipic acid, pimelic acid, azelaic acid, or the salts or esters thereof, and at least one of oxalic acid, suberic acid, sebacic acid, undecanedioic acid, dodecanedioic acid, tridecanedioic acid, tetradecanedioic acid, pentadecanedioic acid, 2-octenedioic acid, 2-nonenedioic acid, 2-decenedioic acid, and 2-undecenedioic acid, and salts, esters, and combinations thereof.

In some embodiments, Product comprises at least one selected from the group consisting of 5-50% succinic acid, 5-50% glutaric acid, 5-50% adipic acid, 5-50% pimelic acid, 0-30% suberic acid, 0-30% azelaic acid, 0-20% sebacic acid, 0-10% undecanedioic acid, 0-10% dodecanedioic acid, and combinations thereof.

In some embodiments, Product comprises at least one selected from the group consisting of succinic acid, glutaric acid, adipic acid, pimelic acid, and azelaic acid, sebacic acid, and combinations thereof.

In some embodiments, Product further includes at least one of $C_8$-$C_{20}$ dicarboxylic acid substituted with a single nitro group, or the salts or esters thereof. In some embodiments, the $C_8$-$C_{20}$ dicarboxylic acid substituted with a single nitro group may be nitro-suberic acid, nitro-azelaic acid, nitro-sebacic acid, nitro-undecanedioic acid, nitro-dodecanedioic acid, nitro-brassylic acid, nitro-tetradecanedioic acid, nitro-pentadecanedioic acid, nitro-hexadecanedioic acid, nitro-heptadecanedioic acid, nitro-octadecanedioic acid, nitro-nonadecanedioic acid, and nitro-icosanedioic acid, or the salts or esters thereof. In some embodiments, the $C_8$-$C_{20}$ dicarboxylic acid is 2-nitro-suberic acid, 2-nitro-azelaic acid, 2-nitro-sebacic acid, 2-nitro-undecanedioic acid, 2-nitro-dodecanedioic acid, 2-nitro-brassylic acid, 2-nitro-tetradecanedioic acid, 2-nitro-pentadecanedioic acid, 2-nitro-hexadecanedioic acid, 2-nitro-heptadecanedioic acid, 2-nitro-octadecanedioic acid, 2-nitro-nonadecanedioic acid, or 2-nitro-icosanedioic acid, or the salts or esters thereof.

In some embodiments, Product comprises nitrated carboxylic acids. Product may include at least one of 2-nitro-suberic acid, 2-nitro-azelaic acid, 2-nitro-sebacic acid, 2-nitro-undecanedioic acid, 2-nitro-dodecanedioic acid, 2-nitro-brassylic acid, 2-nitro-tetradecanedioic acid, 2-nitro-pentadecanedioic acid, 2-nitro-hexadecanedioic acid, 2-nitro-heptadecanedioic acid, 2-nitro-octadecanedioic acid, 2-nitro-nonadecanedioic acid, and 2-nitro-icosanedioic acid, or the salts or esters thereof.

In some embodiments, at least one species in the Product may be a chemical intermediate for industrial applications.

It should be understood that this invention is not limited to the particular methodologies, protocols, and reagents, etc., described herein and as such can vary therefrom. The terminology used herein is for the purpose of describing particular embodiments only, and is not intended to limit the scope of the present invention, which is defined solely by the claims.

EXAMPLES

The invention is further illustrated by the following examples which are intended to be purely exemplary of the invention, and which should not be construed as limiting the invention in any way. The following examples are illustrative only, and are not intended to limit, in any manner, any of the aspects described herein. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

The feedstock for Example 1 was contaminated plastic film from a material recovery facility. The composition of these films includes LDPE, HDPE, as well as a miscellaneous category that was not identified. The contaminated plastic film was cut into 2-inch sized squares and strips.

5 grams of feedstock was placed into a glass lined reactor. 75 mL of 20% nitric acid, diluted with water, was added to the reactor and the plastics were submerged in the liquid solution. The reactor was sealed, pressurized with air (600 psi), and heated while the contents were stirred at 500 rpm. Once the desired temperature (120° C.) was reached, the reaction was timed for 2 hours. Then, the reactor was allowed to cool to room temperature while stirring continued.

After the pressure was released, 30 mL of acetone was added to the reactor and stirred for another 10 minutes to help the remaining solid pieces detach from the stirrer. The contents of the reactor were filtered through filter paper, removing the solids, which is an oligomeric resin. 50 mL of 5M NaOH was added to the liquid, achieving pH 12-13. A precipitate is formed and collected via filter paper; this is the NaOH product. To the remaining liquid, 4 mL of 10M HCl was added, achieving pH 2. A precipitate is formed. The solution was placed at 4 C for 30 minutes to allow more precipitation. This precipitate was also collected via filter paper; this is the HCl product. The remaining filtrate was evaporated completely by boiling on a hot plate. 20 mL acetone was added to the dried crystals. The medium was mixed by vortexing. The non-dissolved crystals were removed via filter paper. The remaining clear filtrate was placed at 50° C. overnight to allow slow evaporation. Finally, the dried solids were collected; this is the acetone product.

TABLE 1

Data According to Example 1.

| Oligomers (% yield by weight) | NaOH product (% yield by weight) | HCl product (% yield by weight) | Acetone product (% yield by weight) | Succinic acid (ppm) | Glutaric acid (ppm) | Adipic acid (ppm) | Pimelic acid (ppm) | Crude acids (% yield by weight) |
|---|---|---|---|---|---|---|---|---|
| 28 | 43 | 16 | 16 | 14 | 19 | 13 | 19 | 48 |

Examples 2a-2d

The feedstock for Examples 2a-2d was contaminated plastic film from a material recovery facility. The composition of these films includes LDPE, HDPE, as well as a miscellaneous category that was not identified. The contaminated plastic film was cut into 2-inch sized squares and strips.

X grams of feedstock was placed into a glass lined reactor. Y mL of 20% or 25% nitric acid was added to the reactor and the plastics were submerged in the liquid solution. The reactor was sealed, pressurized with air (600 psi), and heated. Once the desired temperature (120° C.) was reached, the reaction was timed for 2 hours. After the first hour, stirring (500 rpm) was implemented and continued for the rest of the reaction. Then, the reactor was allowed to cool to room temperature while stirring continued. (See Table 2 below for specific numeric values for X and Y used in Examples 2a-2d.).

After the pressure was released, the solid phase was separated from the liquid phase by filtration. The solid phase was air dried while the liquid phase was heated on a hot plate. The solid phase contains the oligomers. To avoid burning or charring the remains of the liquid phase, the solution was removed from the heat source and allowed to air dry until all liquid is gone. This remaining product contains the crude dicarboxylic acids.

TABLE 2

Data According to Examples 2a-2d.

| Example No. | Feedstock mass (g) | Nitric acid (volume, concentration) | Oligomers (% yield by weight) | Crude acids (% yield by weight) |
|---|---|---|---|---|
| 2a | 5 | 75 mL, 20% | 87 | 24 |
| 2b | 9 | 135 mL, 25% | 66 | 41 |
| 2c | 8 | 120 mL, 25% | 83 | 27 |
| 2d | 12 | 180 mL, 25% | 70 | 50 |

Example 3

The feedstock for Example 3 was LDPE bubble packaging film. The LDPE bubble packaging film was cut into 2-inch sized squares and strips.

5 grams of feedstock was placed into a glass lined reactor. 75 mL of 20% nitric acid, diluted with water, was added to the reactor and the plastics were submerged in the liquid solution. The reactor was sealed, pressurized with air (600 psi), and heated; the stirrer was not used. Once the desired temperature (120° C.) was reached, the reaction was timed for 2 hours. Then, the reactor was allowed to cool to room temperature.

This example (i.e., Example 3) followed the same product collection method as described in Example 2.

TABLE 3

Data According to Example 3.

| Oligomers (% yield by weight) | Crude acids (% yield by weight) |
|---|---|
| 67 | 26 |

Example 4

The feedstock for Example 4 was HDPE pellets, each with a 0.5 cm diameter. The reaction and product collection procedures are as described in Example 3.

TABLE 4

Data According to Example 4.

| Oligomers (% yield by weight) | Crude acids (% yield by weight) |
|---|---|
| 88 | 32 |

Examples 5a-5c

The feedstock for Examples 5a-5c was contaminated plastic film from a material recovery facility. The composition of these films includes LDPE, HDPE, as well as a miscellaneous category that was not identified. The surface contamination included dirt, debris, food residue, and greases. These films were shredded into non-uniform pieces with average size 20 cm×20 cm.

X grams of feedstock was placed into a round bottom flask. Y mL of 69% nitric acid was added to the flask; the plastics were submerged in the liquid solution. The bottom of the flask was heated in a heating mantle; the opening of the flask was connected to a condenser. A stir bar was used to agitate the contents. Once the desired temperature (120° C.) was reached, the reaction was timed for Z hours. Then, the flask was allowed to cool to room temperature while stirring continued. (See Table 5 below for specific numeric values for X, Y and Z used in Examples 5a-5c.).

Subsequently, filtration via filter paper was performed to separate the oligomeric resin from the liquid solution. The liquid solution was heated to 130° C. for 60 minutes to remove the nitric acid. The remaining crystalline solid comprised the dicarboxylic acid products.

TABLE 5

| Data According to Examples 5a-5c. | | | | | |
|---|---|---|---|---|---|
| Example No. | Feedstock mass (g) | Nitric acid volume (mL) | Reaction time (hours) | Oligomers (% yield by weight) | Crude acids (% yield by weight) |
| 5a | 15 | 60 | 6 | 76 | 31 |
| 5b | 30 | 105 | 12 | 79 | 34 |
| 5c | 30 | 150 | 24 | 51 | 70 |

Examples 6a-6d

The feedstock for Examples 6a-6d was contaminated plastic film from a material recovery facility. The composition of these films includes LDPE, HDPE, as well as a miscellaneous category that was not identified. The surface contamination included dirt, debris, food residue, and greases. These films were shredded into non-uniform pieces with average size 20 cm×20 cm.

X grams of feedstock was placed into a round bottom flask. Y mL of 69% nitric acid and Z grams of solid state catalyst were added to the flask; the plastics were submerged in the liquid solution. The bottom of the flask was heated in a heating mantle; the opening of the flask was connected to a condenser. A stir bar was used to agitate the content. Once the desired temperature was reached, the reaction was timed for K hours. Then, the flask was allowed to cool to room temperature while stirring continued. (See Table 6 below for specific numeric values for X, Y, Z and K used in Examples 6a-6d.).

Subsequently, filtration via filter paper was performed to separate the solids (oligomeric resin and solid state catalyst) from the liquids. Distillation was performed on the liquid solution for a period of 1 hour to recover the nitric acid. The remaining crystalline solids were placed in the desiccator overnight. The weight of the dried crystals was 40 percent of the initial weight of the films. This solid comprised a mixture of C4-C10 dibasic acids.

TABLE 6

| Data According to Examples 6a-6d. | | | | | | |
|---|---|---|---|---|---|---|
| Example No. | Feedstock mass (g) | Nitric acid content (mL) | Solid State Catalyst (g) | Reaction time (hours) | Oligomers (% yield by weight) | Crude acids (% yield by weight) |
| 6a | 30 | 105 | 3 (zeolite) | 3 | 138 | 58 |
| 6b | 30 | 150 | 1 (zeolite) | 24 | 36 | 80 |
| 6c | 40 | 150 | 3 (zeolite) | 24 | 75 | 36 |
| 6d | 30 | 150 | 1 (alumina) | 5 | 87 | 55 |

Example 7

200 mg of LDPE (cut from air/bubble packaging) was added to a 100 mL glass lined stainless steel pressure reactor, which was sealed. The reactor was purged with $N_2$, and then pressured to 40 psi with NO, 460 psi with $N_2$, and 100 psi with $O_2$. The reactor was heated to 110° C. for 1 hour, following which it was cooled and the pressure released. The resulting crude product mixture (decomposition mixture) was removed and extracted with methanol. The methanol soluble product mixture recovery was 69% by weight and consisted of dibasic acids.

Example 8

200 mg of LDPE (cut from air/bubble packaging) and 200 mg HDPE (cut from a plastic grocery bag) were added to a 100 mL glass lined stainless steel pressure reactor, which was sealed. The reactor was purged with $N_2$, and then pressured to 40 psi with NO, 460 psi with $N_2$, and 100 psi with $O_2$. The reactor was heated to 120° C. for 2 hours, following which it was cooled and the pressure released. The resulting crude product mixture (decomposition mixture) was removed and extracted with methanol. The methanol soluble product mixture recovery was 49% by weight. After methanol removal, the remaining crude product comprised dicarboxylic acids detected as their respective dimethyl esters.

Analysis

Qualitative and quantitative analysis of the acid products were performed by GC-MS on a DB-1 column. The crude products mentioned in the above examples esterified overnight with methanol in the presence of acetyl chloride. The derivatized products were filtered and then diluted 25×-100× in methanol.

Figure 2:
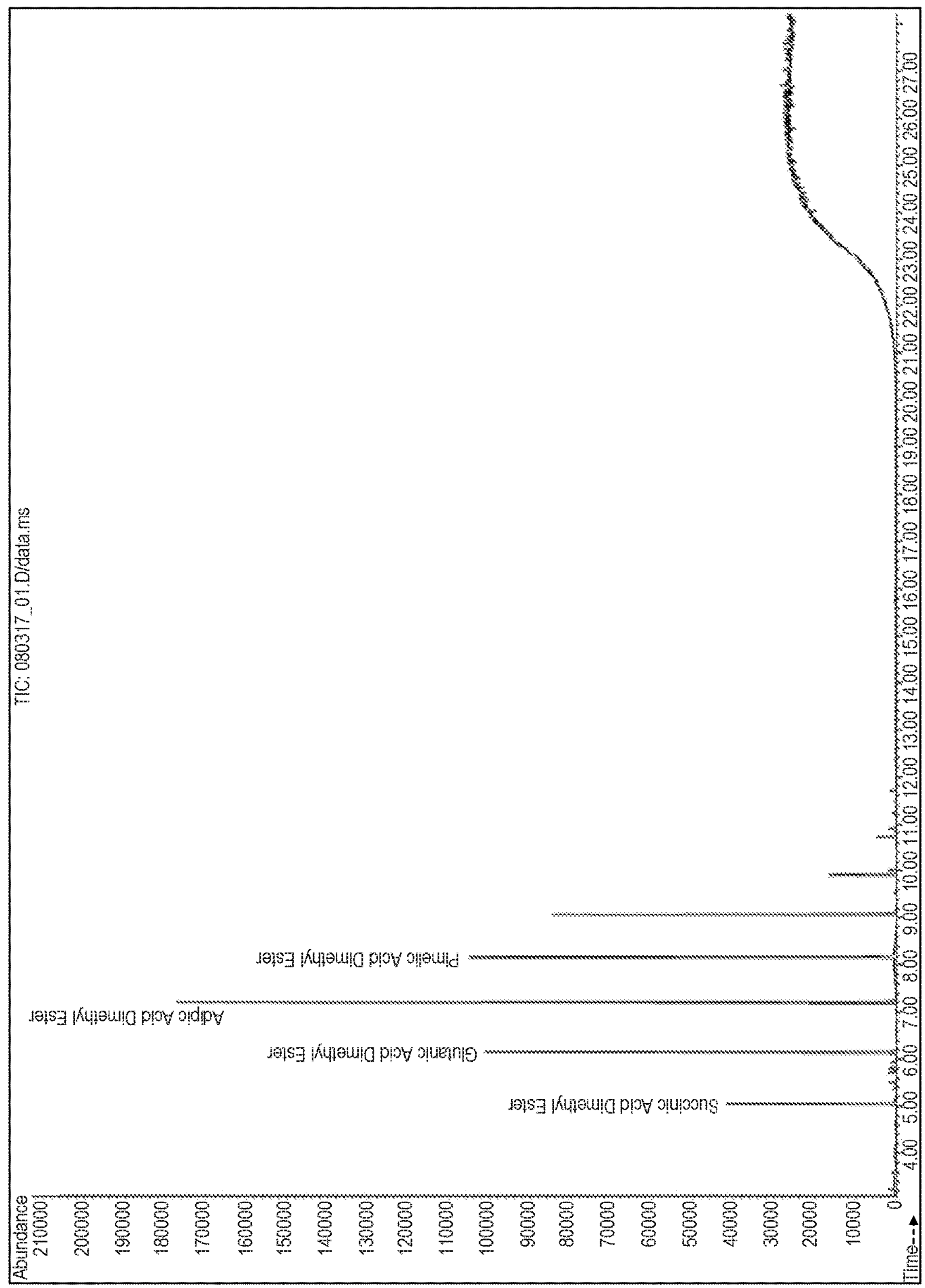
FIG. 2 depicts, in accordance with various embodiments of the invention, a chromatogram of a PE film oxidation product showing dibasic acids in the form of esters.

Calibration curves were constructed for four major compounds: dimethyl succinate (C4), dimethyl glutarate (C5), dimethyl adipate (C6), and dimethyl pimelate (C7). Quantitation was based on the TIC and the percentage values were calculated based on the mass of each sample. The GC-MS has also identified longer chain dimethyl esters, such as dimethyl suberate (C8), dimethyl azelate (C9), dimethyl sebacate (C10), and occasionally undecanedioic acid dimethyl ester (C11), and dodecanedioic acid dimethyl ester (C12), but these were not quantified. Such a chromatogram can be seen in FIG. 2.

Figures 3A, 3B:
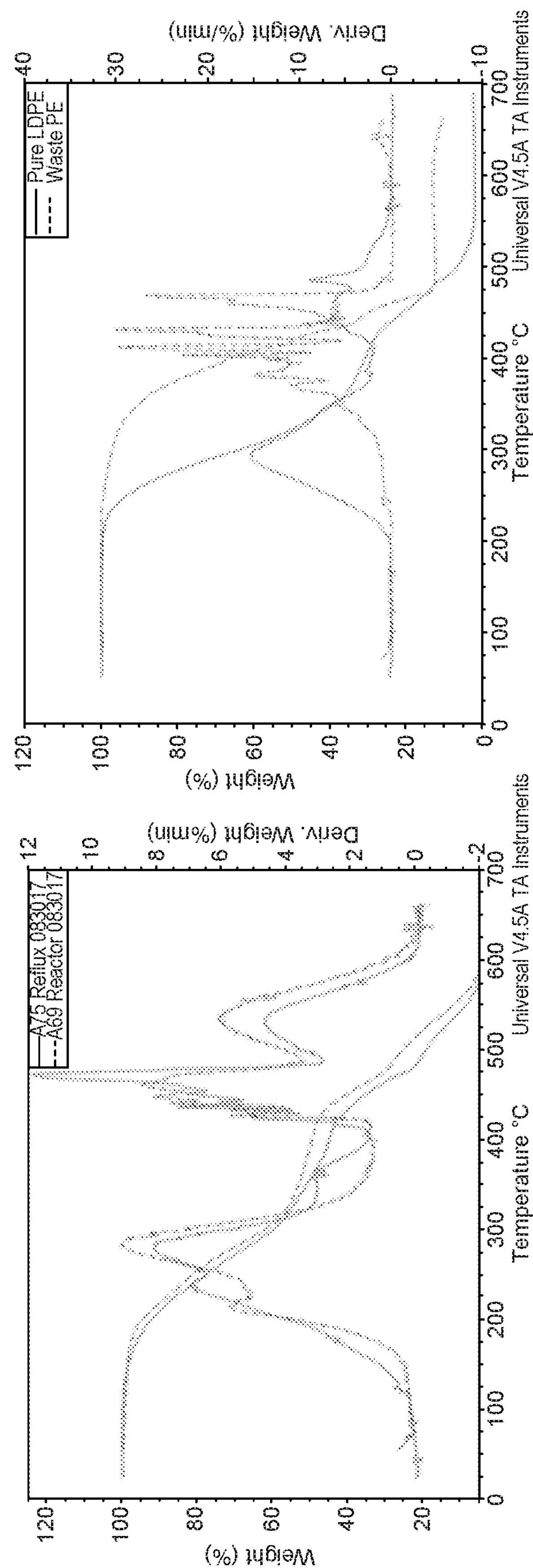
FIG. 3A-FIG. 3B depict, in accordance with various embodiments of the invention, TGA curves contrasting thermal decomposition patterns of resin samples (FIG. 3A) to pure LDPE and waste PE film (FIG. 3B).

Oligomeric resins were preliminarily characterized by thermogravimetric analysis (TGA) and differential scanning calorimetry (DSC). These oligomeric resins possessed different chemical properties from the original PE feedstock. FIG. 3A-FIG. 3B contrasts the decomposition patterns between oligomeric resin (FIG. 3A) and PE (FIG. 3B).

Figure 4:
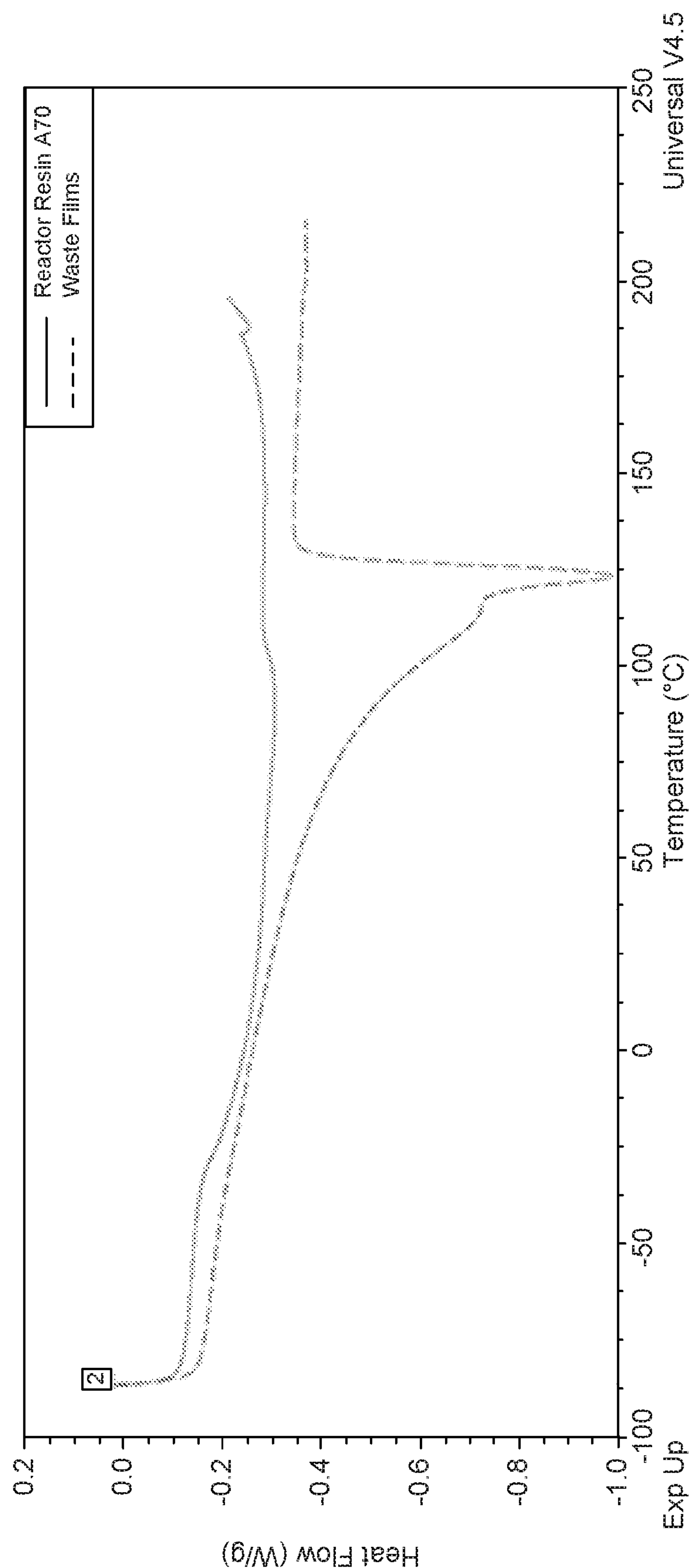
FIG. 4 depicts, in accordance with various embodiments of the invention, DSC curves contrasting crystalline behaviors of waste PE films and resin product.

FIG. 4 shows that while the waste PE film has crystallinity around 120° C., while the resin product has lost crystallinity.

Example 9

The feedstock for this example was 10 g polyethylene and 100 g 70 wt % aqueous nitric acid. The batch reaction was conducted for 9 hours at 120° C. and atmospheric pressure.

The products were dicarboxylic acids (50-65 wt %) and a separate fraction (35-50 wt %) containing other components including nitro-substituted dicarboxylic acids. The dicarboxylic acids were separated by distillation of the reaction filtrate followed by evaporation to remove the majority of aqueous nitric acid. Table 7 provides the ranges of various dicarboxylic acids that were found in that fraction.

TABLE 7

| Dicarboxylic acid | Wt % |
|---|---|
| Oxalic acid (C2) | 0-10% |
| Malonic acid (C3) | 0% |
| Succinic acid (C4) | 5-18% |
| Glutaric acid (C5) | 8-28% |
| Adipic acid (C6) | 10-29% |
| Pimelic acid (C7) | 10-20% |
| Suberic acid (C8) | 9-20% |
| Azelaic acid (C9) | 8-13% |
| Sebacic acid (C10) | 1-10% |
| Undecanedioic acid (C11) | 1-8% |
| Dodecanedioic acid (C12) | 0-5% |
| Tridecanedioic acid (C13) | 0-4% |
| Tetradecanedioic acid (C14) | 0-2% |
| Pentadecanedioic acid (C15) | 0-0.4% |

Example 10

A 250 mL round bottom flask equipped with a magnetic stir bar was loaded with 10 g polyethylene and 100 g 67 wt % $HNO_3$. The reaction flask was equipped with a glass thermometer, placed onto a temperature controlled IKA heating plate and attached to a water condenser. The reaction flask was stirred at maximum stir rate (2000 RPM setting) and heated to a desired reaction temperature. The beginning of the reaction time was marked once the desired temperature has been reached (~15-20 mins). After reaction time, the heater was turned off, the reaction flask lifted from the heater, and quickly cooled while stirring (~15-20 mins). The final mixture (aqueous product stream) was filtered through a filter paper on a Hirsch funnel into a 250 mL beaker. Filtrate collected in the 250 mL beaker was evaporated on a hot plate at 75° C. to obtain crude dicarboxylic acid product. The crude dicarboxylic acid was subjected to GC analysis for dicarboxylic acid composition and LC analysis for additional product composition. The results are shown in Table 8.

TABLE 8

| Dicarboxylic acid | Wt % |
|---|---|
| Oxalic acid (C2) | 0% |
| Malonic acid (C3) | 0% |
| Succinic acid (C4) | 10-11% |
| Glutaric acid (C5) | 15-18% |
| Adipic acid (C6) | 16-18% |
| Pimelic acid (C7) | 15-17% |
| Suberic acid (C8) | 13-15% |
| Azelaic acid (C9) | 10-12% |
| Sebacic acid (C10) | 5-9% |
| Undecanedioic acid (C11) | 3-6% |
| Dodecanedioic acid (C12) | 1-3% |
| Tridecanedioic acid (C13) | 0.5-1.5% |
| Tetradecanedioic acid (C14) | 0-0.2% |
| Pentadecanedioic acid (C15) | 0-0.2% |

Example 11

Powdered pure polyethylene was added to a beaker and 67 wt % aqueous nitric acid was added at a mass ratio of 10:1 aqueous nitric to polyethylene. The mixture was heated at 120° C. for 6 hours and a sample taken for analysis by quadrupole time of flight liquid chromatography mass spectrometry (QTOF-LCMS). The major compounds detected where dicarboxylic acids and their nitration products. FIGS. 22A-C provide a summary of the LCMS results for the sample.

Example 12

Figure 23:
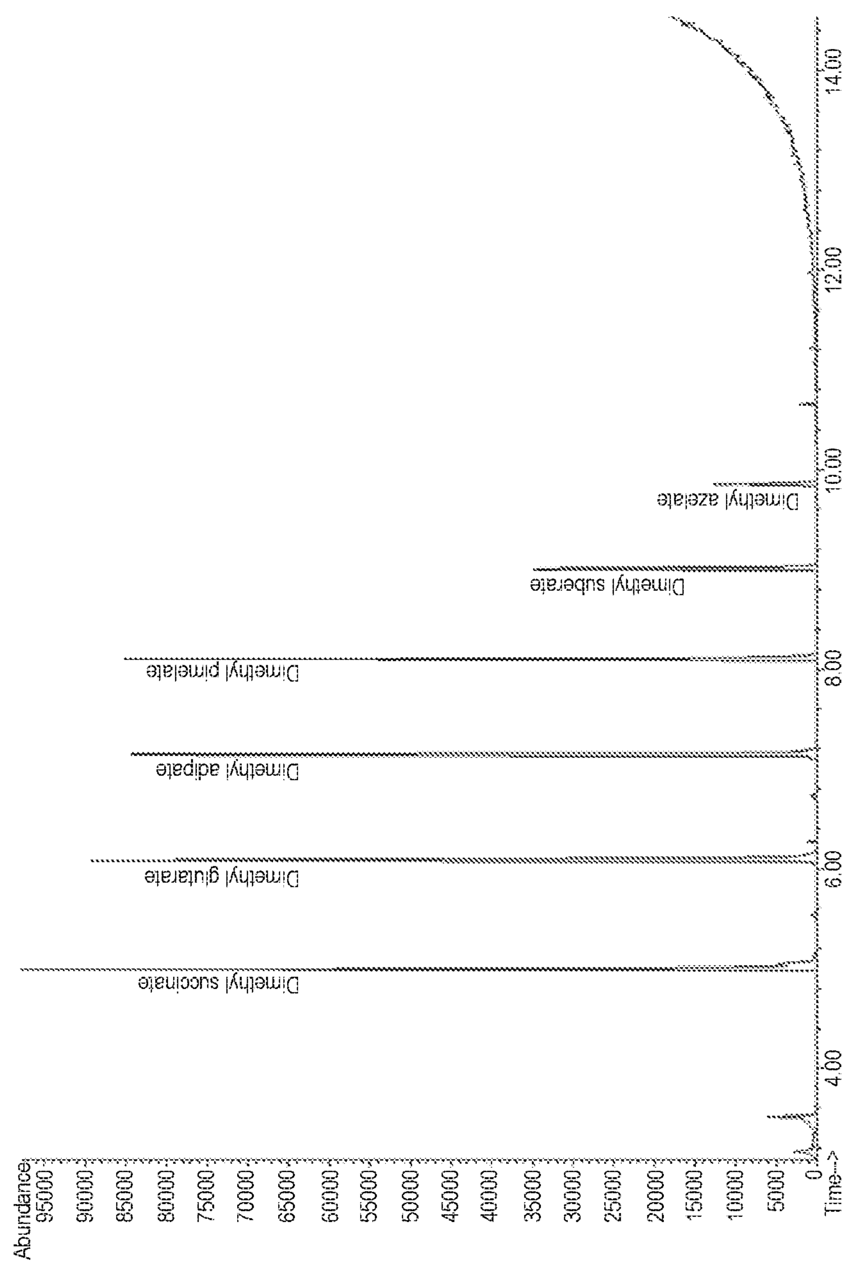
FIG. 23 depicts, in accordance with various embodiments of the invention, a graph showing the analysis of methyl esters of dicarboxylic acids in a reaction product.

The make the methyl esters of dicarboxylic acids for analysis, in a 20 mL scintillation vial, ~60 mg of sample was dissolved in ~6 g of MeOH. ~200 uL of AcCl was added. (Addition of AcCl is exothermic and hence addition is performed dropwise in small scale and in ice bath in large scale.) The target concentration for above solution was aimed to be ~10000 ppm. If >10000 ppm, required dilution was performed. ~1 mL of solution, with 10000 ppm sample, was transferred to an 8 mL vial. And 175 mg of anhydrous $Na_2SO_4$ was added. The mixture was placed in a 40° C. oven or a hot plate for 1 hour. After 1 hour, the mixture was cooled to RT and 40× dilution was performed. For each dilution and solution preparation, masses and densities were recorded so that their respective volumes could be calculated. The results are shown in FIG. 23.

Example 13

This Example shows the effect of pressure and temperature on the reaction products.

2 Grams of polyethylene (PE) powder and 20 grams of 25% nitric acid (1:10 PE to nitric acid ratio) were added to a 100 mL glass liner. The liner was loaded into a 100 mL Parr reactor vessel made of corrosion resistant carpenter 20 material and clamped to the reactor head. The Parr reactor was equipped with gas lines for adding gases, pressure gauge, digital pressure sensor, magnetic stirrer, thermocouple and a ceramic heater. A controller was used to control the heating and stirring in the reactor.

Nitrogen gas was purged three times to remove any oxygen/air inside the vessel. Then the vessel was pressurized and leak test was performed to detect any leaks, indicated by pressure drop over time. Leaks were fixed and leak test was repeated until no leaks were detected, and then the reactor was depressurized.

The heater (set to 120° C. to 180° C.) and stirrer (set to 300 RPM) were turned on via the controller. As the temperature inside the reaction vessel reached the desired temperature (~15-20 min), the start time was recorded the reaction proceeded for 6 hours. (Since this was a closed system, as the temperature increased, the pressure inside the reaction vessel also increase due to the increased liquid volume and the generation of gases.)

After the reaction was complete, the reaction vessel was cooled by an external fan to room temperature (~20-30 min). Then, gases were vented and nitrogen was purged to remove any leftover gases before the reactor was opened.

The Product mixture, which contained a solid stream (unreacted or incompletely reacted PE) and a liquid stream (dicarboxylic acid dissolved in nitric acid), was separated via gravity filtration. The dilute nitric acid in the liquid stream was removed via distillation and the remaining solids (which contained dicarboxylic acid) was analyzed using GC-MS. The results are shown in FIG. 24 and Table 9 below

TABLE 9

| Temp (° C.) | dicarboxylic acid yield % |
|---|---|
| 120 | 28% |
| 130 | 38% |
| 140 | 39% |
| 150 | 42% |
| 160 | 39% |
| 180 | 25% |

Figure 24:
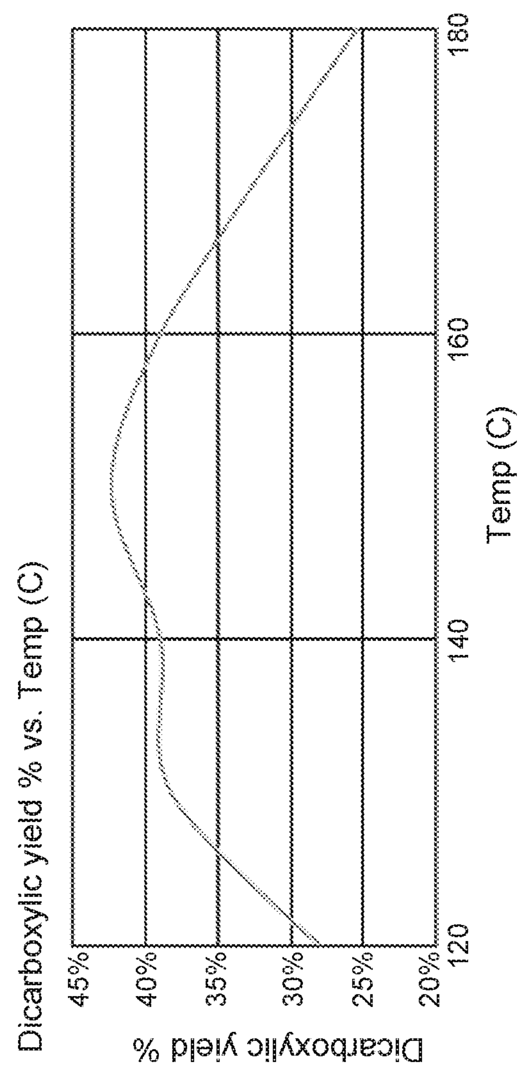
FIG. 24 depicts, in accordance with various embodiments of the invention, a graph showing the yield of dicarboxylic acids at different temperatures.

As shown in FIG. 24 and Table 9, dicarboxylic acid yield % (grams of dicarboxylic acid produced per gram of PE feed) increased with the increase in temperature from 120° C. to 150° C. This is believed to be because the higher temperatures assisted the breakdown of PE into dicarboxylic acid products. Further increase in the temperature from 160° C. to 180° C. decreased the dicarboxylic acid yield % as these higher temperatures may have further converted dicarboxylic acid into gases and other unwanted species.

At lower nitric acid concentration, pressure reactions were able to yield more dicarboxylic acid than reactions conducted at atmospheric pressure with higher nitric acid concentration. As a comparison, a reflux experiment at atmospheric pressure (70% nitric acid, 1:10 PE to nitric acid ratio, 6 hrs, 120° C., 0 Psi) resulted in a 29% dicarboxylic acid yield whereas a pressure reaction (25% nitric acid, 1:10 PE to nitric ratio, 6 hrs, 150° C., 500 Psi) resulted in a 42% dicarboxylic acid yield, with notably higher concentrations of shorter chain dicarboxylic acids (see data in Table 10 below).

TABLE 10

| | C4 | C5 | C6 | C7 | C8 | C9 | C10 | C11 | C12 | C13 | C14 | C15 |
|---|---|---|---|---|---|---|---|---|---|---|---|---|
| Reflux experiment | 13% | 17% | 19% | 18% | 15% | 11% | 4% | 2% | 0.7% | 0.3% | 0.04% | 0.00% |
| 150° C. pressure test | 40% | 27% | 19% | 10% | 4% | 1% | 0% | 0% | 0% | 0% | 0% | 0% |

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Various embodiments of this application are described herein, including the best mode known to the inventors for carrying out the application. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A composition, comprising:

a. succinic acid, glutaric acid, adipic acid, pimelic acid, and azelaic acid, or the salts or esters thereof;

b. at least one of oxalic acid, suberic acid, sebacic acid, undecanedioic acid, dodecanedioic acid, tridecanedioic acid, tetradecanedioic acid, pentadecanedioic acid, 2-octenedioic acid, 2-nonenedioic acid, 2-decenedioic acid, and 2-undecenedioic acid, or the salts or esters thereof; and c. at least one of 2-nitro-suberic acid, 2-nitro-azelaic acid, 2-nitro-sebacic acid, 2-nitro-undecanedioic acid, 2-nitro-dodecanedioic acid, 2-nitro-brassylic acid, 2-nitro-tetradecanedioic acid, 2-nitro-pentadecanedioic acid, 2-nitro-hexadecanedioic acid, 2-nitro-heptadecanedioic acid, 2-nitro-octadecanedioic acid, 2-nitro-nonadecanedioic acid, and 2-nitro-icosanedioic acid, or the salts or esters thereof.

2. The composition of claim 1, wherein a. succinic acid is present in an amount of from about 5 to about 18 wt %, glutaric acid is present in an amount of from about 8 to about 28 wt %, adipic acid is present in an amount of about 10 to about 29 wt %, pimelic acid is present in an amount of about 10 to about 20 wt %, and azelaic acid is present in an amount of about 8 to about 13 wt %, or an equivalent amount of the salts or esters thereof, and b. if present, oxalic acid is present in an amount up to 10 wt %, if present suberic acid is present in an amount of to about 9 to about 20 wt %, if present sebacic acid is present in an amount of about 1 to about 10 wt %, if present undecanedioic acid is present in an amount of about 1 to about 8 wt %, if present dodecanedioic acid is present up to about 5 wt %, if present tridecanedioic acid is present up to about 4 wt %, if present tetradecanedioic acid is present up to about 2 wt %, and if present pentadecanedioic acid is present up to about 0.4 wt %, or an equivalent amount of the salts or esters thereof.

3. The composition of claim 1, wherein a. succinic acid is present in an amount of from about 10 to about 11 wt %, glutaric acid is present in an amount of from about 15 to about 18 wt %, adipic acid is present in an amount of about 16 to about 18 wt %, pimelic acid is present in an amount of about 15 to about 17 wt %, and azelaic acid is present in an amount of about 10 to about 12 wt %, or an equivalent amount of the salts or esters thereof, and b. if present, oxalic acid is present in an amount up to 10 wt %, if present suberic acid is present in an amount of about 13 to about 15 wt %, if present sebacic acid is present in an amount of about 5 to about 9 wt %, if present undecanedioic acid is present in an amount of about 3 to about 6 wt %, if present dodecanedioic acid is present in an amount of about 1 to about 3 wt %, if present tridecanedioic acid is present in an amount of about 0.5 to about 1.5 wt %, if present tetradecanedioic acid is present up to about 0.2 wt %, and if present pentadecanedioic acid is present up to about 0.2 wt %, or an equivalent amount of the salts or esters thereof.

4. The composition of claim 1, wherein a. succinic acid is present in an amount of from about 5 to about 40 wt %, glutaric acid is present in an amount of from about 8 to about 27 wt %, adipic acid is present in an amount of about 10 to about 29 wt %, pimelic acid is present in an amount of about 10 to about 20 wt %, and azelaic acid is present in an amount of about 1 to about 13 wt %, or an equivalent amount of the salts or esters thereof, and b. if present, oxalic acid is present in an amount up to 10 wt %, if present suberic acid is present in an amount of to about 4 to about 20 wt %, if present sebacic acid is present up to about 10 wt %, if present undecanedioic acid is present up to about 8 wt %, if present dodecanedioic acid is present up to about 5 wt %, if present tridecanedioic acid is present up to about 4 wt %, if present tetradecanedioic acid is present up to about 2 wt %, and if present pentadecanedioic acid is present up to about 0.4 wt %, or an equivalent amount of the salts or esters thereof.

5. The composition of claim 1, wherein the acids are at least partially in the form of an alkaline metal salt.

6. The composition of claim 1, wherein the acids are at least partially in the form of esters.

7. The composition of claim 6, wherein the esters are $C_{1-4}$ alkyl esters.

8. The composition of claim 1, wherein the acids are in the form of free acids.

* * * * *